(12) United States Patent
Murphy et al.

(10) Patent No.: US 9,790,273 B2
(45) Date of Patent: Oct. 17, 2017

(54) **ANTI-HLA-B*27 ANTIBODIES AND USES THEREOF**

(71) Applicant: Regeneron Pharmaceuticals, Inc., Tarrytown, NY (US)

(72) Inventors: Andrew J. Murphy, Croton-on-Hudson, NY (US); Ana Kostic, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 860 days.

(21) Appl. No.: 13/855,448

(22) Filed: Apr. 2, 2013

(65) Prior Publication Data

US 2013/0259876 A1    Oct. 3, 2013

Related U.S. Application Data

(60) Provisional application No. 61/618,969, filed on Apr. 2, 2012, provisional application No. 61/778,703, filed on Mar. 13, 2013.

(51) Int. Cl.
*A61K 39/00* (2006.01)
*C07K 16/28* (2006.01)

(52) U.S. Cl.
CPC .......... *C07K 16/28* (2013.01); *C07K 16/2833* (2013.01); *A61K 2039/505* (2013.01); *C07K 2317/21* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 5,369,010 A    11/1994   Nelson et al.
5,734,023 A *   3/1998   Nag ................. C07K 14/70539
                                                      424/185.1

FOREIGN PATENT DOCUMENTS

EP          0213824 A2     3/1987
WO    WO 2012/047294 A2    4/2012
WO    WO 2013/152001 A2   10/2013

OTHER PUBLICATIONS

Rudikoff et al (Proc Natl Acad Sci USA 1982, 79: 1979-1983).*

(Continued)

*Primary Examiner* — Gerald R Ewoldt
*Assistant Examiner* — Marianne DiBrino
(74) *Attorney, Agent, or Firm* — Schwabe, Williamson & Wyatt PC; Christopher Westberg

(57) ABSTRACT

The present invention provides antibodies and antigen-binding fragments thereof that specifically bind HLA-B*27 (also called HLA-B27). In certain embodiments, the antibodies of the invention bind soluble and/or cell surface-expressed forms of HLA-B*27. The antibodies of the present invention, in certain embodiments, inhibit HLA-B*27-mediated activation of T cells. Certain exemplary antibodies of the present invention exhibit enhanced binding to HLA-B*27 as compared to other HLA-B allelic variants (e.g., HLA-B*07). The present invention also provides anti-HLA-B*27 antibodies with pH-dependent binding characteristics (e.g., higher affinity binding at neutral pH than at acidic pH). The antibodies of the invention are useful for the treatment of diseases and disorders associated with HLA-B*27 expression, including ankylosing spondylitis and other spondyloarthropathies.

15 Claims, No Drawings

(56) References Cited

OTHER PUBLICATIONS

Anderson et al (J. Clin. Microbiol. 1986, 23(3): 475-480).*
Shi et al (Canc. Res. 2006, 66: 11946-11953).*
MacCallum et al (J. Mol. Biol. (1996) 262, 732-745).*
Wu et al (J. Mol. Biol. (1999) 294, 151-162).*
Coates et al., "Routine HLA-B27 typing by flow cytometry: differentiation of the products of HLA-B*2702, B*2705 and B*2708", European Journal of Immunogenetics, 25:29-37, (1998).
Darke et al., "One-tube HLA-B27/B2708 typing by flow cytometry using two 'Anti-HLA-B27' monoclonal antibody reagents", Cytometry Part B (Clinical Cytometry), 78B:21-30, (2010).
Levering et al. "Flow Cytometric Screening for the HLA-B27 Antigen on Peripheral Blood Lymphocytes," Current Protocols in Cytometry, John Wiley & Sons, Inc., pp. 6.22.1-6.22.12, (2005).
Levering et al., "Flow cytometric HLA-B27 screening: Cross-reactivity patterns of commercially available anti-HLA-B27 monoclonal antibodies with other HLA-B antigens," Cytometry Part B (Clinical Cytometry), 54B:28-38, (2003).
McHugh et al., "HD6: a novel monoclonal antibody that recognises a subset of HLA-B27 molecules strongly implicated in spondyloarthritis disease pathogenesis," Immunology, 135(Suppl. 1):155-155, (2011). Abstract No. 358.
Payeli et al., "Inhibiting HLA-B27 homodimer-driven immune cell inflammation in spondylarthritis", Arthritis & Rheumatism, 64(10):3139-3149, (2012).
Pei et al., "A Monospecific HLA-B27 Fluorescein isothiocyanate conjugated monoclonal antibody for rapid, simple and accurate HLA-B27 typing", Human Immunology, 36(01):55-55, (1993). Abstract No. IV-50.
Pei et al., "A monospecific HLA-B27 fluorescein isothiocyanate-conjugated monoclonal antibody for rapid, simple and accurate HLA-B27 typing," Tissue Antigens, 41(4):200-203, (1993).
Trapani et al., "Description of a mouse monoclonal anti-HLA-B27 antibody HLA-ABC-m3," Human Immunology, 7(4):205-216, (1983).
Weyl et al., "Epitope mapping of human monoclonal antibodies to HLA-B27 by using natural and mutated antigenic variants," Human Immunology, 31(4):271-276, (1991).
WIPO Application No. PCT/US2013/034952, PCT International Search Report and Written Opinion of the International Searching Authority mailed Nov. 14, 2013.

* cited by examiner

ANTI-HLA-B*27 ANTIBODIES AND USES THEREOF

CROSS-REFERENCE TO RELATED APPLICATIONS

This application claims the benefit under 35 U.S.C. §119 (e) of U.S. provisional application No. 61/618,969, filed on Apr. 2, 2012; and 61/778,703, filed on Mar. 13, 2013, the disclosures of which are herein incorporated by reference in their entireties.

FIELD OF THE INVENTION

The present invention relates to antibodies, and antigen-binding fragments thereof, which are specific for human HLA-B*27, and methods of use thereof.

BACKGROUND

The major histocompatibility complex (MHC) in humans is known as human leukocyte antigen (HLA). HLA molecules are critically involved in antigen presentation and immune responses. HLA-B*27 is a particular HLA allele associated with a high incidence of ankylosing spondylitis and other seronegative spondyloarthropathies.

HLA class 1 molecules such as HLA-B*27 consist of two chains: a membrane-bound heavy chain consisting of three Ig-domains (alpha-1, alpha-2 and alpha-3), and a non-covalently-associated common light chain known as beta-2-microglobulin (β2m). Several allelic subtypes of HLA-B*27 exist, including HLA-B*2701 through HLA-B*2728. Sequence differences between HLA alleles are mostly confined to the peptide-binding cleft between the alpha-1 and alpha-2 domains of the heavy chain. Presentation of peptides of intracellular origin (self- or viral peptides) in the context of HLA-B*27 leads to activation of HLA-restricted T cell clones expressing T cell receptors (TCR) specific for the particular peptide.

Antibodies against HLA-B*27 are generally known in the art, but are mainly described for use in diagnostic and/or detection applications. (See, e.g., U.S. Pat. No. 5,369,010, and Urban et al., *Proc. Natl. Acad. Sci. USA* 91:1534-1538 (1994)). Thus, a need exists in the art for new, high-affinity binding anti-HLA-B*27 antibodies that are suitable for therapeutic applications and other utilities.

BRIEF SUMMARY OF THE INVENTION

The present invention provides antibodies that specifically bind human HLA-B*27. The antibodies of the invention are useful, inter alia, for interfering with T-cell recognition of antigens presented by HLA-B*27 and for treating diseases and disorders caused by or related to HLA-B*27-mediated antigen presentation. For example, the antibodies of the present invention can be administered to a patient for the treatment or alleviation of ankylosing spondylitis and other spondyloarthropathies.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

The present invention provides an antibody or antigen-binding fragment of an antibody comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, and 370, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, and 378, or a substantially similar sequence thereof having at least 90%, at least 95%, at least 98% or at least 99% sequence identity.

The present invention also provides an antibody or antigen-binding fragment thereof comprising a HCVR and LCVR(HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, and 370/378.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, and 376, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, and 384, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 376/384.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, and 372, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, and 374, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, and 380, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, and 382, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M2477N); 20-22-24-28-30-32 (e.g. H1M2490N); 36-38-40-44-46-48 (e.g. H2M2482N); 52-54-56-60-62-64 (e.g. H1M2477N2); 68-70-72-76-78-80 (e.g. H1M2490N2); 84-86-88-92-94-96 (e.g. H2M2482N2); 100-102-104-108-110-112 (e.g. H1M2480N); 116-118-120-124-126-128 (e.g. H1M2497N); 132-134-136-140-142-144 (e.g. H2M2491N); 148-150-152-156-158-160 (e.g. H2M2499N); 164-166-168-172-174-176 (e.g. H2M2718N); 180-182-184-188-190-192 (e.g. H4H2524P); 196-198-200-204-206-208 (e.g. H4H2526P); 212-214-216-220-222-224 (e.g. H4H2528P); 228-230-232-236-238-240 (e.g. H4H2530S); 244-246-248-252-254-256 (e.g. H4H2532P); 260-262-264-268-270-272 (e.g. H4H2534S); 276-278-280-284-286-288 (e.g. H4H2538P); 292-294-296-300-302-304 (e.g. H4H2542P); 308-310-312-316-318-320 (e.g. H4H2555P); 324-326-328-332-334-336 (e.g. H4H2559P); 340-342-344-348-350-352 (e.g. H4H2560P); 356-358-360-364-366-368 (e.g. H4H2562S); and 372-374-376-380-382-384 (e.g. H4H2564S).

In a related embodiment, the invention includes an antibody or antigen-binding fragment of an antibody which specifically binds HLA-B*27, wherein the antibody or fragment comprises the heavy and light chain CDR domains contained within heavy and light chain sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, and 370/378. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In a related embodiment, the invention includes an isolated antibody or antigen-binding fragment thereof that exhibits enhanced binding to HLA-B*27 as compared to other HLA-B allelic variants, the antibody or antigen-binding fragment comprising HCDR1-HCDR2-HCDR3-LCDR1-LCDR2-LCDR3 domains that comprise SEQ ID NOs:52-54-56-60-62-64, respectively, with a histidine substitution in the HCDR1 domain at amino acid position 33, a histidine substitution in the HCDR2 domain at amino acid position 52, or a histidine substitution in the HCDR1 domain at amino acid position 33 and a histidine substitution in the HCDR2 at amino acid position 52.

In a related embodiment, the invention includes an isolated antibody or antigen-binding fragment thereof that exhibits enhanced binding to HLA-B*27 as compared to other HLA-B allelic variants, the antibody or antigen-binding fragment comprising HCDR1-HCDR2-HCDR3-LCDR1-LCDR2-LCDR3 domains that comprise SEQ ID NOs:148-150-152-156-158-160, respectively, with one or more histidine substitutions: a histidine substitution in the HCDR1 domain at amino acid position 32; a histidine substitution in the HCDR2 domain at amino acid position 53; a histidine substitution in the HCDR1 domain at amino acid position 32 and a histidine substitution in the HCDR2 domain at amino acid position 53; a histidine substitution in the LCDR1 domain at amino acid positions 27, 30 and 32; a histidine substitution in the LCDR1 domain at amino acid positions 27, 28 and 32; a histidine substitution in the LCDR1 domain at amino acid positions 28, 30 and 32; a histidine substitution in the LCDR1 domain at amino acid positions 28, 30 and 31; a histidine substitution in the LCDR1 domain at amino acid positions 27, 28, 30 and 32; a histidine substitution in the LCDR3 domain at amino acid positions 90, 92, 93 and 97; a histidine substitution in the LCDR3 domain at amino acid positions 90, 92 and 97; a histidine substitution in the LCDR3 domain at amino acid positions 92, 93 and 97; a histidine substitution in the LCDR3 domain at amino acid positions 90 and 93; a histidine substitution in the LCDR3 domain at amino acid positions 92 and 93; a histidine substitution in the HCDR3 domain at amino acid positions 98, 100 and 106; a histidine substitution in the HCDR3 domain at amino acid positions 98, 100 and 104; a histidine substitution in the HCDR3 domain at amino acid positions 100, 104 and 106; a histidine substitution in the HCDR3 domain at amino acid positions 98, 100, 104 and 106; a histidine substitution in the HCDR3 domain at amino acid positions 98, 104 and 106; a histidine substitution in the HCDR3 domain at amino acid positions 100, 104 and 106 and a histidine substitution in the LCDR1 domain at amino acid positions 28, 30 and 31; a histidine substitution in the HCDR3 domain at amino acid positions 100, 104 and 106 and a histidine substitution in the LCDR3 domain at amino acid positions 90, 92 and 97; or a histidine substitution in the HCDR3 domain at amino acid positions 100, 104 and 106 and a histidine substitution in the LCDR3 domain at amino acid positions 92, 93 and 97.

In a related embodiment, the invention includes a histidine-substituted isolated antibody or antigen-binding fragment that binds HLA-B*2705 at pH 6.0 with a $EC_{50}$ that is at least 1.5-times greater than the $EC_{50}$ for the antibody binding to HLA-B*2705 at pH 7.2.

In another embodiment, the invention includes an isolated antibody or antigen-binding fragment thereof that binds HLA-B*27 at pH 5.75 with a $K_D$ that is at least 5-times, at least 10-times, at least 12-times or at least 25-times greater than the $K_D$ for the antibody binding to HLA-B*27 at pH 7.2. In some embodiments, the antibody or antigen-binding fragment thereof that binds HLA-B*27 at pH 5.75 with a $K_D$ that is greater than the $K_D$ for the antibody binding to HLA-B*27 at pH 7.2 comprises a HCVR/LCVR amino acid sequence pair selected from the group consisting of: SEQ ID NOs: 226/234, 258/266, 290/298, 338/346, and 370/378.

In a related embodiment, the invention includes an isolated antibody or antigen-binding fragment thereof that binds HLA-B*2705 at pH 6.0 with a $EC_{50}$ that is at least 1.5-times, at least 10-times, at least 12 times or at least 25-times greater than the $EC_{50}$ for the antibody binding to HLA-B*2705 at pH 7.2.

In another aspect, the invention provides nucleic acid molecules encoding anti-HLA-B*27 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, and 369, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, and 377, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, and 375, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, and 383, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, and 371, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, and 373, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, and 379, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, and 381, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: SEQ ID NOs: 1 and 9 (e.g. H1M2477N), 17 and 25 (e.g. H1M2490N), 33 and 41 (e.g. H2M2482N), 49 and 57 (e.g. H1M2477N2), 65 and 73 (e.g. H1M2490N2), 81 and 89 (e.g. H2M2482N2), 97 and 105 (e.g. H1M2480N), 113 and 121 (e.g. H1M2497N), 129 and 137 (e.g. H2M2491N), 145 and 153 (e.g. H2M2499N), 161 and 169 (e.g. H2M2718N), 177 and 185 (e.g. H4H2524P), 193 and 201 (e.g. H4H2526P), 209 and 217 (e.g. H4H2528P), 225 and 233 (e.g. H4H2530S), 241 and 249 (e.g. H4H2532P), 257 and 265 (e.g. H4H2534S), 273 and 281 (e.g. H4H2538P), 289 and 297 (e.g. H4H2542P), 305 and 313 (e.g. H4H2555P), 321 and 329 (e.g. H4H2559P), 337 and 345 (e.g. H4H2560P), 353 and 361 (e.g. H4H2562S), and 369 and 377 (e.g. H4H2564S).

The present invention includes anti-HLA-B*27 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a human antibody or antigen-binding fragment thereof which specifically binds HLA-B*27 and a pharmaceutically acceptable carrier. In a related aspect, the invention features a composition comprising a combination of an anti-HLA-B*27 antibody and a second therapeutic agent. In one embodiment, the second therapeutic agent is any agent that is advantageously combined with an anti-HLA-B*27 antibody. Exemplary agents that may be advantageously combined with an anti-HLA-B*27 antibody include, without limitation, other agents that inhibit HLA-B*27 activity (including other antibodies or antigen-binding fragments thereof, peptide inhibitors, small molecule antagonists, etc) and/or agents which do not directly bind HLA-B*27 but nonetheless interfere with, block or attenuate HLA-B*27-mediated T-cell activation.

In yet another aspect, the invention provides methods for inhibiting HLA-B*27-mediated activity using an anti-HLA-B*27 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated, prevented or ameliorated can be any disease or condition which is improved, ameliorated, inhibited or prevented by removal, inhibition or reduction of HLA-B*27 activity (e.g., HLA-B*27-mediated antigen presentation). The anti-HLA-B*27 antibodies or antibody fragments of the invention may function to interfere with the interaction of an HLA-B*27/peptide complex with a T-cell receptor, or to otherwise inhibit HLA-B*27-mediated antigen presentation and/or T-cell activation. Thus, one aspect of the invention are methods for treating, preventing or ameliorating a disease or disorder associated with or mediated by HLA-B*27 activity, the method comprising administering a pharmaceutical composition comprising an antibody or antigen-binding fragment of an antibody of the invention to a patient afflicted with or at risk for a disease or disorder associated with or mediated by HLA-B*27 activity. In some embodiments of the invention, the disease or disorder associated with or mediated by HLA-B*27 activity is spondyloarthropathy, rejection of solid organ transplants, or graft-versus-host disease (GVHD). In some embodiments of the invention, the spondyloarthropathy that is treated, prevented or ameliorated by methods of the invention are ankylosing spondylitis, reactive arthritis (Reiter's Syndrome), acute anterior uveitis, iritis, psoriatic arthritis, and/or ulcerative colitis.

The present invention also includes the use of an anti-HLA-B*27 antibody or antigen binding portion of an antibody of the invention in the manufacture of a medicament for the treatment of a disease or disorder related to or caused by HLA-B*27 activity.

Other embodiments will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "HLA-B*27" (alternatively referred to as "HLA-B27") means a polypeptide complex comprising the alpha-1, alpha-2 and alpha-3 Ig domains of an HLA-B*27 allelic heavy chain, in association with a beta-2-microglobulin polypeptide. The expression "HLA-B*27," as used herein, encompasses all allelic subvariants of the HLA-B*27 family, including HLA-B*2701 through HLA-B*2728. An exemplary HLA-B*27 allelic subvariant is HLA-B*2705 comprising a heavy chain having the amino acid sequence of SEQ ID NO:385. Another exemplary HLA-B*27 allelic subvariant is HLA-B*2709 comprising a heavy chain having the amino acid sequence of SEQ ID NO:386. The amino acid sequences of other HLA-B*27 allelic subvariants are available from public databases and will be well known to persons of ordinary skill in the art. The expression "HLA-B*27" includes cell surface expressed HLA-B*27 complexes (see, e.g., Examples 4-6 herein) as well as artificially engineered soluble fusion proteins comprising HLA-B*27 alpha-1, alpha-2 and alpha-3 Ig domains fused to a beta-2-microglobulin protein and optionally an HLA-restricted peptide (see, e.g., Example 3 herein). An example of one such soluble HLA-B*27 fusion protein is the construct referred to herein as "scHLA-B27" which comprises the amino acid sequence of SEQ ID NO:387.

The term "antibody", as used herein, means any antigen-binding molecule or molecular complex comprising at least one complementarity determining region (CDR) that specifically binds to or interacts with a particular antigen (e.g., HLA-B*27). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L 1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-HLA-B*27 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., Proc. Natl. Acad. Sci. (USA) 95:652-656 (1998)). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al., Nucl. Acids Res. 20:6287-6295 (1992)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The present invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

A "neutralizing" or "blocking" antibody, as used herein, is intended to refer to an antibody whose binding to HLA-B*27 inhibits the interaction between an HLA-B*27/peptide complex and a T-cell receptor. The inhibition caused by an HLA-B*27 neutralizing or blocking antibody need not be complete so long as it is detectable using an appropriate assay. Exemplary assays for determining if an antibody blocks the interaction between HLA-B*27 and a T-cell receptor are known in the art and described elsewhere herein.

The anti-HLA-B*27 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-HLA-B*27 antibodies comprising variants of any of the HCVR, LCVR, and/or CDR amino acid sequences disclosed herein having one or more conservative substitutions. For example, the present invention includes anti-HLA-B*27 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The present invention also includes anti-HLA-B*27 antibodies comprising variants of anti-HLA-B*27 antibodies with pH-dependent binding properties (i.e., reduced binding at low pH as compared to neutral pH), enhanced binding to subvariants of HLA-B*27 (e.g., greater binding affinity for HLA-B*2705 and/or HLA-B*2709 as compared to HLA-B*07), and improved in vivo efficacy (e.g., longer antibody serum half-life, prolonged inhibition of T-cell activation, etc.). Such variants include anti-HLA-B*27 antibody variants in which the CDR sequences of a parental anti-HLA-B*27 antibody have been altered to replace one or more non-histidine amino acids by a histidine residue. Examples of "parental" anti-HLA-B*27 antibodies which can be modified, mutated, or otherwise engineered to possess altered binding characteristics (e.g., enhanced pH-dependent binding characteristics) include anti-HLA_B*27 antibodies comprising any of the complementarity determining regions (CDRs) or heavy and light chain variable domains (HCVR/LCVR) as disclosed in Example 2, Table 1, herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 24: 307-331 (1994), hereby incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., *Science* 256: 1443-1445 (1992), hereby incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al., *J. Mol. Biol.* 215:403-410 (1990) and Altschul et al., *Nucleic Acids Res.* 25:3389-402 (1997), hereby incorporated by reference.

Biological Characteristics of the Antibodies

The present invention includes antibodies that specifically bind HLA-B*27. The term "specifically binds," or the like, means that an antibody or antigen-binding fragment thereof forms a complex with an antigen that is relatively stable under physiologic conditions. Specific binding can be characterized by a $K_D$ of about $1\times10^{-7}$ M or less at 25° C. and neutral pH. Methods for determining whether two molecules specifically bind are well known in the art and include, for example, equilibrium dialysis, surface plasmon resonance, and the like. An isolated antibody that specifically binds a particular HLA-B*27 allelic subvariant may, however, have cross-reactivity to other HLA-B*27 allelic subvariants. Thus, antibodies that "specifically bind HLA-B*27" include antibodies that specifically bind all or a subset of HLA-B*27 allelic subvariants. For example, an antibody that specifically binds HLA-B*2705 and/or HLA-B*2709 is considered an antibody that "specifically binds HLA-B*27."

The present invention includes anti-HLA-B*27 antibodies that bind a soluble HLA-B*27 fusion protein (e.g., scHLA-B27-mmH [SEQ ID NO:387]) with a $K_D$ of less than about 260 nM at 25° C. and neutral pH (e.g., about pH 7.2). For example, the present invention includes anti-HLA-B*27 antibodies that bind scHLA-B27-mmH, as tested by surface plasmon resonance at 25° C. and pH 7.2 (see, e.g., Example 3 herein), with a $K_D$ of less than about 250 nM, 200 nM, 150 nM, 100 nM, 50 nM, 1 nM, 900 pM, 850 pM, 800 pM, 750 pM, 700 pM, 650 pM, 600 pM, 550 pM, 500 pM, 450 pm, 400 pM, 350 pM, 300 pM, 250 pM, 200 pM, or less.

The present invention includes anti-HLA-B*27 antibodies that exhibit pH-dependent binding to HLA-B*27. In some embodiments of the invention, the expression "pH-dependent binding", as used herein, means that an antibody exhibits a $K_D$ value at acidic pH (e.g., pH 5.75) that is at least 5-times greater than its $K_D$ value at neutral pH (e.g., pH 7.2), when tested using surface plasmon resonance, wherein the $K_D$ values at acidic and neutral pH are measured under the same or substantially the same experimental conditions (e.g., temperature, antigen/antibody orientation, reagent concentration, flow rate, etc.). For example, an anti-HLA-B*27 antibody is deemed to have "pH-dependent binding" for purposes of the present disclosure if the ratio of its $K_D$ value for binding to HLA-B*27 at pH 5.75 to its $K_D$ value for binding to HLA-B*27 at pH 7.2 is at least about 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 15.0, 20.0, 25.0, or greater (see, e.g., Table 6 [Example 3] herein). In some embodiments of the invention, the expression "pH-dependent binding", as used herein, means that an antibody exhibits a $EC_{50}$ value (i.e., half maximal effective concentration) in a binding assay (e.g., a chemilumenscence assay) at acidic pH (e.g., pH 6.0) that is at least 3 times greater than the $EC_{50}$ value at neutral pH (e.g., pH 7.2), wherein the $EC_{50}$ values at acidic and neutral pH are measured under the same or substantially the same experimental conditions (e.g., temperature, antigen/antibody orientation, reagent concentration, flow rate, etc.). For example, an anti-HLA-B*27 antibody is deemed to have "pH-dependent binding" for purposes of the present disclosure if the ratio of its $EC_{50}$ value for binding to HLA-B*27 at pH 6.0 to its $EC_{50}$ value for binding to HLA-B*27 at pH 7.2 is at least about 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.5, 9.0, 9.5, 10.0, 10.5, 11.0, 11.5, 12.0, 12.5, 13.0, 13.5, 14.0, 15.0, 20.0, 25.0, or greater (see, e.g., Tables 21 and 22 [Example 11] herein). In some embodiments of the invention, pH-dependent binding may be measured in terms of binding associative rate constants ($k_a$), binding dissociative rate constants ($k_d$), or dissociative half-lives ($t_{1/2}$).

The present invention also includes anti-HLA-B*27 antibodies that are capable of blocking or reducing HLA-B*27-mediated T-cell activation in vitro. An exemplary assay for determining whether an antibody blocks or reduces HLA-B*27-mediated T-cell activation in vitro is shown in Example 4 herein. In this Example, two engineered cell lines are used. The first cell line is one that expresses an HLA-B*27 heavy chain allelic variant along with human β2m and an HLA-restricted peptide on its surface. The second cell line is a reporter cell line that expresses a T cell receptor which, when activated, produces a detectable luciferase signal. Varying amounts of anti-HLA-B*27 antibody are added to the first cell line prior to mixing with the reporter cell line, and $10_{50}$ values are calculated. The present invention includes antibodies that exhibit an $10_{50}$ of less than about 12.5 nM when tested in a blocking bioassay as shown in Example 4, or a substantially similar assay. For example, the present invention includes anti-HLA-B*27 antibodies that exhibit an $IC_{50}$ of less than about 12 nM, 10 nM, 8 nM, 6 nM, 4 nM, 2 nM, 1 nM, 900 pM, 850 pM, 800 pM, 750 pM, 700 pM, 650 pM, 600 pM, 550 pM, 500 pM, 450 pm, 400 pM, or less when tested in a blocking bioassay as shown in Example 4, or a substantially similar assay.

The present invention also includes anti-HLA-B*27 antibodies that exhibit enhanced binding to an HLA-B*27 allelic variant (such as, e.g., HLA-B*2705 and/or HLA-B*2709) as compared to other (non-B*27) HLA-B allelic variants (such as, e.g., HLA-B*07). An exemplary assay format for determining if an antibody exhibits enhanced binding to one or more HLA-B*27 allelic variant(s) is shown in Example 8 herein. In this Example, the relative binding of each antibody to cells expressing either HLA-B*07, HLA-B*2705 or HLA-B*2709, as compared to its binding to parental cells that do not express HLA, was determined. Using this type of assay format, an antibody that exhibits at least 50-fold greater binding to cells expressing an HLA-B*27 allelic variant as compared to binding to the parental cell line (represented by [++] or [+++] in Table 15), but less than 10-fold greater binding to cells expressing the non-HLA-B*27 allelic variant (e.g., HLA-B*07) compared to binding to the parental cells (represented [+] in Table 15), is considered an antibody that exhibits "enhanced binding" to HLA-B*27 as compared to another HLA-B allelic variant(s). In certain instances, an antibody is deemed to exhibit "enhanced binding" to HLA-B*27 as compared to other HLA-B allelic variants if the antibody, when tested in the assay format of Example 8 herein or a substantially similar assay format, shows at least 50-fold greater binding to cells expressing an HLA-B*27 allelic variant as compared to binding to the parental cells (represented by [++] or [+++] in Table 15), but less than 3-fold greater binding to cells expressing the non-HLA-B*27 allelic variant (e.g., HLA-B*07) compared to binding to the parental cells (represented by [−] in Table 15).

Epitope Mapping and Related Technologies

The present invention includes anti-HLA-B*27 antibodies which interact with one or more amino acids found within the alpha-1, alpha-2, and/or alpha-3 Ig domains of an HLA-B*27 heavy chain. For HLA-B*2705 (SEQ ID NO:385) and HLA-B*2709 (SEQ ID NO:386), the alpha-1 Ig domain consists of amino acids 25-114, the alpha-2 Ig domain consists of amino acids 115-206, and the alpha-3 Ig domain consists of amino acids 207-298 of the corresponding full heavy chain amino acid sequence. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within one or more Ig domains of an HLA-B*27 heavy chain. Alternatively, the epitope may consist of a plurality of non-contiguous amino acids (or amino acid sequences) located within one or more Ig domains of an HLA-B*27 heavy chain. The antibodies of the present invention may also interact with one or more amino acids within the β2m sequence (SEQ ID NO:388).

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, Methods Mol Biol 248:443-463 (2004)), and peptide cleavage analysis. In addition, methods such as epitope excision, epitope extraction and chemical modification of antigens can be employed (Tomer, Protein Science 9:487-496 (2000)). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring, Analytical Biochemistry 267(2):252-259 (1999); Engen and Smith, Anal. Chem. 73:256 A-265A (2001).

The present invention further includes anti-HLA-B*27 antibodies that bind to the same epitope as any of the specific exemplary antibodies described herein (e.g., H1M2477N, H1M2490N, H2M2482N, H1M2477N2, H1M2490N2, H2M2482N2, H1M2480N, H1M2497N, H2M2491N, H2M2499N, H2M2718N, H4H2524P, H4H2526P, H4H2528P, H4H2530S, H4H2532P, H4H2534S, H4H2538P, H4H2542P, H4H2555P, H4H2559P, H4H2560P, H4H2562S, H4H2564S, etc.). Likewise, the present invention also includes anti-HLA-B*27 antibodies that compete for binding to HLA-B*27 with any of the specific exemplary antibodies described herein (e.g., H1M2477N, H1M2490N, H2M2482N, H1M2477N2, H1M2490N2, H2M2482N2, H1M2480N, H1M2497N, H2M2491N, H2M2499N, H2M2718N, H4H2524P, H4H2526P, H4H2528P, H4H2530S, H4H2532P, H4H2534S, H4H2538P, H4H2542P, H4H2555P, H4H2559P, H4H2560P, H4H2562S, H4H2564S, etc.).

One can easily determine whether an antibody binds to the same epitope as, or competes for binding with, a reference anti-HLA-B*27 antibody by using routine methods known in the art. For example, to determine if a test antibody binds to the same epitope as a reference anti-HLA-B*27 antibody of the invention, the reference antibody is allowed to bind to an HLA-B*27 complex (e.g., a soluble HLA-B*27/peptide fusion protein or a cell surface-expressed HLA-B*27 in complex with an HLA-restricted peptide). Next, the ability of a test antibody to bind to the HLA-B*27 complex is assessed. If the test antibody is able to bind to HLA-B*27 following saturation binding with the reference anti-HLA-B*27 antibody, it can be concluded that the test antibody binds to a different epitope than the reference anti-HLA-B*27 antibody. On the other hand, if the test antibody is not able to bind to the HLA-B*27 complex following saturation binding with the reference anti-HLA-B*27 antibody, then the test antibody may bind to the same epitope as the epitope bound by the reference anti-HLA-B*27 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-HLA-B*27 antibody, the above-described binding methodology is performed in two orientations: In a first orientation, the reference antibody is allowed to bind to an HLA-B*27 complex under saturating conditions followed by assessment of binding of the test antibody to the HLA-B*27 complex. In a second orientation, the test antibody is allowed to bind to an HLA-B*27 complex under saturating conditions followed by assessment of binding of the reference antibody to the HLA-B*27 complex. If, in both orientations, only the first (saturating) antibody is capable of binding to the HLA-B*27 complex, then it is concluded that the test antibody and the reference antibody compete for binding to HLA-B*27. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human HLA-B*27.

Using VELOCIMMUNE™ technology or any other known method for generating monoclonal antibodies, high affinity chimeric antibodies to HLA-B*27 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-HLA-B*27 antibodies and antibody fragments of the present invention encompass proteins having amino acid sequences that vary from those of the described antibodies but that retain the ability to bind human HLA-B*27. Such variant antibodies and antibody fragments comprise one or more additions, deletions, or substitutions of amino acids when compared to parent sequence, but exhibit biological activity that is essentially equivalent to that of the described antibodies. Likewise, the anti-HLA-B*27 antibody-encoding DNA sequences of the present invention encompass sequences that comprise one or more additions, deletions, or substitutions of nucleotides when compared to the disclosed sequence, but that encode an anti-HLA-B*27 antibody or antibody fragment that is essentially bioequivalent to an anti-HLA-B*27 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-HLA-B*27 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-HLA-B*27 antibody variants comprising amino acid changes which modify the glycosylation characteristics of the antibodies, e.g., mutations which eliminate or remove glycosylation.

Immunoconjugates

The invention encompasses anti-HLA-B*27 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., *J. Immunol.* 147:60-69 (1991); Kufer et al., *Trends Biotechnol.* 22:238-244 (2004). The anti-HLA-B*27 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for HLA-B*27 or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab2 bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

Therapeutic Formulation and Administration

The invention provides pharmaceutical compositions comprising the anti-HLA-B*27 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with HLA-B*27 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-HLA-B*27 antibodies may be determined empirically; for example, patient progress can be monitored by periodic assessment, and the dose adjusted accordingly. Moreover, interspecies scaling of dosages can be performed using well-known methods in the art (e.g., Mordenti et al., *Pharmaceut. Res.* 8:1351 (1991)).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., *J. Biol. Chem.* 262:4429-4432 (1987)). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention (and pharmaceutical compositions comprising the same) are useful, inter alia, for the treatment, prevention and/or amelioration of any disease or disorder associated with or mediated by HLA-B*27 activity or treatable by blocking or attenuating HLA-B*27-mediated antigen presentation. Exemplary diseases and disorders that can be treated with the anti-HLA-B*27 antibodies of the present invention include spondyloarthropathies, such as, e.g., ankylosing spondylitis, reactive arthritis (Reiter's Syndrome), acute anterior uveitis, initis, psoriatic arthritis, ulcerative colitis, etc. Additional diseases and disorders that can be prevented, treated and/or ameliorated with the anti-HLA-B*27 antibodies of the present invention include rejection of solid organ transplants and graft-versus-host disease (GVHD).

Administration Regimens

According to certain embodiments of the present invention, multiple doses of anti-HLA-B*27 antibody may be administered to a subject over a defined time course. The methods according to this aspect of the invention comprise sequentially administering to a subject multiple doses of an anti-HLA-B*27 antibody. As used herein, "sequentially administering" means that each dose of anti-HLA-B*27 antibody is administered to the subject at a different point in time, e.g., on different days separated by a predetermined interval (e.g., hours, days, weeks or months). The present invention includes methods which comprise sequentially administering to the patient a single initial dose of an anti-HLA-B*27 antibody, followed by one or more secondary doses of the anti-HLA-B*27 antibody, and optionally followed by one or more tertiary doses of the anti-HLA-B*27 antibody.

The terms "initial dose," "secondary doses," and "tertiary doses," refer to the temporal sequence of administration of the anti-HLA-B*27 antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-HLA-B*27 antibody, but generally may differ from one another in terms of frequency of administration. In certain embodiments, however, the amount of anti-HLA-B*27 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-HLA-B*27 antibody which is administered to a patient prior to the administration of the very next dose in the sequence with no intervening doses.

The methods according to this aspect of the invention may comprise administering to a patient any number of secondary and/or tertiary doses of an anti-HLA-B*27 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Combination Therapies

The present invention includes therapeutic administration regimens which comprise administering an anti-HLA-B*27 antibody of the present invention in combination with at least one additional therapeutically active component. Non-limiting examples of such additional therapeutically active components include other HLA-B*27 blocking agents such as, e.g., a second anti-HLA-B*27 antibody. Other agents that may be beneficially administered in combination with the anti-HLA-B*27 antibodies of the invention include cytokine inhibitors (including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors), antivirals, antibiotics, analgesics, corticosteroids and/or NSAIDs.

The additional therapeutically active component(s) may be administered prior to, concurrent with, or after the administration of an anti-HLA-B*27 antibody of the present invention; (for purposes of the present disclosure, such administration regimens are considered the administration of an anti-HLA-B*27 antibody "in combination with" an additional therapeutically active component).

Diagnostic Uses of the Antibodies

The anti-HLA-B*27 antibodies of the present invention may also be used to detect and/or measure HLA-B*27, or HLA-B*27-expressing cells in a sample, e.g., for diagnostic purposes. For example, an anti-HLA-B*27 antibody, or fragment thereof, may be used to diagnose a condition or disease characterized by the presence of an HLA-B*27 allelic subvariant (e.g., HLA-B*2705 or HLA-B*2709). Exemplary diagnostic assays for HLA-B*27 may comprise, e.g., contacting a sample, obtained from a patient, with an anti-HLA-B*27 antibody of the invention, wherein the anti-HLA-B*27 antibody is labeled with a detectable label or reporter molecule. Alternatively, an unlabeled anti-HLA-B*27 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate or rhodamine; or an enzyme such as alkaline phosphatase, beta-galactosidase, horseradish peroxidase, or luciferase. Specific exemplary assays that can be used to detect or measure HLA-B*27 in a sample include enzyme-linked immunosorbent assay (ELISA), radioimmunoassay (RIA), and fluorescence-activated cell sorting (FACS).

Samples that can be used in HLA-B*27 diagnostic assays according to the present invention include any tissue or fluid sample obtainable from a patient which contains detectable quantities of HLA-B*27 protein, or fragments thereof, under normal or pathological conditions. Generally, levels of HLA-B*27 in a particular sample obtained from a healthy patient (e.g., a patient not afflicted with a disease or condition associated with HLA-B*27 or a particular HLA-B*27 allele) will be measured to initially establish a baseline, or standard, level of HLA-B*27. This baseline level of HLA-B*27 can then be compared against the levels of HLA-B*27 measured in samples obtained from individuals suspected of having an HLA-B*27 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human HLA-B*27

To generate anti-HLA-B*27 antibodies, a VELOCIMMUNE® mouse (see, e.g., U.S. Pat. No. 6,596,541) was immunized according to standard methods with either a soluble HLA-B*27 fusion protein (comprising the HLA-B*2705 heavy chain extracellular domain fused to an HLA-restricted peptide and the β2m sequence), or with tissues/cells expressing HLA-B*27, as well as combinations thereof. The antibody immune response was monitored by an HLA-B*27-specific immunoassay. When a desired immune response was achieved splenocytes were harvested and fused with mouse myeloma cells to preserve their viability and form hybridoma cell lines. The hybridoma cell lines were screened and selected to identify cell lines that produce HLA-B*27-specific antibodies. Using this technique several anti-HLA-B*27 chimeric antibodies (i.e., antibodies possessing human variable domains and mouse constant domains) were obtained; exemplary antibodies generated in this manner were designated as follows: 2477N, 2490N, 2482N, 2477N2, 2490N2, 2482N2, 2480N, 2497N, 2491N, 2499N, and 2718N.

Anti-HLA-B*27 antibodies were also isolated directly from antigen-positive B cells without fusion to myeloma cells, as described in US 2007/0280945A1. Using this method, several fully human anti-HLA-B*27 antibodies (i.e., antibodies possessing human variable domains and human constant domains) were obtained; exemplary antibodies generated in this manner were designated as follows: 2524P, 2526P, 2528P, 2530S, 2532P, 2534S, 2538P, 2542P, 2555P, 2559P, 2560P, 2562S, and 2564S.

Certain biological properties of the exemplary anti-HLA-B*27 antibodies generated in accordance with the methods of this Example are described in detail in the Examples set forth below.

Example 2. Heavy and Light Chain Variable Region Amino Acid Sequences

Table 1 sets forth the amino acid sequence identifiers (SEQ ID NOs) for the heavy and light chain variable regions (HCVRs and LCVRs) and complementarity determining regions (CDRs) of selected anti-HLA-B*27 antibodies.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 2477N | 2 | 4 | 6 | 8 | 10 | 12 | 14 | 16 |
| 2490N | 18 | 20 | 22 | 24 | 26 | 28 | 30 | 32 |
| 2482N | 34 | 36 | 38 | 40 | 42 | 44 | 46 | 48 |
| 2477N2 | 50 | 52 | 54 | 56 | 58 | 60 | 62 | 64 |
| 2490N2 | 66 | 68 | 70 | 72 | 74 | 76 | 78 | 80 |
| 2482N2 | 82 | 84 | 86 | 88 | 90 | 92 | 94 | 96 |
| 2480N | 98 | 100 | 102 | 104 | 106 | 108 | 110 | 112 |
| 2497N | 114 | 116 | 118 | 120 | 122 | 124 | 126 | 128 |
| 2491N | 130 | 132 | 134 | 136 | 138 | 140 | 142 | 144 |
| 2499N | 146 | 148 | 150 | 152 | 154 | 156 | 158 | 160 |
| 2718N | 162 | 164 | 166 | 168 | 170 | 172 | 174 | 176 |
| 2524P | 178 | 180 | 182 | 184 | 186 | 188 | 190 | 192 |
| 2526P | 194 | 196 | 198 | 200 | 202 | 204 | 206 | 208 |
| 2528P | 210 | 212 | 214 | 216 | 218 | 220 | 222 | 224 |
| 2530S | 226 | 228 | 230 | 232 | 234 | 236 | 238 | 240 |
| 2532P | 242 | 244 | 246 | 248 | 250 | 252 | 254 | 256 |
| 2534S | 258 | 260 | 262 | 264 | 266 | 268 | 270 | 272 |
| 2538P | 274 | 276 | 278 | 280 | 282 | 284 | 286 | 288 |
| 2542P | 290 | 292 | 294 | 296 | 298 | 300 | 302 | 304 |
| 2555P | 306 | 308 | 310 | 312 | 314 | 316 | 318 | 320 |
| 2559P | 322 | 324 | 326 | 328 | 330 | 332 | 334 | 336 |
| 2560P | 338 | 340 | 342 | 344 | 346 | 348 | 350 | 352 |
| 2562S | 354 | 356 | 358 | 360 | 362 | 364 | 366 | 368 |
| 2564S | 370 | 372 | 374 | 376 | 378 | 380 | 382 | 384 |

Antibodies are typically referred to herein according to the following nomenclature: Fc prefix (e.g. "H4H", "H1M", "H2M"), followed by a numerical identifier (e.g. "2477" or "2524" as shown in Table 1), followed by a "P", "N" or "S" suffix. Thus, according to this nomenclature, an antibody may be referred to herein as, e.g., "H1M2477N" or "H4H2524P". The H4H, H1M, and H2M prefixes on the antibody designations used herein indicate the particular Fc region of the antibody. For example, an "H1M" antibody has a mouse IgG1 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs)—which are indicated by the numerical identifiers shown in Table 1—will remain the same.

Example 3. Surface Plasmon Resonance Derived Binding Affinities and Kinetic Constants of Human Monoclonal Anti-HLA-B*27 Antibodies Binding associative and dissociative rate constants ($k_a$ and $k_d$, respectively) and calculated equilibrium dissociation constants and dissociative half-lives ($K_D$ and $t_{1/2}$, respectively) for antigen binding to purified anti-HLA-B*27 antibodies were determined using a real-time surface plasmon resonance biosensor assay (Biacore T200, 3000, or T100-2). Antibodies were tested for binding to an engineered HLA-B*27 ectodomain in-line fusion protein ("scHLA-B27-mmH", SEQ ID NO:387) consisting of the following components: an N-terminal HLA-restricted peptide sequence (SRYWAIRTR, amino acids 1-9 of SEQ ID NO:387); followed by a first linker sequence (amino acids 10-19 of SEQ ID NO:387); followed by the human beta-2 microglobulin (β2m) sequence (amino acids 20-118 of SEQ ID NO:387); followed by a second linker sequence (amino acids 119-133 of SEQ ID NO:387); followed by the extracellular region of the HLA-B*2705 heavy chain (amino acids 134-409 of SEQ ID NO:387); and terminating with a myc-myc-hexahistidine C-terminal tag (amino acids 410-437 of SEQ ID NO:387).

Anti-HLA-B*27 antibodies were captured on either a polyclonal goat anti-human Fc-gamma-specific antibody (Jackson Lab, #109-005-098) or a monoclonal mouse anti-human Fc antibody (GE Healthcare, #BR-1008-39) surface created through direct amine coupling to a Biacore CM5 sensor chip. Different concentrations of scHLA-B27-mmH were injected over the monoclonal antibody captured surface for 4 minutes to determine the association rate, and dissociation was then monitored for 8 minutes. Temperature-dependent binding (Tables 4 and 5) was determined at 25° C. and 37° C. at a flow rate of 50 μl/min using HBST buffer (0.01 M HEPES pH7.4, 0.15M NaCl, 3 mM EDTA, 0.05% v/v surfactant P20). pH-dependent binding (Tables 2 and 3) was determined at the same flow rate in PBS buffer containing 0.05% v/v surfactant P20.

Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$ and $t_{1/2}$ (min)=[ln2/(60*$k_d$)]. Results are shown in Tables 2-5 (IC=inconclusive; NB=no binding).

TABLE 2

Kinetics of scHLA-B27-mmH Binding to Different Monoclonal Antibodies at 25° C. in PBS at pH 7.2

| mAb Captured | $k_a$ (1/Ms) | $k_d$ (1/s) | $K_D$ (M) | $t_{1/2}$ (min) |
|---|---|---|---|---|
| H4H2524P | 1.13E+05 | 7.85E−03 | 6.90E−08 | 1 |
| H4H2526P | 4.32E+04 | 3.32E−05 | 7.60E−10 | 348 |

TABLE 2-continued

Kinetics of scHLA-B27-mmH Binding to Different Monoclonal Antibodies at 25° C. in PBS at pH 7.2

| mAb Captured | $k_a$ (1/Ms) | $k_d$ (1/s) | $K_D$ (M) | $t_{1/2}$ (min) |
|---|---|---|---|---|
| H4H2528P | 2.80E+04 | 7.64E−05 | 2.71E−09 | 151 |
| H4H2530S | 3.98E+05 | 2.66E−04 | 6.68E−10 | 43 |
| H4H2532P | 4.86E+05 | 2.22E−04 | 4.57E−10 | 52 |
| H4H2534S | 3.46E+05 | 7.35E−04 | 2.13E−09 | 16 |
| H4H2538P | 4.50E+05 | 1.66E−04 | 3.70E−10 | 69 |
| H4H2542P | 9.70E+04 | 5.03E−03 | 5.21E−08 | 2 |
| H4H2555P | 4.97E+05 | 2.44E−04 | 4.91E−10 | 47 |
| H4H2559P | 4.07E+05 | 1.77E−04 | 4.34E−10 | 65 |
| H4H2560P | 5.80E+05 | 7.25E−04 | 1.25E−09 | 16 |
| H4H2562S | 9.15E+04 | 2.79E−03 | 3.05E−08 | 4 |
| H4H2564S | 6.67E+04 | 5.90E−04 | 8.84E−09 | 20 |
| H4H2477N2 | 1.30E+04 | 5.79E−04 | 4.40E−08 | 20 |
| H4H2480N | 2.01E+04 | 6.43E−04 | 3.20E−08 | 18 |
| H4H2482N2 | 3.88E+04 | 5.64E−03 | 1.45E−07 | 2 |
| H4H2490N2 | 2.50E+04 | 5.98E−03 | 2.39E−07 | 2 |
| H4H2491N | 5.43E+04 | 4.38E−04 | 8.06E−09 | 26 |
| H4H2497N | 2.28E+04 | 5.07E−04 | 2.23E−08 | 23 |
| H4H2499N | IC | IC | IC | IC |
| H4H2718N | 3.14E+04 | 3.05E−03 | 9.73E−08 | 4 |

TABLE 3

Kinetics of scHLA-B27-mmH Binding to Different Monoclonal Antibodies at 25° C. in PBS at pH 5.75

| mAb Captured | $k_a$ (1/Ms) | $k_d$ (1/s) | $K_D$ (M) | $t_{1/2}$ (min) |
|---|---|---|---|---|
| H4H2524P | 3.80E+04 | 7.68E−03 | 2.04E−07 | 2 |
| H4H2526P | 5.14E+04 | 3.84E−05 | 7.39E−10 | 301 |
| H4H2528P | 3.14E+04 | 8.57E−05 | 2.74E−09 | 135 |
| H4H2530S | 7.13E+04 | 7.62E−04 | 1.07E−08 | 15 |
| H4H2532P | 4.45E+05 | 3.20E−04 | 7.17E−10 | 36 |
| H4H2534S | 4.50E+05 | 2.40E−03 | 5.34E−08 | 5 |
| H4H2538P | 4.12E+05 | 2.64E−04 | 6.41E−10 | 44 |
| H4H2542P | 3.68E+04 | 1.80E−02 | 4.88E−07 | 1 |
| H4H2555P | 4.42E+05 | 3.78E−04 | 8.55E−10 | 31 |
| H4H2559P | 3.76E+05 | 2.71E−04 | 7.20E−10 | 43 |
| H4H2560P | 2.71E+05 | 2.09E−03 | 7.70E−09 | 6 |
| H4H2562S | 6.00E+04 | 5.71E−03 | 9.50E−08 | 2 |
| H4H2564S | 5.88E+04 | 4.40E−03 | 7.48E−08 | 3 |
| H4H2477N2 | 1.32E+04 | 2.11E−03 | 1.60E−07 | 5 |
| H4H2480N | 1.92E+04 | 2.47E−03 | 1.29E−07 | 5 |
| H4H2482N2 | 4.78E+04 | 6.76E−03 | 1.42E−07 | 2 |
| H4H2490N2 | 3.09E+04 | 7.33E−03 | 2.37E−07 | 2 |
| H4H2491N | 9.60E+04 | 2.76E−03 | 2.89E−08 | 4 |
| H4H2497N | 2.91E+04 | 9.88E−04 | 3.39E−08 | 12 |
| H4H2499N | IC | IC | IC | IC |
| H4H2718N | 3.28E+04 | 3.19E−03 | 9.75E−08 | 4 |

TABLE 4

Kinetics of scHLA-B27-mmH Binding to Different Monoclonal Antibodies at 25° C. in HBST at pH 7.4

| mAb Captured | $k_a$ (1/Ms) | $k_d$ (1/s) | $K_D$ (M) | $t_{1/2}$ (min) |
|---|---|---|---|---|
| H4H2524P | 2.16E+05 | 5.17E−03 | 2.39E−08 | 2 |
| H4H2526P | 5.75E+04 | 1.20E−04 | 2.08E−09 | 96 |
| H4H2528P | 2.50E+04 | 1.51E−04 | 6.00E−09 | 77 |
| H4H2530S | 5.78E+05 | 7.05E−04 | 1.22E−09 | 16 |
| H4H2532P | 1.23E+06 | 5.55E−04 | 4.52E−10 | 21 |
| H4H2534S | 3.47E+05 | 1.80E−03 | 5.18E−09 | 6 |
| H4H2538P | 9.70E+05 | 5.86E−04 | 6.04E−10 | 20 |
| H4H2542P | 9.00E+04 | 5.20E−03 | 5.80E−08 | 2 |
| H4H2555P | 1.25E+06 | 6.49E−04 | 5.21E−10 | 18 |
| H4H2559P | 6.85E+05 | 6.13E−04 | 8.95E−10 | 19 |
| H4H2560P | 1.22E+06 | 1.79E−03 | 1.47E−09 | 6 |
| H4H2562S | 2.48E+05 | 2.47E−03 | 1.00E−08 | 5 |
| H4H2564S | 1.69E+05 | 6.03E−04 | 3.57E−09 | 19 |
| H4H2477N | 6.50E+04 | 1.10E−03 | 1.69E−08 | 11 |

TABLE 4-continued

Kinetics of scHLA-B27-mmH Binding to Different Monoclonal Antibodies at 25° C. in HBST at pH 7.4

| mAb Captured | $k_a$ (1/Ms) | $k_d$ (1/s) | $K_D$ (M) | $t_{1/2}$ (min) |
|---|---|---|---|---|
| H4H2480N | 5.50E+04 | 1.32E−03 | 2.40E−08 | 9 |
| H4H2482N2 | 5.52E+04 | 6.60E−03 | 1.20E−07 | 2 |
| H4H2490N2 | 3.27E+04 | 8.46E−03 | 2.59E−07 | 1 |
| H4H2491N | 1.60E+05 | 2.87E−04 | 1.80E−09 | 40 |
| H4H2497N | 2.96E+04 | 9.95E−04 | 3.36E−08 | 12 |
| H4H2499N | 7.90E+04 | 1.68E−03 | 2.13E−08 | 7 |
| H4H2718N | 6.17E+04 | 2.77E−03 | 4.49E−08 | 4 |
| H4H2477N | NB | NB | NB | NB |
| H4H2482N | 4.71E+04 | 9.30E−03 | 1.97E−07 | 1.2 |
| H4H2490N | 3.53E+04 | 3.52E−04 | 9.97E−09 | 33 |

TABLE 5

Kinetics of scHLA-B27-mmH Binding to Different Monoclonal Antibodies at 37° C. in HBST at pH 7.4

| mAb Captured | $k_a$ (1/Ms) | $k_d$ (1/s) | $K_D$ (M) | $t_{1/2}$ (min) |
|---|---|---|---|---|
| H4H2524P | 2.06E+05 | 5.51E−03 | 2.68E−08 | 2 |
| H4H2526P | 8.05E+04 | 3.15E−04 | 3.91E−09 | 37 |
| H4H2528P | 3.34E+04 | 6.81E−04 | 2.04E−08 | 17 |
| H4H2530S | 9.51E+05 | 1.79E−03 | 1.88E−09 | 6 |
| H4H2532P | 1.48E+06 | 1.24E−03 | 8.37E−10 | 9 |
| H4H2534S | 4.52E+05 | 3.92E−03 | 8.70E−09 | 3 |
| H4H2538P | 1.23E+06 | 1.40E−03 | 1.13E−09 | 8 |
| H4H2542P | 4.40E+04 | 7.56E−03 | 1.70E−07 | 2 |
| H4H2555P | 1.60E+06 | 1.63E−03 | 1.02E−09 | 7 |
| H4H2559P | 1.19E+06 | 1.40E−03 | 1.18E−09 | 8 |
| H4H2560P | 1.36E+06 | 2.66E−03 | 1.96E−09 | 4 |
| H4H2562S | 3.79E+05 | 2.89E−03 | 7.63E−09 | 4 |
| H4H2564S | 1.89E+05 | 1.35E−03 | 7.17E−09 | 9 |
| H4H2477N2 | 8.70E+04 | 4.06E−03 | 4.70E−08 | 3 |
| H4H2480N | NB | NB | NB | NB |
| H4H2482N2 | 3.50E+04 | 1.50E−02 | 4.30E−07 | 1 |
| H4H2490N2 | 3.70E+04 | 1.31E−02 | 3.60E−07 | 1 |
| H4H2491N | 2.11E+05 | 4.78E−04 | 2.27E−09 | 24 |
| H4H2497N | 1.19E+04 | 4.01E−03 | 3.37E−07 | 3 |
| H4H2499N | 1.08E+05 | 3.00E−03 | 2.80E−08 | 4 |
| H4H2718N | 1.57E+05 | 4.58E−03 | 2.90E−08 | 3 |

At 25° C. in PBS at pH 7.2, 20 of 21 anti-HLA-B*27 antibodies bound scHLA-B27-mmH with $K_D$ values ranging from 370 μM to 239 nM as shown in Table 2. One antibody, H4H2499N, produced a low binding signal with kinetic data that could not be fit to standard models (IC).

At 25° C. in PBS at pH 5.75, 20 of 21 anti-HLA-B*27 antibodies bound scHLA-B27-mmH with $K_D$ values ranging from 641 pM to 488 nM as shown in Table 3. One antibody, H4H2499N produced a low binding signal with kinetic data that could not be fit to standard models (IC).

At 25° C. in HBST at pH 7.4, 23 of 24 anti-HLA-B*27 antibodies tested bound scHLA-B27-mmH with $K_D$ values ranging from 452 μM to 259 nM as shown in Table 4. One antibody, H4H2477N, did not bind scHLA-B27-mmH under these conditions (NB).

When tested at 37° C. in HBST at pH 7.4, 20 of the 21 anti-HLA-B*27 antibodies tested bound scHLA-B27-mmH with $K_D$ values ranging from 837 μM to 430 nM as shown in Table 5. One antibody, H4H2480N, did not bind to scHLA-B27-mmH under these conditions.

The ratio of $K_D$ values at pH 5.75 to $K_D$ values at pH 7.2 was calculated for each of the tested antibodies to assess the pH-dependent binding properties of the anti-HLA-B*27 antibodies (Table 6). As used herein, an anti-HLA-B*27 antibody exhibits "pH-dependent binding" if the antibody exhibits a higher level of binding (e.g., a lower $K_D$ value) at an increased pH value as compared to binding exhibited at lower pH value; this can be represented as a binding ratio (e.g., wherein the pH-dependent binding is demonstrated by a $K_D$ value at pH 5.75 that is at least 5-times greater than its $K_D$ value at pH 7.2 (as in Table 6 below).

TABLE 6 pH-Dependent Binding

| Antibody | $K_D$ (M) pH 7.2 | $K_D$ (M) pH 5.75 | Ratio $K_D$ @ 5.75/$K_D$ @ 7.2 |
|---|---|---|---|
| H4H2524P | 6.90E−08 | 2.04E−07 | 2.96 |
| H4H2526P | 7.60E−10 | 7.39E−10 | 0.97 |
| H4H2528P | 2.71E−09 | 2.74E−09 | 1.01 |
| H4H2530S | 6.68E−10 | 1.07E−08 | 16.02 |
| H4H2532P | 4.57E−10 | 7.17E−10 | 1.57 |
| H4H2534S | 2.13E−09 | 5.34E−08 | 25.07 |
| H4H2538P | 3.70E−10 | 6.41E−10 | 1.73 |
| H4H2542P | 5.21E−08 | 4.88E−07 | 9.37 |
| H4H2555P | 4.91E−10 | 8.55E−10 | 1.74 |
| H4H2559P | 4.34E−10 | 7.20E−10 | 1.66 |
| H4H2560P | 1.25E−09 | 7.70E−09 | 6.16 |
| H4H2562S | 3.05E−08 | 9.50E−08 | 3.11 |
| H4H2564S | 8.84E−09 | 7.48E−08 | 8.46 |
| H4H2477N2 | 4.40E−08 | 1.60E−07 | 3.64 |
| H4H2480N | 3.20E−08 | 1.29E−07 | 4.03 |
| H4H2482N2 | 1.45E−07 | 1.42E−07 | 0.98 |
| H4H2490N2 | 2.39E−07 | 2.37E−07 | 0.99 |
| H4H2491N | 8.06E−09 | 2.89E−08 | 3.59 |
| H4H2497N | 2.23E−08 | 3.39E−08 | 1.52 |
| H4H2499N | IC | IC | N/A |
| H4H2718N | 9.73E−08 | 9.75E−08 | 1.00 |

As shown in Table 6, the anti-HLA-B*27 antibodies of the present invention that exhibited pH-dependent binding according to the aforementioned definition are: H4H2530S, H4H2534S, H4H2542P, H4H2560P, and H4H2564S.

Example 4. Anti-HLA-B*27 Antibodies Block HLA-B*27-Induced T Cell Activation In Vitro A bioassay was developed to measure T cell activation induced by interaction between HLA-B*27-peptide complex and a corresponding T-cell receptor (TCR) by utilizing a mixed culture derived from two mammalian cell lines: C1R-neo (ATCC, #CRL-2369), a B-lymphoblastoid line previously shown to express low or no endogenous levels of HLA-A and HLA-B molecules; and Jurkat, a human CD4+ T cell line.

For the first component of the bioassay, the C1R-neo cell line was stably transfected to overexpress the heavy chain of the HLA-B*2705 allelic subvariant (amino acids 25-362 of SEQ ID NO:385) and human beta 2 microglobulin (β2m; amino acids 21-119 of SEQ ID NO:388) along with NP383-391, a nine amino acid HLA-B*27-restricted peptide (SRY-WAIRTR [SEQ ID NO:389]) derived from the nucleoprotein of influenza A virus. NP383-391 positive cells were sorted by FACS and a stable cell line was isolated (C1R-neo/HLA-B*2705/β2 m/NP383-391), which was maintained in Iscove's medium (Irvine Scientific, Cat. No. #9032) supplemented with 10% fetal bovine serum and penicillin/streptomycin/L-glutamine.

For the second component of the bioassay, a reporter cell line, Jurkat/NFAT-Luc (bearing an IL-2 responsive element coupled to luciferase expression [NFAT-luciferase]) was engineered to express: (1) GRb, a TCR consisting of two subunits, alpha (SEQ ID NO:390) and beta (SEQ ID NO:391), which were cloned from an HLA-B*27+ individual (the intact receptor, GRbAB, binds specifically the NP383-391 peptide in a complex with HLA-B*2705); and (2) the CD8 co-receptor, consisting of two subunits, alpha (SEQ ID NO:392), and beta (SEQ ID NO:393), which are required for the activation of class I-restricted TCR (normally expressed on CD8+ T cells). The resulting stable cell line (Jurkat/NFAT-Luc/CD8AB/GRbAB) was isolated and maintained in RPMI (Irvine Scientific, #9160) supplemented with 10% fetal bovine serum and penicillin/streptomycin/L-glutamine.

For the bioassay C1R-neo/HLA-B*2705/β2 m/NP383-391 cells were seeded into 96-well assay plates at 10,000 cells/well. To determine $10_{50}$ values, 1:3 serial dilutions of anti-HLA-B*27 antibodies starting from 100 nM down to 0.1 nM (plus a no antibody control) were added to cells and incubated for 1 hour at 37° C. in 5% $CO_2$. To stimulate the HLA-TCR interaction, 100,000 Jurkat/NFAT-Luc/CD8AB/GRbAB cells were added to each well and incubated for 5 hours at 37° C. in 5% $CO_2$. Luciferase activity was detected by adding OneGlo substrate (Promega, #E6051) reagent. Results are summarized in Table 7.

TABLE 7

Anti-HLA-B*27 antibody blocking of C1R-neo/HLA-B*2705/β2m/NP383-391 cell dependent stimulation of Jurkat/NFAT-Luc/CD8AB/GrbAB cells

| Antibody | $IC_{50}$ (M) |
|---|---|
| H4H2524P | 1.185E−09 |
| H4H2526P | 8.559E−11 |
| H4H2528P | 2.639E−10 |
| H4H2530S | 3.749E−10 |
| H4H2532P | 3.748E−10 |
| H4H2534S | 4.432E−10 |
| H4H2538P | 3.626E−10 |
| H4H2542P | 1.143E−10 |
| H4H2555P | 3.465E−10 |
| H4H2559P | 1.802E−10 |
| H4H2560P | 6.242E−10 |
| H4H2562S | blocks, not sigmoidal |
| H4H2564S | blocks, not sigmoidal |
| H4H2477N2 | strongly activates, not sigmoidal |
| H4H2480N | blocks, not sigmoidal |
| H4H2482N2 | blocks, not sigmoidal |
| H4H2490N2 | blocks, not sigmoidal |
| H4H2491N | no blocking |
| H4H2497N | 1.193E−10 |
| H4H2499N | 1.812E−08 |
| H4H2718N | blocks, not sigmoidal |
| Isotype control | no blocking |

As shown in Table 7, thirteen of the 21 anti-HLA antibodies tested in the mixed culture bioassay blocked C1R-Neo/HLA-B*2705/β2 m/NP383-391 cell dependent stimulation of Jurkat/NFAT-Luc/CD8AB/GrbAB cells with $10_{50}$ values ranging from 85.6 μM to 18.1 nM. Additionally, 6 of the 21 antibodies also blocked in the assay, but not in a sigmoidal manner. One antibody tested, H4H2477N[2], displayed strong activation in the mixed culture bioassay, but not in a sigmoidal manner.

Example 5. Flow Cytometric Analysis to Confirm Binding of Anti-HLA-B*27 Antibodies to Cells Expressing HLA-B*27

Flow cytometric analysis was utilized to confirm binding of anti-HLA-B*27 antibodies to HLA-B*27+ cells. Tested cells included: (a) the C1R-neo-B*2705 cell line; (b) splenocytes from HLA-B*27 transgenic mice; and (c) primary human peripheral blood mononuclear cells (PBMC) from HLA-B*27+ individuals. The C1R-neo-B*2705 cell line is a derivative of the parental C1R-neo cell line stably transfected to overexpress the heavy chain of the HLA-B*2705 allele and human beta 2 microglobulin (see Example 4). Parental non-transfected C1R-neo cells were used as a negative control. A transgenic mouse strain was generated by transgenic heterozygous expression of the heavy chain of HLA-B*2705 and human β2 microglobulin [C57BL/6J-Tg (HLA-B27) 30-4Trg mouse strain; stock #003440 from The Jackson Laboratory]. Splenocytes from wild type littermates were used as a negative control for the heterozygous HLA-B*27+ splenocytes. Primary human PBMCs were genotyped as positive for HLA-B*27, and expression of the HLA-B*27 allele was confirmed by staining with a commercial anti-HLA-B*27 antibody (HLA ABC Ab; Millipore #MAB1285F). PBMCs from HLA-B*27− donors were used as a negative control.

For experiments with mouse splenocytes, mice were sacrificed and spleens were removed and mechanically homogenized. Cell suspension was filtered and mononuclear cells were purified on a Histopaque gradient column. Human PBMC were purified from the white blood concentrate (Leukopak; New York Blood Bank, N.Y., #E3752V00) on a Histopaque gradient column.

For flow cytometric analysis, 100,000 cells were washed in stain buffer (eBioscience, #00-4222) and incubated with whole human IgG (10 μg/ml) (Jackson ImmunoResearch, #009-000-003) for 15 minutes at 4° C. to block Fc receptors on the cells. Next, anti-HLA-B*27 antibodies were added at indicated concentrations (0.1 or 1 μg/ml) and incubated for 30 minutes at 4° C. Cells were washed once and then incubated with secondary anti-human Fc antibody (1:2000 dilution) (Jackson ImmunoResearch, #709-116-149) for 20 minutes at 4° C. Cells were washed twice and fluorescence measurements were acquired using a FACSCalibur flow cytometer (BD Biosciences, MD) and analyzed by FlowJo software. Blocking with whole human IgG alone did not generate binding signal above background when detecting with secondary anti-hFc antibody. Results are summarized in Table 8 (WT=wild-type mouse; TG=HLA-B27/hβ2m transgenic mouse).

TABLE 8

FACS binding of anti-HLA antibodies to cells with differing HLA expression patterns Mean Fluorescence Intensity (MFI)

| | mouse splenocytes | | | C1R-neo cells | | primary PBMCs | |
| --- | --- | --- | --- | --- | --- | --- | --- |
| Antibody | WT (1 μg/ml) | TG (0.1 μg/ml) | TG (1 μg/ml) | C1R-neo (1 μg/ml) | C1R-neo-HLA-B27 (1 μg/ml) | B27(neg) (1 μg/ml) | B27(pos) (1 μg/ml) |
| H4H2477N2 | 30.0 | 107 | 336 | 13.2 | 53 | 91.6 | 102 |
| H4H2480N | 11.9 | 86.4 | 337 | 11 | 62.9 | 67.3 | 72.1 |
| H4H2482N2 | 13.5 | 250 | 360 | 4.82 | 141 | 42.1 | 76.6 |
| H4H2490N2 | 14.9 | 262 | 348 | 4.06 | 137 | 41.5 | 77.5 |
| H4H2491N | 6.0 | 27.4 | 60 | 2.53 | 12.8 | 26.6 | 35.8 |
| H4H2497N | 24.7 | 285 | 733 | 13.4 | 162 | 127 | 194 |
| H4H2499N | 15.4 | 170 | 378 | 1.75 | 89.4 | 9.13 | 51.4 |
| H4H2524P | 6.5 | 54.8 | 436 | 8.75 | 51.3 | 124 | 169 |
| H4H2526P | 8.6 | 86.7 | 758 | 33.7 | 146 | 185 | 252 |
| H4H2528P | 7.9 | 99.7 | 831 | 32.4 | 149 | 197 | 255 |
| H4H2530S | 8.0 | 65.8 | 512 | 17.9 | 78.8 | 158 | 196 |
| H4H2532P | 7.0 | 70.5 | 635 | 7.63 | 97.3 | 182 | 238 |
| H4H2534S | 6.8 | 75.3 | 555 | 15.9 | 64.9 | 144 | 186 |
| H4H2538P | 7.4 | 70.4 | 533 | 9.01 | 101 | 187 | 245 |
| H4H2542P | 7.8 | 115 | 884 | 2.02 | 117 | 73.4 | 170 |
| H4H2555P | 6.6 | 73.7 | 565 | 7.49 | 117 | 165 | 229 |
| H4H2559P | 8.9 | 54.6 | 498 | 8.47 | 104 | 182 | 230 |
| H4H2560P | 6.9 | 72.2 | 618 | 13.1 | 110 | 170 | 205 |
| H4H2562S | 6.2 | 47.6 | 290 | 2.24 | 31.1 | 50.2 | 66.6 |
| H4H2564S | 8.6 | 53.7 | 350 | 3.11 | 50.3 | 64.7 | 73.7 |
| H4H2718N | 9.3 | 55.6 | 215 | 3.84 | 36.5 | 43.2 | 63.8 |

As shown in Table 8, all of the tested anti-HLA-B*27 antibodies bound to HLA-B*27+ transgenic splenocytes, while no binding above background level was detected on splenocytes from wild type mice. Similarly, all antibodies bound C1R-neo-B*2705 cells. In parental C1R-neo cells, no binding above background level was detected for H4H2499N, H4H2542P and H4H2562P, while all the other antibodies showed various levels of binding above the background level, but lower than to C1R-neo-B*2705 cells. In human PBMC, all antibodies stained cells isolated from the blood of an individual confirmed to express the HLA-B*27 allele by genotyping ("B27(pos)"). When compared with binding to PBMC from an HLA-B*27 negative donor ("B27(neg)") the binding ratios ranged from 1.1 to 5.6, with H4H2499N exhibiting the highest specificity to the HLA-B*27+ PBMC.

Example 6. Binding of HLA-B*27 Antibodies to Peripheral Blood Mononuclear Cells (PBMC)

Additional flow cytometry experiments were conducted using PBMCs shown to express alleles other than HLA-B*27. Human blood from 4 donors was collected in K2-EDTA anti-coagulant tubes (BD, #366643). Genomic DNA was purified as per the manufacturer's specifications from whole blood samples using a QIAAMP DNA blood mini kit (Qiagen, #51304). Genomic DNA samples were then amplified, and the subsequent HLA locus-specific sequencing reaction was carried out using a SeCore kit (Invitrogen, locus A #5300925, locus B #5311925D, locus C #5320925). The DNA sequence was determined using an ABI 3730xL DNA Analyzer, and HLA type was determined using uType SBT HLA sequencing software (Invitrogen, #53999-1).

Human PBMCs were isolated from the blood of the same donors by Ficoll centrifugation. PBMCs were blocked with ChromPure Human IgG (Jackson Immunoresearch, #009-000-003), stained with 1 ug/ml of anti-HLA antibodies for 30 minutes at 4° C. followed by washing with staining buffer (BD Biosciences, #554657) and incubation with a 1:500 dilution of APC-labeled anti-human IgG secondary antibody (Jackson Immunoresearch, #109-136-098) for 20 minutes at 4° C. PBMCs were then washed, resuspended in stabilizing fixative (BD Biosciences, #338036) and sorted on a FACS Canto machine. Data were analyzed using FlowJo software.

The HLA Class I alleles determined from donors HD1, HD2, HD3, and HD4 are shown in Table 9. None of the 4 tested donors was determined to be HLA-B*27-positive.

rows of Table 10) show the least amount of binding to PBMCs from non-B*27 donors.

Example 7. Binding of HLA-B*27 Antibodies to Surface HLA*B

Flow cytometric analysis was further utilized to determine specificity of binding of anti-HLA antibodies to cell lines engineered to overexpress different HLA*B alleles. To generate cell lines expressing different HLA alleles, parental K562 (immortalized human myelogenous leukemia) cells were electroporated with DNA plasmids to promote stable integration of 23 different HLA alleles (shown in Table 11) as well as an antibiotic resistant gene to either neomycin or hygromycin. Electroporated cell lines were then placed under antibiotic selection for 2.5 to 5 weeks to select for cells expressing the specific HLA alleles. The resulting

TABLE 9

HLA Class I typing for 4 donor whole blood samples

| Donor Sample ID | HLA-A Locus | | HLA-B Locus | | HLA-C Locus | |
|---|---|---|---|---|---|---|
| | Allele 1 | Allele 2 | Allele 1 | Allele 2 | Allele 1 | Allele 2 |
| D2-1 (HD1) | *11:01:01 | *24:03:01 | *15:01:01:01 | *18:01:01:01 | *03:03:01 | *12:03:01:01 |
| D4-1 (HD4) | *24:02:01 | *33:03:01 | *40:06:01:01 | *58:01:01 | *03:02:01 | *15:02:01 |
| D3* (HD3) | *03:01:01:01 | *26:01:01 | *07:02:01 | *38:01:01 | *07:02:01:01 | *12:03:01:01 |
| D3-5 (HD2) | *02:01:01:01 | *36:01 | *14:02:01 | *53:01:01 | *04:01:01:01 | *08:02:01 |

The binding of anti-HLA antibodies to PBMCs of the HLA-typed donors, as determined by flow cytometry, is shown in Table 10.

TABLE 10

FACS binding of anti-HLA antibodies to PBMCs from 4 donors

| Antibody | HD1 | HD2 | HD3 | HD4 |
|---|---|---|---|---|
| Unstained | 3.13 | 3.02 | 3.02 | 3.71 |
| anti-human Fc secondary | 13.8 | 28.4 | 18.2 | 15 |
| H4H2524P | 460 | 685 | 703 | 206 |
| H4H2526P | 690 | 1059 | 1156 | 518 |
| H4H2528P | 633 | 959 | 1143 | 635 |
| H4H2530S | 637 | 756 | 995 | 455 |
| H4H2532P | 626 | 675 | 955 | 557 |
| H4H2534S | 327 | 52.1 | 1010 | 372 |
| H4H2538P | 580 | 41.7 | 1032 | 430 |
| H4H2542P | 791 | 35.4 | 830 | 742 |
| H4H2555P | 435 | 35.4 | 1065 | 532 |
| H4H2560P | 378 | 771 | 1125 | 382 |
| H4H2562S | 235 | 453 | 980 | 171 |
| H4H2564S | 404 | 560 | 876 | 278 |
| H4H2477N2 | 704 | 868 | 1374 | 680 |
| H4H2480N | 454 | 513 | 985 | 397 |
| H4H2482N2 | 573 | 1206 | 1108 | 624 |
| H4H2490N2 | 391 | 1078 | 918 | 640 |
| H4H2491N | 438 | 783 | 754 | 388 |
| H4H2497N | 281 | 1097 | 1073 | 621 |
| H4H2499N | 162 | 315 | 424 | 219 |
| H4H2718N | 96.6 | 210 | 282 | 56.6 |

As shown in Table 10, all of the anti-HLA antibodies bound to the PBMCs of all donors to some extent, except antibodies H4H2534S, H4H2538P, H4H2542P and H4H2555P, which did not bind to PBMCs from the HD2 donor. Antibodies H4H2499N and H4H2718N (last two K562/HLA cell lines were FACS sorted for populations with the highest levels of surface HLA (top 10% of expressers) using an HLA-A, B, C pan-specific antibody (clone W6/32) conjugated to phycoerythrin (Biolegend, #311406).

TABLE 11

HLA-B alleles used in the generation of HLA-B expressing K562 cell lines

| HLA*B Alleles Expressed | IMGT HLA Accession Number |
|---|---|
| B*07:02:01 | HLA00132 |
| B*08:01:01 | HLA00146 |
| B*13:01:01 | HLA00152 |
| B*14:02:01 | HLA00158 |
| B*15:01:01:01 | HLA00162 |
| B*18:01:01:01 | HLA00213 |
| B*27:05:02 | HLA00225 |
| B*27:09 | HLA00230 |
| B*35:01:01:01 | HLA00237 |
| B*37:01:01 | HLA00265 |
| B*38:02:01 | HLA00268 |
| B*39:01:01:01 | HLA00271 |
| B*40:01:01 | HLA00291 |
| B*42:01:01 | HLA00315 |
| B*44:03:01 | HLA00319 |
| B*45:01 | HLA00329 |
| B*46:01:01 | HLA00331 |
| B*48:01:01 | HLA00335 |
| B*49:01:01 | HLA00340 |
| B*50:01:01 | HLA00341 |
| B*52:01:01:01 | HLA00362 |
| B*53:01:01 | HLA00364 |
| B*54:01:01 | HLA00367 |

To perform the flow cytometric analysis, ~2×10$^5$ cells/well were washed in 200 uL of Stain Buffer (BSA) (BD Pharmingen, #554657), and blocked with 1 ug/mL of purified human IgG (Jackson ImmunoResearch, #009-000-003) for 15 minutes at room temperature. Next, anti-HLA antibodies were added at 1 μg/mL and incubated for 30 minutes at 4° C. Cells were washed twice with Stain Buffer and then incubated with a goat polyclonal F(ab')2 secondary reagent conjugated to allophycocyanin that is specific for human IgG Fc-gamma fragment (Jackson ImmunoResearch, #109-136-098) at 1:500 dilution for 20 minutes at 4° C. Cells were washed twice with 200 uL and fluorescence measurements were acquired using a FACSCanto II instrument (BD Biosciences, MD) and analyzed using FlowJo software (Tree Star).

Results for the 20 anti-HLA antibodies binding to the K562 cell lines expressing different HLA-B alleles shown as ratio of MFI signal relative to that of the parental K562 cell lines are shown in Tables 12, 13, and 14, below. Of the 20 antibodies tested, H4H2499N exhibited the highest degree of specificity.

TABLE 12

FACS binding of anti-HLA antibodies to K562 cells expressing seven different HLA-B alleles

| K652 | Parental MFI Value | Ratio of MFI relative to parental | | | | | | |
|---|---|---|---|---|---|---|---|---|
| | | HLA-B*27:05:02 | HLA-B*35:01:01:01 | HLA-B*44:03:01 | HLA-B*38:02:01 | HLA-B*39:01:01:01 | HLA-B*40:01:01 | HLA-B*42:01:01 |
| Unstained | 25 | 0.7 | 1.2 | 1.0 | 1.4 | 8.6 | 1.1 | 1.2 |
| ahFc secondary | 147 | 0.7 | 0.6 | 0.8 | 1.2 | 0.8 | 0.7 | 1.1 |
| H4H2524P | 232 | 11.1 | 22.1 | 12.9 | 5.7 | 2.5 | 5.2 | 14.0 |
| H4H2526P | 328 | 10.6 | 23.3 | 10.7 | 6.2 | 3.8 | 6.1 | 13.4 |
| H4H2528P | 334 | 11.7 | 22.1 | 9.5 | 6.3 | 4.1 | 6.1 | 14.0 |
| H4H2530S | 334 | 7.8 | 20.1 | 12.0 | 4.6 | 3.3 | 4.6 | 10.6 |
| H4H2532P | 309 | 8.6 | 15.7 | 10.2 | 6.0 | 4.0 | 5.1 | 10.2 |
| H4H2534S | 321 | 8.8 | 20.3 | 9.2 | 4.7 | 3.1 | 4.3 | 11.7 |
| H4H2538P | 327 | 8.9 | 20.7 | 9.3 | 6.7 | 3.9 | 5.5 | 13.5 |
| H4H2542P | 234 | 9.7 | 4.3 | 10.0 | 9.6 | 1.4 | 0.9 | 6.4 |
| H4H2555P | 301 | 10.7 | 20.3 | 10.8 | 6.9 | 4.3 | 5.7 | 13.6 |
| H4H2559P | 289 | 6.7 | 16.5 | 7.8 | 7.2 | 4.4 | 5.5 | 14.6 |
| H4H2560P | 295 | 10.2 | 21.0 | 11.7 | 0.7 | 3.1 | 6.3 | 13.2 |
| H4H2562S | 238 | 7.5 | 9.7 | 7.8 | 3.5 | 2.1 | 3.3 | 9.7 |
| H4H2564S | 267 | 8.7 | 13.0 | 8.5 | 3.9 | 2.2 | 3.3 | 11.6 |
| H4H2477N2 | 236 | 10.6 | 17.0 | 10.2 | 5.7 | 2.8 | 0.7 | 1.9 |
| H4H2480N | 237 | 9.6 | 15.3 | 8.5 | 5.9 | 3.2 | 1.0 | 3.3 |
| H4H2482N2 | 235 | 12.5 | 24.8 | 17.7 | 4.3 | 2.4 | 1.3 | 4.2 |
| H4H2490N2 | 237 | 13.5 | 23.5 | 17.1 | 3.4 | 2.0 | 1.1 | 4.2 |
| H4H2497N | 252 | 13.7 | 24.2 | 8.7 | 6.7 | 4.0 | 5.8 | 17.6 |
| H4H2499N | 209 | 9.8 | 0.9 | 13.1 | 3.7 | 0.8 | 0.6 | 1.0 |
| H4H2718N | 225 | 7.0 | 11.8 | 6.3 | 3.2 | 1.7 | 2.2 | 9.7 |

TABLE 13

FACS binding of anti-HLA antibodies to K562 cells expressing six different HLA-B alleles

| K652 | Parental MFI Value | Ratio of MFI relative to parental | | | | | |
|---|---|---|---|---|---|---|---|
| | | HLA-B* 07:02:01 | HLA-B* 37:01:01 | HLA-B* 08:01:01 | HLA-B* 15:01:01:01 | HLA-B* 45:01 | HLA-B* 46:01:01 |
| Unstained | 33.7 | 0.8 | 0.8 | 0.8 | 0.8 | 1.1 | 1.2 |
| ahFc secondary | 83.4 | 3.4 | 3.4 | 1.6 | 1.3 | 1.5 | 1.1 |
| H4H2524P | 108 | 81.2 | 28.5 | 31.1 | 27.5 | 24.6 | 18.3 |
| H4H2526P | 200 | 57.9 | 25.7 | 28.6 | 29.7 | 20.4 | 16.7 |
| H4H2528P | 206 | 53.4 | 25.0 | 26.0 | 28.7 | 24.3 | 16.7 |
| H4H2530S | 190 | 53.0 | 22.4 | 23.2 | 23.0 | 18.6 | 16.1 |
| H4H2532P | 155 | 70.8 | 26.6 | 33.0 | 28.4 | 22.5 | 20.5 |
| H4H2534S | 168 | 57.6 | 21.4 | 25.3 | 23.5 | 20.2 | 16.4 |
| H4H2538P | 158 | 69.3 | 28.7 | 31.1 | 31.0 | 26.0 | 21.2 |
| H4H2542P | 89.5 | 22.7 | 49.2 | 11.5 | 9.3 | 10.1 | 3.9 |
| H4H2555P | 156 | 61.8 | 24.4 | 34.0 | 30.8 | 23.2 | 19.7 |
| H4H2559P | 151 | 63.8 | 29.5 | 35.2 | 31.8 | 25.0 | 20.4 |
| H4H2560P | 99.9 | 68.9 | 34.5 | 30.6 | 28.5 | 27.0 | 25.8 |
| H4H2562S | 109 | 56.0 | 25.4 | 20.7 | 20.8 | 18.0 | 11.8 |
| H4H2564S | 95.8 | 69.2 | 28.3 | 27.0 | 25.5 | 19.8 | 16.2 |
| H4H2477N2 | 110 | 3.9 | 21.4 | 3.1 | 23.4 | 13.7 | 13.3 |
| H4H2480N | 110 | 10.1 | 26.2 | 5.6 | 26.9 | 15.0 | 15.9 |
| H4H2482N2 | 118 | 10.0 | 16.4 | 6.0 | 25.9 | 21.3 | 11.6 |
| H4H2490N2 | 100 | 14.2 | 20.5 | 8.1 | 30.9 | 25.0 | 14.6 |
| H4H2497N | 121 | 59.5 | 35.5 | 28.1 | 37.9 | 28.3 | 20.8 |

TABLE 13-continued

FACS binding of anti-HLA antibodies to K562 cells expressing six different HLA-B alleles

| | K652 Parental MFI Value | Ratio of MFI relative to parental | | | | | |
|---|---|---|---|---|---|---|---|
| | | HLA-B* 07:02:01 | HLA-B* 37:01:01 | HLA-B* 08:01:01 | HLA-B* 15:01:01:01 | HLA-B* 45:01 | HLA-B* 46:01:01 |
| H4H2499N | 85.1 | 1.5 | 29.1 | 1.9 | 1.4 | 1.4 | 1.3 |
| H4H2718N | 109 | 45.7 | 20.7 | 17.7 | 18.4 | 14.1 | 10.6 |

TABLE 14

FACS binding of anti-HLA antibodies to K562 cells expressing ten different HLA-B alleles

| | K652 Parental MFI Value | Ratio of MFI relative to parental | | | | | | | | | |
|---|---|---|---|---|---|---|---|---|---|---|---|
| | | HLA-B*13: 01:01 | HLA-B*14: 02:01 | HLA-B*18: 01:01:01 | HLA-B*27: 09 | HLA-B*48: 01:01 | HLA-B*49: 01:01 | HLA-B*50: 01:01 | HLA-B*52: 01:01:01 | HLA-B*53: 01:01 | HLA-B*54: 01:01 |
| unstained | 73.1 | 0.9 | 1.1 | 0.9 | 1.0 | 1.4 | 1.1 | 0.9 | 0.9 | 1.0 | 1.0 |
| ahFc secondary | 80 | 1.9 | 1.3 | 2.1 | 2.1 | 1.9 | 2.2 | 1.8 | 1.8 | 1.5 | 1.4 |
| H4H2524P | 95.7 | 5.4 | 3.8 | 5.3 | 9.7 | 5.8 | 3.2 | 3.7 | 4.1 | 4.6 | 3.2 |
| H4H2526P | 108 | 6.7 | 4.7 | 8.3 | 14.9 | 6.9 | 3.5 | 4.4 | 5.1 | 5.9 | 4.6 |
| H4H2528P | 104 | 5.4 | 4.3 | 7.0 | 16.5 | 11.6 | 3.8 | 7.2 | 8.2 | 6.0 | 4.9 |
| H4H2530S | 84.8 | 10.2 | 4.4 | 12.2 | 15.4 | 5.5 | 3.8 | 4.6 | 4.1 | 4.8 | 3.5 |
| H4H2532P | 88.5 | 7.7 | 4.5 | 6.9 | 14.8 | 9.1 | 3.4 | 4.8 | 5.5 | 6.8 | 4.6 |
| H4H2534S | 89 | 5.1 | 3.6 | 10.8 | 12.6 | 8.8 | 5.4 | 4.9 | 5.9 | 6.7 | 4.3 |
| H4H2538P | 99.4 | 8.5 | 5.5 | 9.5 | 12.7 | 7.8 | 2.8 | 4.3 | 6.3 | 6.5 | 5.0 |
| H4H2542P | 82.7 | 2.9 | 1.7 | 5.3 | 17.7 | 3.7 | 3.9 | 4.2 | 7.0 | 8.7 | 3.4 |
| H4H2555P | 89.1 | 9.0 | 5.1 | 10.4 | 13.2 | 9.0 | 3.5 | 6.1 | 6.5 | 6.9 | 5.2 |
| H4H2559P | 87.4 | 9.6 | 5.2 | 8.9 | 11.4 | 9.8 | 3.2 | 7.1 | 7.6 | 7.9 | 5.8 |
| H4H2560P | 89.8 | 10.0 | 5.1 | 7.4 | 13.7 | 9.0 | 5.0 | 6.1 | 6.0 | 6.4 | 5.3 |
| H4H2562S | 89.3 | 5.9 | 3.0 | 6.5 | 8.6 | 5.0 | 4.4 | 4.7 | 3.7 | 3.2 | 3.5 |
| H4H2564S | 95.7 | 4.4 | 2.1 | 6.0 | 8.0 | 2.7 | 3.2 | 3.4 | 3.5 | 3.1 | 2.3 |
| H4H2477N2 | 98.2 | 5.2 | 2.6 | 6.5 | 8.4 | 1.8 | 4.3 | 3.2 | 4.0 | 4.4 | 2.6 |
| H4H2480N | 96.3 | 4.5 | 1.8 | 4.4 | 7.4 | 1.7 | 2.6 | 2.0 | 2.6 | 2.2 | 1.6 |
| H4H2482N2 | 88.2 | 6.5 | 4.4 | 6.7 | 9.6 | 8.3 | 4.5 | 5.7 | 8.6 | 7.0 | 4.9 |
| H4H2490N2 | 94.9 | 6.7 | 2.8 | 6.3 | 12.1 | 4.8 | 4.4 | 5.2 | 6.8 | 5.9 | 3.4 |
| H4H2497N | 92.4 | 7.7 | 3.9 | 6.9 | 11.6 | 7.3 | 4.0 | 5.4 | 6.6 | 5.2 | 4.1 |
| H4H2499N | 85.9 | 8.3 | 1.2 | 1.9 | 13.7 | 1.6 | 4.1 | 1.7 | 6.5 | 3.5 | 1.2 |
| H4H2718N | 87.3 | 5.6 | 1.8 | 6.9 | 7.7 | 4.8 | 4.4 | 3.3 | 4.3 | 3.0 | 2.1 |

Example 8. Preferential Binding of Antibodies to HLA-B*27 Allelic Subvariants

The ability of anti-HLA-B*27 antibodies to bind to cell-surface human HLA-B*27 allelic subvariants (i.e., HLA-B*2705 and HLA-B*2709), as compared to their ability to bind the HLA-B*07 allelic variant, was measured using electrochemiluminescence detection technology. For these studies C1R-neo cells stably transfected to express either HLA-B*07 heavy chain (CR1-B7, ATCC #CRL-2371), HLA-B*2705 heavy chain (amino acids 25-362 of SEQ ID NO:385), or HLA-B*2709 heavy chain (amino acids 25-362 of SEQ ID NO:386), were used. Each of the HLA-B* expressing cell lines also expressed human beta 2 microglobulin (β2m; amino acids 21-119 of SEQ ID NO:388) which forms a non-covalent complex with HLA heavy chain.

Cells were harvested and counted using a Cellometer™ Auto T4 cell counter (Nexcelom Bioscience). Approximately 20,000 cells per well were seeded in PBS into carbon electrode plates (Meso Scale Discovery, #L15-XB-3/L11XB-3) and then incubated for 1 hour at 37° C. After blocking with PBS+2% (w/v) BSA for 1 hour at 25° C., either 1 nM or 1.1 nM of anti-HLA-B*27 antibodies was transferred to plate-bound cells and incubated for 1 hour at 25° C. Unbound antibodies were washed off using an AquaMax2000 plate washer (MDS Analytical Technologies). Cell-bound anti-HLA-B*27 antibodies were detected with either anti-mFc (Jackson ImmunoResearch, #115-005-164) or anti-hFc (Meso Scale Discovery, #R32AJ-1) antibodies conjugated with SULFO-TAG™. For the cell binding measurement, MSD Read Buffer (Meso Scale Discovery, #R92TD-2) was added to the cell-antibody mixture and allowed to incubate for 15 minutes at room temperature before electrochemical stimulation. Luminescence was detected using a SECTOR Imager 6000 reader (MSD) using a 620 nm wavelength filter. The luminescence intensity correlates with the amount of antibodies bound to cells. Specificity ratios of anti-HLA-B*27 antibodies binding either C1R-B*07, C1R-neo B*2705 or C1R-neo B*2709 cells, relative to C1R-neo parental cells, are shown in Table 15. (−) indicates ratios from 1 to 3 fold above binding to C1R-neo cells; (+) indicates ratios from 3 to 10 fold above binding to C1R-neo cells; (++) indicates ratios from 10 to 50 fold above binding to C1R-neo cells; and (+++) indicates ratios greater than 50 fold above binding to C1R-neo cells.

TABLE 15

Relative Ratios of Antibody Binding to Cells Expressing
HLA-B* Alleles to Antibody Binding to Parental Cells

| | Cell Line | | |
|---|---|---|---|
| Antibody | C1R B*7 | C1R-neo B*2705 | C1R-neo B*2709 |
| H1M2477N | + | ++ | ++ |
| H1M2480N | + | ++ | ++ |
| H2aM2482N | ++ | +++ | +++ |
| H1M2490N | − | ++ | ++ |
| H2bM2491N | + | + | + |
| H1M2497N | + | ++ | + |
| H2aM2499N | − | +++ | +++ |
| H2bM2718N | + | ++ | + |
| H4H2524P | + | ++ | ++ |
| H4H2526P | + | ++ | ++ |
| H4H2528P | + | ++ | ++ |
| H4H2530S | + | ++ | + |
| H4H2532P | + | ++ | ++ |
| H4H2534S | + | ++ | + |
| H4H2538P | + | ++ | ++ |
| H4H2542P | + | +++ | ++ |
| H4H2555P | + | ++ | ++ |
| H4H2559P | + | ++ | ++ |
| H4H2560P | + | ++ | + |
| H4H2562S | + | ++ | ++ |
| H4H2564S | + | + | + |

As shown in Table 15, only H2aM2482N exhibited significant binding to cells expressing the HLA-B*07 allele (with a specificity ratio of from 10- to 50-fold above binding to C1R-neo cells). Antibodies H1M2477N, H1M2480N, H2aM2482N, H1M2490N, H2aM2499N, H4H2524P, H4H2526P, H4H2528P, H4H2532P, H4H2538P, H4H2555P, H4H2559P, and H4H2562S exhibited approximately equivalent binding to cells expressing the HLA-B*2705 allelic variant as to cells expressing the HLA-B*2709 allelic variant. On the other hand, certain exemplary antibodies exhibited relatively stronger binding to cells expressing the HLA-B*2705 allele as compared to cells expressing the HLA-B*2709 allele (e.g., H1M2497N, H2bM2718N, H4H2530S, H4H2534S, H4H2542P, and H4H2560P).

All of the antibodies tested, except for H2bM2491N and H4H2564S, exhibited enhanced binding to cells expressing the HLA-B*2705 and/or HLA-B*2709 allelic subvariants compared to cells expressing the HLA-B*07 allelic variant. Antibody H2aM2499N, for example, showed at least 50-fold greater binding to cells expressing HLA-B*2705 and HLA-B*2709 allelic subvariants above binding to C1R-neo cells (represented by [+++] in Table 15), and less than 3-fold greater binding to cells expressing the HLA-B*07 allelic variant above binding to C1R-neo cells (represented by [−] in Table 15). Similar, but less pronounced, enhanced binding characteristics were observed with several other exemplary anti-HLA-B*27 antibodies tested in this Example, as shown in Table 15.

Example 9. Activity of Anti-HLA-B*27 Antibodies Evaluated In Vivo

The activity of anti-HLA-B*27 antibodies in vivo was investigated. HLA-B*27 (amino acids 25-362 of UniProt accession number P0$_{3989}$) and human beta 2 microglobulin (β2m; amino acids 21-119 of GenBank accession number NP_004039) were overexpressed in the liver of C57BL/6 wild type (WT) mice obtained from Jackson Laboratory by hydrodynamic delivery of DNA (HDD). For the HDD experiment, WT mice were divided into groups of 2-5 mice per cohort, and each mouse was injected with either 50 μg of plasmid expressing HLA-B*27 plus 50 μg of plasmid expressing β2m or with 50 μg of an empty plasmid control. At days 3 and 10 post-HDD injection, mice in each of four cohorts were intra-peritoneally injected with 30 mg/kg of anti-HLA antibodies H4H2542P, H4H2499N or H4H2482P, or an isotype control antibody. Mice were sacrificed on day 14 post-HDD, and cells infiltrating the liver were isolated by collagenase treatment and percoll centrifugation. Liver red blood cells were lysed using ACK lysis buffer (Gibco, #A1492-01). Infiltrating immune cells were stained with a live/dead cell dye (Invitrogen, #L34957) as well as an anti-CD45 antibody (eBioscience, #12-0451-82) to detect infiltrating leukocytes and anti-CD3 (BD Biosciences, #552774), anti-CD4 (Biolegend, #100414) and anti-CD8 (Biolegend, #100734) antibodies to identify different T cell populations. Flow cytometry was performed on a FACS Canto and data were analyzed using FlowJo software. Levels of infiltration of immune cells generally, and CD8$^+$ and CD4$^+$ cells in particular, into livers of sacrificed animals were measured in terms of frequency, i.e., the percentage of intact/live cells from livers isolated with collagenase treatment and percoll centrifugation that were lymphocytes, CD8$^+$ cells, or CD4$^+$ cells (as opposed to, e.g., hepatocytes).

The frequency of live cells in the lymphocyte gate (Table 16) as well as frequencies of CD8$^+$ (Table 17) and CD4$^+$ (Table 18) T cells infiltrating the liver were analyzed by flow cytometry. Mice injected with control plasmids showed a frequency of about 10% immune cells and 1% of CD8$^+$ and CD4$^+$ T cells infiltrating the liver, regardless of antibody treatment. In contrast, overexpression of HLA-B*27 and β2m led to an increase in the frequency of immune cell infiltrates (mean=27%) including an increase in CD8$^+$ and CD4$^+$ T cells (6.1% and 3.3%, respectively) in mice treated with isotype control antibody. Treatment of HLA-B*27/β2m-expressing mice with the anti-HLA antibodies, H4H25422P and H4H2499N, led to a significant reduction in liver-infiltrating immune cells. This was most prominent in mice treated with H4H2499N, which also resulted in a significant decrease in the percentage of CD8$^+$ and CD4$^+$ T cells. In contrast, the anti-HLA antibody H4H2482P and the isotype control had no significant reduction on infiltration of immune cells into the liver. Therefore, the anti-HLA antibody H4H2499N is able to block infiltration of inflammatory cells into the liver of mice overexpressing HLA-B*27 and β2m by HDD.

TABLE 16

| Frequency of live infiltrating immune cells | | | | | | | | |
|---|---|---|---|---|---|---|---|---|
| treatment | H4H2542P | | H4H2499N | | H4H2482P | | Isotype control | |
| HDD plasmid | B27/β2m | control | B27/β2m | control | B27/β2m | control | β2m | control |
| | 17.1 | 14.2 | 8.68 | 15.3 | 19.3 | 7.55 | B27/22.5 | 5.94 |
| | 18.1 | 9.91 | 8.8 | 6.67 | 22.8 | 10.8 | 34 | 11.5 |
| | 12.7 | | 5.63 | | 13.7 | | 28.6 | |

TABLE 16-continued

Frequency of live infiltrating immune cells

| treatment | H4H2542P | | H4H2499N | | H4H2482P | | Isotype control | |
|---|---|---|---|---|---|---|---|---|
| HDD plasmid | B27/β2m | control | B27/β2m | control | B27/β2m | control | β2m | control |
| | 10.9 | | 10.7 | | 23.3 | | 23.5 | |
| | 23.7 | | 9.35 | | 21.5 | | | |
| mean | 16.5 | 12.06 | 8.632 | 10.99 | 20.12 | 9.175 | 27.15 | 8.72 |
| SEM | 2.242 | 2.145 | 0.8317 | 4.315 | 1.748 | 1.625 | 2.645 | 2.78 |
| p value | 0.0175 | | 0.0002 | | NS | | — | |

TABLE 17

Frequency of total CD8+ T cells in liver

| treatment | H4H2542P | | H4H2499N | | H4H2482P | | Isotype control | |
|---|---|---|---|---|---|---|---|---|
| HDD plasmid | B27/β2m | control | B27/β2m | control | B27/β2m | control | B27/β2m | control |
| | 3.55 | 1.95 | 2.44 | 1.6 | 4.22 | 0.72 | 5.06 | 0.674 |
| | 4.12 | 1.22 | 2.13 | 0.61 | 5.7 | 1.08 | 7.43 | 1.2 |
| | 3.14 | | 1.11 | | 3.34 | | 6.84 | |
| | 3.45 | | 2.49 | | 6.35 | | 5.19 | |
| | 6.75 | | 2.31 | | 5.57 | | | |
| mean | 4.202 | 1.585 | 2.096 | 1.105 | 5.036 | 0.9 | 6.13 | 0.937 |
| SEM | 0.6564 | 0.365 | 0.2542 | 0.495 | 0.5475 | 0.18 | 0.5932 | 0.263 |
| p value | NS | | 0.0003 | | NS | | — | |

TABLE 18

Frequency of total CD4+ T cells in liver

| treatment | H4H2542P | | H4H2499N | | H4H2482P | | Isotype control | |
|---|---|---|---|---|---|---|---|---|
| HDD plasmid | B27/β2m | control | B27/β2m | control | B27/β2m | control | B27/β2m | control |
| | 1.87 | 1.34 | 1.14 | 1.59 | 2.7 | 0.716 | 2.56 | 0.612 |
| | 2.6 | 1.18 | 1.29 | 0.586 | 3.25 | 1.17 | 4.59 | 1.12 |
| | 1.61 | | 0.762 | | 3.34 | | 2.9 | |
| | 1.44 | | 1.57 | | 2.92 | | 3.33 | |
| | 3.17 | | 1.58 | | 2.85 | | | |
| mean | 2.138 | 1.26 | 1.268 | 1.088 | 3.012 | 0.943 | 3.345 | 0.866 |
| SEM | 0.3253 | 0.08 | 0.1519 | 0.502 | 0.1217 | 0.227 | 0.4439 | 0.254 |
| p value | NS | | 0.0018 | | NS | | — | |

Example 10. Construction of Histidine Substitution Variant Anti-HLA-B*27 Antibodies In an attempt to generate variants of anti-HLA-B*27 antibodies with pH-dependent binding properties (i.e., reduced binding at low pH as compared to neutral pH) and improved in vivo efficacy (e.g., longer antibody serum half-life, prolonged inhibition of T-cell activation, etc.), a series of variant antibodies was constructed. In particular, mutant versions of the parental antibodies H4H2477N2 and H4H2499N were constructed in which each (non-histidine) amino acid within the complementarity determining regions (CDRs) of each antibody was individually mutated to histidine. As shown in Table 1, the heavy chain variable region (HCVR) of the parental H4H2477N2 antibody comprises the amino acid sequence of SEQ ID NO:50 and the light chain variable region (LCVR) of the parental H4H2477N2 antibody comprises the amino acid sequence of SEQ ID NO:58 the heavy chain variable region (HCVR) of the parental H4H2499N antibody comprises the amino acid sequence of SEQ ID NO:146 and the light chain variable region (LCVR) of the parental H4H2499N antibody comprises the amino acid sequence of SEQ ID NO:154; The CDR sequences of the parental H4H2477N2 and H4H2499N antibodies are depicted in Tables 19A and 19B, respectively.

TABLE 19A

CDR Sequences of mAb H4H2477N2

| CDR | Amino Acid Sequence | SEQ ID NO: |
|---|---|---|
| HCDR1 | GGSFSDYY | 52 |
| HCDR2 | INHRGNT | 54 |
| HCDR3 | ARIQLWLRGYDYYGMDV | 56 |
| LCDR1 | QGIRND | 60 |
| LCDR2 | AAS | 62 |
| LCDR3 | LQHNTYPWT | 64 |

TABLE 19B

CDR Sequences of mAb H4H2499N

| CDR | Amino Acid Sequence | SEQ ID NO: |
| --- | --- | --- |
| HCDR1 | GFTFSDYY | 148 |
| HCDR2 | ISTSGSTI | 150 |
| HCDR3 | LLHYYYGMDV | 152 |
| LCDR1 | QSVSSY | 156 |
| LCDR2 | DAS | 158 |
| LCDR3 | QQRSNWPWT | 160 |

Forty-eight individual histidine substitution variants of H4H2477N2 were made (31 heavy chain CDR mutants and 17 light chain CDR mutants); and 43 individual histidine substitution variants of H4H2499N were made (25 heavy chain CDR mutants and 18 light chain CDR mutants). Variant antibodies obtained from culture medium (supernatant) after transient expression in Chinese hamster ovary (CHO) cells were screened for pH-dependent binding, i.e., reduced binding to cells expressing HLA-B*27 at acidic pH as compared to neutral pH. Based on the initial supernatant screening, several variant antibodies comprising single and multiple histidine substitutions in the CDRs were selected for further study, as summarized in Table 20. The His-substitution designations shown in Table 20 (e.g., "Y33H", "N52H", etc. for H4H2477N2; and "Y32H", "T53H", etc. for H4H2499N) relate to the heavy and light chain variable region (HCVR/LCVR) amino acid sequences of H4H2477N2 (i.e., SEQ ID NOs: 50/58) and H4H2499N (i.e., SEQ ID NOs:146/154). An empty cell in Table 20 denotes the parental sequence.

TABLE 20

Histidine Substitutions Selected for Further Study

| Parental Antibody | His-Substitution Antibody Designation | Substitution | | | | | |
| --- | --- | --- | --- | --- | --- | --- | --- |
| | | HCDR1 | HCDR2 | HCDR3 | LCDR1 | LCDR2 | LCDR3 |
| H4H2477N2 | H4H2477N3 | Y33H | | | | | |
| H4H2477N2 | H4H2477N4 | | N52H | | | | |
| H4H2477N2 | H4H2477N5 | Y33H | N52H | | | | |
| H4H2499N | H4H2499N2 | Y32H | | | | | |
| H4H2499N | H4H2499N3 | | T53H | | | | |
| H4H2499N | H4H2499N4 | Y32H | T53H | | | | |
| H4H2499N | H4H2499N5 | | | | Q27H<br>S30H<br>Y32H | | |
| H4H2499N | H4H2499N6 | | | | Q27H<br>S28H<br>Y32H | | |
| H4H2499N | H4H2499N7 | | | | S28H<br>S30H<br>Y32H | | |
| H4H2499N | H4H2499N8 | | | | S28H<br>S30H<br>S31H | | |
| H4H2499N | H4H2499N9 | | | | Q27H<br>S28H<br>S30H<br>Y32H | | |
| H4H2499N | H4H2499N10 | | | | | | Q90H<br>S92H<br>N93H<br>T97H |
| H4H2499N | H4H2499N11 | | | | | | Q90H<br>S92H<br>T97H |
| H4H2499N | H4H2499N12 | | | | | | S92H<br>N93H<br>T97H |
| H4H2499N | H4H2499N13 | | | | | | Q90H<br>N93H |
| H4H2499N | H4H2499N14 | | | | | | S92H<br>N93H |
| H4H2499N | H4H2499N15 | | | L98H<br>Y100H<br>V106H | | | |
| H4H2499N | H4H2499N16 | | | L98H<br>Y100H<br>M104H | | | |
| H4H2499N | H4H2499N17 | | | Y100H<br>M104H<br>V106H | | | |
| H4H2499N | H4H2499N18 | | | L98H<br>Y100H<br>M104H<br>V106H | | | |

TABLE 20-continued

Histidine Substitutions Selected for Further Study

| Parental Antibody | His-Substitution Antibody Designation | HCDR1 | HCDR2 | HCDR3 | LCDR1 | LCDR2 | LCDR3 |
|---|---|---|---|---|---|---|---|
| H4H2499N | H4H2499N19 | | | L98H<br>M104H<br>V106H | | | |
| H4H2499N | H4H2499N20 | | | Y100H<br>M104H<br>V106H | S28H<br>S30H<br>S31H | | |
| H4H2499N | H4H2499N21 | | | Y100H<br>M104H<br>V106H | | | Q90H<br>S92H<br>T97H |
| H4H2499N | H4H2499N22 | | | Y100H<br>M104H<br>V106H | | | S92H<br>N93H<br>T97H |

Example 11. pH-Selective Binding of Histidine Substitution Variant Anti-HLA-B*27 Antibodies to HLA-B*27 Expressing Cells Single-site and multiple-site substitutions of histidine for the parental amino acid(s) in the CDR regions of two anti-HLA antibodies, H4H2477N2 and H4H2499N, were made to increase pH-selective binding (see Example 10). These histidine variants and their parental antibodies were tested for binding to cell-surface human HLA-B27 expressed on C1R-neo HLA-B*2705 cells at both pH 7.2 and pH 6.0, also using electrochemiluminescence detection technology. Cells were harvested, counted, and seeded into 96 well carbon electrode plates and also blocked as described previously (see Example 8). For the pH 6.0 binding evaluation, plate-bound cells were rinsed with pH 6.0 buffer [50 mM MES, 0.0025M KCl, 0.137M NaCl, 0.0005M $MgCl_2 \times 6H_2O$, 0.0009M $CaCl_2$, 0.5% (w/v) BSA; adjusted to pH 6.0 by the addition of 5M NaOH] prior to antibody addition. Anti-HLA antibodies were diluted through 12-point, 3-fold serial dilutions starting at 50 nM either in neutral pH buffer [PBS+0.5% (w/v) BSA; at pH 7.2] for pH 7.2 binding evaluation or in pH 6.0 buffer for pH 6.0 binding evaluation then transferred to the plate-bound cells and incubated for 1 hour at 25° C. Unbound antibodies were washed off using an AquaMax2000 plate washer (MDS Analytical Technologies). Cell-bound anti-HLA antibodies were detected using an anti-human $C_H1$-specific antibody (generated in-house) conjugated with SULFO-TAG™. Addition of MSD Read Buffer, electrochemical stimulation, and luminescence detection was also performed as described above. The luminescence intensity (expressed as RLU) correlates with the amount of antibodies bound to cells. $EC_{50}$ values for histidine variants of the anti-HLA antibodies H4H2499N and H4H2477N2 binding to C1R-neo B*2705 cells were calculated using Prism Software and are shown in Tables 21 and 22, respectively.

TABLE 21

Comparison of $EC_{50}$ values and maximum RLU binding signal for H4H2499N and its histidine variants to C1R-neo B*2705 cells at pH 7.2 and pH 6.0

| AbPID | $EC_{50}$ (M) of antibodies binding to C1R-neo B*2705 at pH 6.0 | $EC_{50}$ (M) of antibodies binding to C1R-neo B*2705 at pH 7.2 | Fold increase (weaker binding) in $EC_{50}$ values at pH 6.0 versus pH 7.2 to C1R-neo B*2705 cells | Max RLU binding to C1R-neo B*2705 cells at pH 6.0 | Max RLU binding to C1R-neo B*2705 cells at pH 7.2 |
|---|---|---|---|---|---|
| H4H2499N | 1.06E−09 | 6.65E−10 | 1.6 | 18426 | 16915 |
| H4H2499N* | 1.20E−09 | 4.60E−10 | 2.6 | 26317 | 23734 |
| H4H2499N2* | 8.30E−09 | 2.90E−09 | 2.9 | 24141 | 23728 |
| H4H2499N3* | 7.90E−09 | 2.30E−09 | 3.5 | 18921 | 18387 |
| H4H2499N4* | 3.80E−08 | 6.60E−09 | 5.9 | 10315 | 14195 |
| H4H2499N5 | 5.10E−09 | 2.80E−09 | 1.8 | 19522 | 16912 |
| H4H2499N6 | 4.60E−09 | 2.50E−09 | 1.8 | 20042 | 17356 |
| H4H2499N7 | 4.30E−09 | 2.80E−09 | 1.5 | 18058 | 15677 |
| H4H2499N8 | 5.20E−09 | 1.80E−09 | 2.9 | 19915 | 17759 |
| H4H2499N8* | 4.80E−09 | 2.00E−09 | 2.3 | 24905 | 26736 |
| H4H2499N9 | 5.50E−09 | 3.70E−09 | 1.5 | 15870 | 15695 |
| H4H2499N10 | 8.00E−09 | 3.80E−09 | 2.1 | 9502 | 8599 |
| H4H2499N11 | 1.20E−08 | 4.60E−09 | 2.6 | 9549 | 9605 |
| H4H2499N11* | 1.70E−08 | 4.80E−09 | 3.6 | 11970 | 14364 |
| H4H2499N12 | 2.20E−09 | 1.30E−09 | 1.7 | 24334 | 23014 |
| H4H2499N12* | 3.20E−09 | 1.20E−09 | 2.7 | 31917 | 32762 |
| H4H2499N13 | 2.22E−08 | 2.11E−08 | 1.1 | 8124 | 9563 |
| H4H2499N14 | 1.50E−09 | 7.70E−10 | 1.9 | 19137 | 17315 |

TABLE 21-continued

Comparison of $EC_{50}$ values and maximum RLU binding signal for H4H2499N and its histidine variants to C1R-neo B*2705 cells at pH 7.2 and pH 6.0

| AbPID | $EC_{50}$ (M) of antibodies binding to C1R-neo B*2705 at pH 6.0 | $EC_{50}$ (M) of antibodies binding to C1R-neo B*2705 at pH 7.2 | Fold increase (weaker binding) in $EC_{50}$ values at pH 6.0 versus pH 7.2 to C1R-neo B*2705 cells | Max RLU binding to C1R-neo B*2705 cells at pH 6.0 | Max RLU binding to C1R-neo B*2705 cells at pH 7.2 |
|---|---|---|---|---|---|
| H4H2499N15 | 1.92E−08 | 9.20E−09 | 2.1 | 9681 | 8001 |
| H4H2499N16 | IC | IC | IC | 10010 | 11377 |
| H4H2499N17 | 1.00E−08 | 3.20E−09 | 3.2 | 16905 | 18931 |
| H4H2499N17* | 1.60E−08 | 3.10E−09 | 5.3 | 21621 | 23850 |
| H4H2499N18 | 8.10E−09 | 3.90E−09 | 2.1 | 14600 | 13055 |
| H4H2499N19 | IC | 2.53E−08 | IC | 7870 | 9986 |
| H4H2499N20* | 8.70E−09 | 2.50E−09 | 3.5 | 22709 | 24372 |
| H4H2499N21* | 5.60E−08 | 8.00E−09 | 7.1 | 9680 | 13192 |
| H4H2499N22* | 6.10E−09 | 1.90E−09 | 3.3 | 32823 | 31612 |

*Performed on a separate day from a first experiment
IC = inconclusive

TABLE 22

Comparison of $EC_{50}$ values and maximum RLU binding signal for H4H2477N2 and its histidine variants binding to C1R-neo B*2705 cells at pH 7.2 and pH 6.0

| AbPID | $EC_{50}$ (M) of antibodies binding to C1R-neo B*2705 at pH 6.0 | $EC_{50}$ (M) of antibodies binding to C1R-neo B*2705 at pH 7.2 | Fold increase (weaker binding) in $EC_{50}$ values at pH 6.0 versus pH 7.2 to C1R-neo B*2705 cells | Max RLU binding to C1R-neo B*2705 cells at pH 6.0 | Max RLU binding to C1R-neo B*2705 cells at pH 7.2 |
|---|---|---|---|---|---|
| H4H2477N2 | 7.90E−10 | 5.60E−10 | 1.4 | 46624 | 42761 |
| H4H2477N3 | 3.60E−08 | 4.70E−09 | 7.7 | 22164 | 30529 |
| H4H2477N4 | 6.40E−08 | 2.90E−09 | 21.8 | 25658 | 37452 |
| H4H2477N5 | IC | IC | IC | 108897 | 137977 |

Binding experiments for parental antibody H4H2499N and its histidine variants were performed on two separate days. Some of the antibodies were included in both experiments, and the data from both experiments are shown in Table 21. Several of the histidine variants (H4H2499N3, H4H2499N4, H4H2499N11, H4H2499N17, H4H2499N20, H4H2499N21, and H4H2499N22) displayed greater than a 3-fold decrease in $EC_{50}$ value at pH 6.0 compared with their $EC_{50}$ value at pH 7.2, while the parental antibody, in two experiments, exhibited a 1.6-fold and a 2.6-fold decrease in $EC_{50}$ value at pH 6.0 compared with its $EC_{50}$ value at pH 7.2. $EC_{50}$ values for two of the histidine variants, H4H2499N16 and H4H2499N19, could not be assigned at both pH 6.0 and pH 7.2 due to the lack of a complete sigmoidal curve at tested antibody concentrations.

As shown in Table 22, two of the histidine variants of parental antibody H4H2477N2 (H4H2477N3 and H4H2477N4) tested for binding to C1R-neo B*2705 cells displayed 7.7-fold and 21.8-fold decreases, respectively, in $EC_{50}$ values at pH 6.0 compared with their $EC_{50}$ values at pH 7.2, while the parental H4H2477N2 antibody exhibited no measurable decrease in $EC_{50}$ value at pH 6.0 compared with its $EC_{50}$ value at pH 7.2. For histidine variant H4H2477N5, $EC_{50}$ values could not be assigned at both pH 7.2 and pH 6.0 due to the lack of a complete sigmoidal curve at tested antibody concentrations.

The present invention is not to be limited in scope by the specific embodiments describe herein. Indeed, various modifications of the invention in addition to those described herein will become apparent to those skilled in the art from the foregoing description and the accompanying FIGURES. Such modifications are intended to fall within the scope of the appended claims.

What is claimed is:

1. An isolated antibody, or antigen-binding fragment thereof, that specifically binds HLA-B*27, wherein the antibody or antigen-binding fragment comprises the heavy and light chain complementarity determining regions (CDRs) of a heavy chain variable region/light chain variable region (HCVR/LCVR) amino acid sequence pair selected from the group consisting of: SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, and 370/378.

2. The isolated antibody or antigen-binding fragment of claim 1, wherein the antibody or antigen-binding fragment comprises HCDR1-HCDR2-HCDR3-LCDR1-LCDR2-LCDR3 domains, respectively, selected from the group consisting of: SEQ ID NOs: 4-6-8-12-14-16; 20-22-24-28-30-32; 36-38-40-44-46-48; 52-54-56-60-62-64; 68-70-72-76-78-80; 84-86-88-92-94-96; 100-102-104-108-110-112;

116-118-120-124-126-128; 132-134-136-140-142-144; 148-150-152-156-158-160; 164-166-168-172-174-176; 180-182-184-188-190-192; 196-198-200-204-206-208; 212-214-216-220-222-224; 228-230-232-236-238-240; 244-246-248-252-254-256; 260-262-264-268-270-272; 276-278-280-284-286-288; 292-294-296-300-302-304; 308-310-312-316-318-320; 324-326-328-332-334-336; 340-342-344-348-350-352; 356-358-360-364-366-368; and 372-374-376-380-382-384.

3. The isolated antibody or antigen-binding fragment of claim 2, wherein the antibody or antigen-binding fragment comprises a HCVR/LCVR amino acid sequence pair selected from the group consisting of: SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, and 370/378.

4. The isolated antibody or antigen-binding fragment of claim 1, wherein the antibody or antigen-binding fragment thereof binds HLA-B*27 at pH 5.75 with a $K_D$ that is at least 5-times greater than the $K_D$ for the antibody binding to HLA-B*27 at pH 7.2, and comprises a HCVR/LCVR amino acid sequence pair selected from the group consisting of: SEQ ID NOs: 226/234, 258/266, 290/298, 338/346, and 370/378.

5. A pharmaceutical composition comprising the antibody or antigen-binding fragment of claim 1 and a pharmaceutically acceptable carrier or diluent.

6. The isolated antibody or antigen-binding fragment of claim 1, wherein the antibody or antigen-binding fragment blocks HLA-B*27-induced T-cell activation in vitro, and comprises the CDRs of a HCVR/LCVR amino acid sequence pair selected from the group consisting of: SEQ ID NOs: 66/74, 82/90, 98/106, 114/122, 146/154, 162/170, 178/186, 194/202, 210/218, 226/234, 242/250, 258/266, 274/282, 290/298, 306/314, 322/330, 338/346, 354/362, and 370/378.

7. The isolated antibody or antigen-binding fragment of claim 6, wherein the antibody or antigen-binding fragment comprises HCDR1-HCDR2-HCDR3-LCDR1-LCDR2-LCDR3 domains, respectively, selected from the group consisting of: SEQ ID NOs: 68-70-72-76-78-80; 84-86-88-92-94-96; 100-102-104-108-110-112; 116-118-120-124-126-128; 148-150-152-156-158-160; 164-166-168-172-174-176; 180-182-184-188-190-192; 196-198-200-204-206-208; 212-214-216-220-222-224; 228-230-232-236-238-240; 244-246-248-252-254-256; 260-262-264-268-270-272; 276-278-280-284-286-288; 292-294-296-300-302-304; 308-310-312-316-318-320; 324-326-328-332-334-336; 340-342-344-348-350-352; 356-358-360-364-366-368; and 372-374-376-380-382-384.

8. The isolated antibody or antigen-binding fragment of claim 7, wherein the antibody or antigen-binding fragment comprises a HCVR/LCVR amino acid sequence pair selected from the group consisting of: SEQ ID NOs: 66/74, 82/90, 98/106, 114/122, 146/154, 162/170, 178/186, 194/202, 210/218, 226/234, 242/250, 258/266, 274/282, 290/298, 306/314, 322/330, 338/346, 354/362, and 370/378.

9. A pharmaceutical composition comprising the antibody or antigen-binding fragment of claim 6 and a pharmaceutically acceptable carrier or diluent.

10. The isolated antibody or antigen-binding fragment of claim 1, wherein the antibody or antigen-binding fragment thereof exhibits enhanced binding to HLA-B*2705 or HLA-B*2709 as compared to HLA-B*07, and comprises a HCVR/LCVR amino acid sequence pair selected from the group consisting of: SEQ ID NOs: 66/74, 82/90, 98/106, 114/122, 146/154, 162/170, 178/186, 194/202, 210/218, 226/234, 242/250, 258/266, 274/282, 290/298, 306/314, 322/330, 338/346, and 354/362.

11. A pharmaceutical composition comprising the antibody or antigen-binding fragment of claim 10 and a pharmaceutically acceptable carrier or diluent.

12. An isolated antibody, or antigen-binding fragment thereof, that specifically binds HLA-B*27, wherein the antibody or antigen-binding fragment comprises heavy and light chain CDRs of a HCVR/LCVR amino acid sequence pair consisting of SEQ ID NOs: 146/154.

13. The isolated antibody or antigen-binding fragment of claim 12, wherein the antibody or antigen-binding fragment comprises HCDR1-HCDR2-HCDR3-LCDR1-LCDR2-LCDR3 domains, respectively, consisting of the amino acid sequences of SEQ ID NOs: 148-150-152-156-158-160.

14. The isolated antibody or antigen-binding fragment of claim 13, wherein the antibody or antigen-binding fragment comprises the HCVR/LCVR amino acid sequence pair of SEQ ID NOs: 146/154.

15. A pharmaceutical composition comprising the antibody or antigen-binding fragment of claim 12 and a pharmaceutically acceptable carrier or diluent.

* * * * *

SEQUENCE LISTING

<160> NUMBER OF SEQ ID NOS: 393

<210> SEQ ID NO 1
<211> LENGTH: 369
<212> TYPE: DNA
<213> ORGANISM: Artificial Sequence
<220> FEATURE:
<223> OTHER INFORMATION: Synthetic

<400> SEQUENCE: 1

```
caggtgcagt tacagcagtg gggcgcagga ctgttgaagc cttcggagac cctgtccctc   60
acctgcgctg tctatggtgg gtccttcagt gattactact ggagctggat ccgccagccc  120
ccagggaagg gctggagtg gattgggaa atcaatcata gtggaaacac caactacaac  180
ccgtccctca agagtcgagt caccatatca gtagacacgt ccaagaacca gttctccctg  240
aaactgaggt ctgtgaccgc cgcggacatg gctgtgtatt actgtgcgag gatacagtta  300
tggttaagag ggtatgacta ctacggtatg gacgtctggg gccaagggac cacggtcacc  360
gtctcctca                                                          369
```

<210> SEQ ID NO 2
<211> LENGTH: 123
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Gln Gln Trp Gly Ala Gly Leu Leu Lys Pro Ser Glu
  1               5                  10                  15
Thr Leu Ser Leu Thr Cys Ala Val Tyr Gly Gly Ser Phe Ser Asp Tyr
             20                  25                  30
Tyr Trp Ser Trp Ile Arg Gln Pro Pro Gly Lys Gly Leu Glu Trp Ile
         35                  40                  45
Gly Glu Ile Asn His Ser Gly Asn Thr Asn Tyr Asn Pro Ser Leu Lys
     50                  55                  60
Ser Arg Val Thr Ile Ser Val Asp Thr Ser Lys Asn Gln Phe Ser Leu
 65                  70                  75                  80
Lys Leu Arg Ser Val Thr Ala Ala Asp Met Ala Val Tyr Tyr Cys Ala
                 85                  90                  95
Arg Ile Gln Leu Trp Leu Arg Gly Tyr Asp Tyr Tyr Gly Met Asp Val
            100                 105                 110
Trp Gly Gln Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggtgggtcct tcagtgatta ctac                                          24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Gly Ser Phe Ser Asp Tyr Tyr
  1               5
```

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
atcaatcata gtggaaacac c                                              21

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Asn His Ser Gly Asn Thr
 1               5

<210> SEQ ID NO 7
<211> LENGTH: 51
<212> TYPE: DNA
<213> ORGANISM: Artificial Sequence
<220> FEATURE:
<223> OTHER INFORMATION: Synthetic

<400> SEQUENCE: 7
gcgaggatac agttatggtt aagagggtat gactactacg gtatggacgt c             51

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Ala Arg Ile Gln Leu Trp Leu Arg Gly Tyr Asp Tyr Tyr Gly Met Asp
 1               5                  10                  15

Val

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc ctgtctgcat ctgtaggaga cagagtcacc     60
atcacttgcc gggcaagtca gggcatcaga aatgatttag ctggtatca gcagaaacca    120 gggaaagccc ctaagcgcct gatctatgct gcatccagtt tgcaaggtgg ggtcccatca    180
aggttcagcg gcagtggatc tgggacagaa ttcagtctca caatcagcag cctgcagcct    240
gaagattttg caagttatta ctgtctacag cataatactt atccgtggac gttcggccaa    300
gggaccaagg tggaaatcaa a                                              321

<210> SEQ ID NO 10
<211> LENGTH: 107
<212> TYPE: PRT
<213> ORGANISM: Artificial Sequence
<220> FEATURE:

<223> OTHER INFORMATION: Synthetic

<400> SEQUENCE: 10

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Gly Gly Val Pro Ser Arg Phe Ser Gly
 50                  55                  60

Ser Gly Ser Gly Thr Glu Phe Ser Leu Thr Ile Ser Ser Leu Gln Pro
 65                  70                  75                  80

Glu Asp Phe Ala Ser Tyr Tyr Cys Leu Gln His Asn Thr Tyr Pro Trp
                 85                  90                  95

Thr Phe Gly Gln Gly Thr Lys Val Glu Ile Lys
                100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagggcatca gaaatgat                                                   18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Gly Ile Arg Asn Asp
 1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                              9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Ala Ala Ser
 1
```

<210> SEQ ID NO 15
<211> LENGTH: 27
<212> TYPE: DNA

<213> ORGANISM: Artificial Sequence
<220> FEATURE:
<223> OTHER INFORMATION: Synthetic

<400> SEQUENCE: 15
ctacagcata atacttatcc gtggacg        27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Leu Gln His Asn Thr Tyr Pro Trp Thr
 1               5

<210> SEQ ID NO 17
<211> LENGTH: 375
<212> TYPE: DNA
<213> ORGANISM: Artificial Sequence
<220> FEATURE:
<223> OTHER INFORMATION: Synthetic

<400> SEQUENCE: 17
caggtgcaac tggtgcaatc tggggctgac gtgaagtggc ctggggcctc agtgaaggtc        60
tcctgcaggg cttctggata caccttcacc ggctactata tgcactgggt gcggcaggcc       120
cctggacaag gcttgagtg gatgggatgg atcaacccta acaatggtgg cacaaattat       180
gcacagaagt ttcagggcag ggtcaccatg accagggaca cgtccatcac cacagtctac       240
atggaactga gcagtctgat atctgacgac acggccgtat attactgtgc gagaggggag       300
gatttggaac tacggaacta ctactactac ggtatggacg tctggggcca agggacctcg       360
gtcaccgtct cctca       375

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Asp Val Lys Trp Pro Gly Ala
 1               5                  10                  15

Ser Val Lys Val Ser Cys Arg Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Asn Gly Gly Thr Asn Tyr Ala Gln Lys Phe
     50                  55                  60

Gln Gly Arg Val Thr Met Thr Arg Asp Thr Ser Ile Thr Thr Val Tyr
 65                  70                  75                  80

Met Glu Leu Ser Ser Leu Ile Ser Asp Asp Thr Ala Val Tyr Tyr Cys
                 85                  90                  95

Ala Arg Gly Glu Asp Leu Glu Leu Arg Asn Tyr Tyr Tyr Tyr Gly Met
            100                 105                 110

Asp Val Trp Gly Gln Gly Thr Ser Val Thr Val Ser Ser
        115                 120                 125

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggatacacct tcaccggcta ctat                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Tyr Thr Phe Thr Gly Tyr Tyr
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21 atcaaccccta acaatggtgg caca                                         24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Asn Pro Asn Asn Gly Gly Thr
1               5

<210> SEQ ID NO 23
<211> LENGTH: 54
<212> TYPE: DNA
<213> ORGANISM: Artificial Sequence
<220> FEATURE:
<223> OTHER INFORMATION: Synthetic

<400> SEQUENCE: 23
gcgagagggg aggatttgga actacggaac tactactact acggtatgga cgtc         54

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

Ala Arg Gly Glu Asp Leu Glu Leu Arg Asn Tyr Tyr Tyr Tyr Gly Met
1               5                   10                  15

Asp Val

<210> SEQ ID NO 25

<211> LENGTH: 318
<212> TYPE: DNA
<213> ORGANISM: Artificial Sequence
<220> FEATURE:
<223> OTHER INFORMATION: Synthetic

<400> SEQUENCE: 25

```
gacatccaga tgacccagtc tccatcctcc ctgtctgcat ctgtaggaga cagagtcacc      60
atcacttgcc gggcaagtca gagtattagt agctatttaa attggtatca gcagaaacca     120
gggaaagccc ctaaactcct gatctatgct gcatccaatt tgcaaagtgg ggtcccatca     180
aggttcagtg gcagtggatt tgggacagat ttcactctca ccatcagcag tctgcaatct     240
gaagattttg caacttacta ctgtcagcag acttacagta cccggacgtt cggccgaggg     300
accaaggtgg aaatcaat                                                   318
```

<210> SEQ ID NO 26
<211> LENGTH: 106
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Asn Leu Gln Ser Gly Val Pro Ser Arg Phe Ser Gly
    50                  55                  60
Ser Gly Phe Gly Thr Asp Phe Thr Leu Thr Ile Ser Ser Leu Gln Ser
65                  70                  75                  80
Glu Asp Phe Ala Thr Tyr Tyr Cys Gln Gln Thr Tyr Ser Thr Arg Thr
                85                  90                  95
Phe Gly Arg Gly Thr Lys Val Glu Ile Asn
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagagtatta gtagctat                                                    18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Ser Ile Ser Ser Tyr
1               5
```

<210> SEQ ID NO 29
<211> LENGTH: 9

```
<212> TYPE: DNA
<213> ORGANISM: Artificial Sequence
<220> FEATURE:
<223> OTHER INFORMATION: Synthetic

<400> SEQUENCE: 29 gctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
 1

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
cagcagactt acagtacccg gacg                                             24

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Gln Gln Thr Tyr Ser Thr Arg Thr
 1               5

<210> SEQ ID NO 33
<211> LENGTH: 357
<212> TYPE: DNA
<213> ORGANISM: Artificial Sequence
<220> FEATURE:
<223> OTHER INFORMATION: Synthetic

<400> SEQUENCE: 33
caggtgcagg tggtggagtc tgggggaggc gtggtccagc ctggggggtc cctgagactc       60
tcctgtgcag cctctggatt caccttcagt agttatggca tgcattgggt ccgccaggct      120
ccaggcaagg ggctggagtg ggtggcactt atatcatatg atggaaaaaa taaatattat      180
gtagactccg tgaagggccg attcaccatc tccagagaca attccaagaa cacgctgtat      240
ctgcaaatga acagcttgag agctgaggac acggctgtgt attactgtgc gaaagagagg      300
aatatagcgg acggtatgga cgtctgggc caagggacca cggtcaccgt ctcctca         357

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34
```

Gln Val Gln Val Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Lys Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Glu Arg Asn Ile Ala Asp Gly Met Asp Val Trp Gly Gln Gly
        100                 105                 110

Thr Thr Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct tcagtagtta tggc                                        24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Ser Tyr Gly
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atatcatatg atggaaaaaa taaa                                        24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Tyr Asp Gly Lys Asn Lys
1               5

<210> SEQ ID NO 39
<211> LENGTH: 36
<212> TYPE: DNA
<213> ORGANISM: Artificial Sequence -continued

```
<220> FEATURE:
<223> OTHER INFORMATION: Synthetic

<400> SEQUENCE: 39
gcgaaagaga ggaatatagc ggacggtatg gacgtc                              36

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Ala Lys Glu Arg Asn Ile Ala Asp Gly Met Asp Val
 1               5                  10

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aacttcagtg gcagtggatc tgggacagat ttcactctca ccatcagcag tctgcaacct    240
gaagattttg caacttacta ctgtcaacag agttacagta ccccgtacac ttttggccag    300
gggaccaagc tggagatcaa a                                              321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Asn Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys
             100                 105

<210> SEQ ID NO 43
<211> LENGTH: 18
<212> TYPE: DNA
<213> ORGANISM: Artificial Sequence
<220> FEATURE:
```

<223> OTHER INFORMATION: Synthetic

<400> SEQUENCE: 43
cagagcatta gcagctat                                                          18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Ile Ser Ser Tyr
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                                     9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacagagtt acagtacccc gtacact                                                27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Ser Tyr Ser Thr Pro Tyr Thr
 1               5

<210> SEQ ID NO 49
<211> LENGTH: 369
<212> TYPE: DNA
<213> ORGANISM: Artificial Sequence
<220> FEATURE:
<223> OTHER INFORMATION: Synthetic

<400> SEQUENCE: 49

```
caggtgcagt tacagcagtg gggcgcagga ctgttgaagc cttcggagac cctgtccctc    60
acctgcgctg tctatggtgg gtccttcagt gattactact ggagctggat ccgccagccc   120
ccagggaagg ggctggagtg gattggggaa atcaatcata ggggaaacac caactacaac   180
ccgtccctca agagtcgagt caccatatca gtagacacgt ccaagaacca gttctccctg   240
aaactgaggt ctgtgaccgc cgcggacatg gctgtgtatt actgtgcgag gatacagtta   300
tggttaagag ggtatgacta ctacggtatg acgtctggg gccaagggac cacggtcacc   360
gtctcctca                                                           369
```

\<210\> SEQ ID NO 50
\<211\> LENGTH: 123
\<212\> TYPE: PRT
\<213\> ORGANISM: Artificial Sequence
\<220\> FEATURE:
\<223\> OTHER INFORMATION: Synthetic

\<400\> SEQUENCE: 50

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Met Ala Val Tyr Tyr Cys Ala
                85                  90                  95

Arg Ile Gln Leu Trp Leu Arg Gly Tyr Asp Tyr Tyr Gly Met Asp Val
            100                 105                 110

Trp Gly Gln Gly Thr Thr Val Thr Val Ser Ser
        115                 120
```

\<210\> SEQ ID NO 51
\<211\> LENGTH: 24
\<212\> TYPE: DNA
\<213\> ORGANISM: Artificial Sequence
\<220\> FEATURE:
\<223\> OTHER INFORMATION: Synthetic

\<400\> SEQUENCE: 51

```
ggtgggtcct tcagtgatta ctac                                           24
```

\<210\> SEQ ID NO 52
\<211\> LENGTH: 8
\<212\> TYPE: PRT
\<213\> ORGANISM: Artificial Sequence
\<220\> FEATURE:
\<223\> OTHER INFORMATION: Synthetic

\<400\> SEQUENCE: 52

```
Gly Gly Ser Phe Ser Asp Tyr Tyr
1               5
```

\<210\> SEQ ID NO 53
\<211\> LENGTH: 21
\<212\> TYPE: DNA
\<213\> ORGANISM: Artificial Sequence
\<220\> FEATURE:

<223> OTHER INFORMATION: Synthetic

<400> SEQUENCE: 53
atcaatcata ggggaaacac c                                            21

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Ile Asn His Arg Gly Asn Thr
1               5

<210> SEQ ID NO 55
<211> LENGTH: 51
<212> TYPE: DNA
<213> ORGANISM: Artificial Sequence
<220> FEATURE:
<223> OTHER INFORMATION: Synthetic

<400> SEQUENCE: 55
gcgaggatac agttatggtt aagagggtat gactactacg gtatggacgt c           51

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Ala Arg Ile Gln Leu Trp Leu Arg Gly Tyr Asp Tyr Tyr Gly Met Asp
1               5                   10                  15
Val

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctcc ctgtctgcat ctgtaggaga cagagtcacc    60
atcacttgcc gggcaagtca gggcatcaga aatgatttag ctggtatca gcagaaacca   120 gggaaagccc ctaagcgcct gatctatgct gcatccagtt tgcaaggtgg ggtcccatca   180
aggttcagcg gcagtggatc tgggacagaa ttcagtctca caatcagcag cctgcagcct   240
gaagattttg caagttatta ctgtctacag cataatactt atccgtggac gttcggccaa   300
gggaccaagg tggaaatcaa a                                             321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly

```
                1               5                   10                  15
Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Gly Gly Val Pro Ser Arg Phe Ser Gly
        50                  55                  60

Ser Gly Ser Gly Thr Glu Phe Ser Leu Thr Ile Ser Ser Leu Gln Pro
 65                 70                  75                  80

Glu Asp Phe Ala Ser Tyr Tyr Cys Leu Gln His Asn Thr Tyr Pro Trp
                85                  90                  95

Thr Phe Gly Gln Gly Thr Lys Val Glu Ile Lys
                100                 105
```

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggcatca gaaatgat                                                   18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Arg Asn Asp
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                              9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63

-continued

```
ctacagcata atacttatcc gtggacg                                             27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Gln His Asn Thr Tyr Pro Trp Thr
 1               5

<210> SEQ ID NO 65
<211> LENGTH: 375
<212> TYPE: DNA
<213> ORGANISM: Artificial Sequence
<220> FEATURE:
<223> OTHER INFORMATION: Synthetic

<400> SEQUENCE: 65
caggtgcaac tggtgcaatc tggggctgac gtgaagtggc ctggggcctc agtgaaggtc        60
tcctgcaggg cttctggata caccttcacc ggctactata tgcactgggt gcggcaggcc       120
cctggacaag gcttgagtg gatgggatgg atcaaccct acaatggtgg cacaaattat        180
gcacagaagt tcagggcag gtcaccatg accaggaca cgtccatcac cacagtctac         240
atggaactga gcagtctgat atctgacgac acggccgtat attactgtgc gagaggggag       300
gatttggaac tacggaacta ctactactac ggtatggacg tctggggcca agggacctcg       360
gtcaccgtct cctca                                                        375

<210> SEQ ID NO 66
<211> LENGTH: 125
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Ala Asp Val Lys Trp Pro Gly Ala
 1               5                  10                  15

Ser Val Lys Val Ser Cys Arg Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Asn Gly Gly Thr Asn Tyr Ala Gln Lys Phe
        50                  55                  60

Gln Gly Arg Val Thr Met Thr Arg Asp Thr Ser Ile Thr Thr Val Tyr
 65                  70                  75                  80

Met Glu Leu Ser Ser Leu Ile Ser Asp Asp Thr Ala Val Tyr Tyr Cys
                85                  90                  95

Ala Arg Gly Glu Asp Leu Glu Leu Arg Asn Tyr Tyr Tyr Tyr Gly Met
            100                 105                 110

Asp Val Trp Gly Gln Gly Thr Ser Val Thr Val Ser Ser
        115                 120                 125

<210> SEQ ID NO 67
<211> LENGTH: 24
<212> TYPE: DNA
<213> ORGANISM: Artificial Sequence
```

<220> FEATURE:
<223> OTHER INFORMATION: Synthetic

<400> SEQUENCE: 67
ggatacacct tcaccggcta ctat                                      24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Tyr Thr Phe Thr Gly Tyr Tyr
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69 atcaaccta acaatggtgg caca                                       24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Asn Pro Asn Asn Gly Gly Thr
1               5

<210> SEQ ID NO 71
<211> LENGTH: 54
<212> TYPE: DNA
<213> ORGANISM: Artificial Sequence
<220> FEATURE:
<223> OTHER INFORMATION: Synthetic

<400> SEQUENCE: 71
gcgagagggg aggatttgga actacggaac tactactact acggtatgga cgtc     54

<210> SEQ ID NO 72
<211> LENGTH: 18
<212> TYPE: PRT
<213> ORGANISM: Artificial Sequence
<220> FEATURE:
<223> OTHER INFORMATION: Synthetic

<400> SEQUENCE: 72

Ala Arg Gly Glu Asp Leu Glu Leu Arg Asn Tyr Tyr Tyr Tyr Gly Met
1               5                   10                  15

Asp Val

<210> SEQ ID NO 73
<211> LENGTH: 318
<212> TYPE: DNA
<213> ORGANISM: Artificial Sequence
<220> FEATURE:
<223> OTHER INFORMATION: Synthetic

<400> SEQUENCE: 73

```
gacatccaga tgacccagtc tccatcctcc ctgtctgcat ctgtaggaga cagagtcacc      60
atcacttgcc gggcaagtca gagtattagt agctatttaa attggtatca gcagaaacca     120
gggaaagccc ctaaactcct gatctatgct gcatccaatt tgcaaagtgg ggtcccatca     180
aggttcagtg gcagtggatt tgggacagat ttcactctca ccatcagcag tctgcaatct     240
gaagattttg caacttacta ctgtcagcag acttacagta cccggacgtt cggccgaggg     300
accaaggtgg aaatcaaa                                                   318
```

<210> SEQ ID NO 74
<211> LENGTH: 106
<212> TYPE: PRT
<213> ORGANISM: Artificial Sequence
<220> FEATURE:
<223> OTHER INFORMATION: Synthetic

<400> SEQUENCE: 74

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Asn Leu Gln Ser Gly Val Pro Ser Arg Phe Ser Gly
     50                  55                  60

Ser Gly Phe Gly Thr Asp Phe Thr Leu Thr Ile Ser Ser Leu Gln Ser
 65                  70                  75                  80

Glu Asp Phe Ala Thr Tyr Tyr Cys Gln Gln Thr Tyr Ser Thr Arg Thr
                 85                  90                  95

Phe Gly Arg Gly Thr Lys Val Glu Ile Lys
            100                 105
```

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

```
cagagtatta gtagctat                                                    18
```

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

```
Gln Ser Ile Ser Ser Tyr
  1               5
```

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc                                                                    9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
 1

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
cagcagactt acagtacccg gacg                                                  24

<210> SEQ ID NO 80
<211> LENGTH: 8
<212> TYPE: PRT
<213> ORGANISM: Artificial Sequence
<220> FEATURE:
<223> OTHER INFORMATION: Synthetic

<400> SEQUENCE: 80

Gln Gln Thr Tyr Ser Thr Arg Thr
 1               5

<210> SEQ ID NO 81
<211> LENGTH: 357
<212> TYPE: DNA
<213> ORGANISM: Artificial Sequence
<220> FEATURE:
<223> OTHER INFORMATION: Synthetic

<400> SEQUENCE: 81
caggtgcagg tggtggagtc tgggggaggc gtggtccagc ctggggggtc cctgagactc          60
tcctgtgcag cctctggatt caccttcagt agttatgcca tgcattgggt ccgccaggct         120
ccaggcaagg ggctggagtg ggtggcactt atatcatatg atggaaaaaa taaatattat         180
gtagactccg tgaagggccg attcaccatc tccagagaca attccaagaa cacgctgtat         240
ctgcaaatga acagcttgag agctgaggac acggctgtgt attactgtgc gaaagagagg         300
aatatagcgg acggtatgga cgtctggggc caagggacca cggtcaccgt ctcctca           357

<210> SEQ ID NO 82
<211> LENGTH: 119
<212> TYPE: PRT
<213> ORGANISM: Artificial Sequence
<220> FEATURE:
<223> OTHER INFORMATION: Synthetic

<400> SEQUENCE: 82

Gln Val Gln Val Val Glu Ser Gly Gly Gly Val Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Leu Ile Ser Tyr Asp Gly Lys Asn Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Arg Asn Ile Ala Asp Gly Met Asp Val Trp Gly Gln Gly
             100                 105                 110

Thr Thr Val Thr Val Ser Ser
        115

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct tcagtagtta tggc                                           24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Ser Ser Tyr Gly
 1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
atatcatatg atggaaaaaa taaa                                           24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Tyr Asp Gly Lys Asn Lys
 1               5

<210> SEQ ID NO 87
<211> LENGTH: 36
<212> TYPE: DNA
<213> ORGANISM: Artificial Sequence
<220> FEATURE:
<223> OTHER INFORMATION: Synthetic

<400> SEQUENCE: 87
gcgaaagaga ggaatatagc ggacggtatg gacgtc                                36

<210> SEQ ID NO 88
<211> LENGTH: 12
<212> TYPE: PRT
<213> ORGANISM: Artificial Sequence
<220> FEATURE:
<223> OTHER INFORMATION: Synthetic

<400> SEQUENCE: 88

Ala Lys Glu Arg Asn Ile Ala Asp Gly Met Asp Val
 1               5                  10

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
agattcagtg gcagtggatc tgggacagat ttcactctca ccatcagcag tctgcaacct     240
gaagattttg caacttacta ctgtcaacag agttacagta ccccgtacac ttttggccag     300
gggaccaagc tggagatcaa a                                               321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagcatta gcagctat                                                    18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Ile Ser Ser Tyr
 1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                                9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacagagtt acagtacccc gtacact                                           27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Tyr Thr
 1               5

<210> SEQ ID NO 97
<211> LENGTH: 369
<212> TYPE: DNA
<213> ORGANISM: Artificial Sequence
<220> FEATURE:
<223> OTHER INFORMATION: Synthetic

<400> SEQUENCE: 97
caggtgcagc tacagcagtg gggcgcagga ctgttgaagc cttcggagac cctgtccctc       60
acctgcgctg tctatggtgg gtccttcagt ggttactact ggagctggat ccgccagacc     120
ccagggaagg ggctggagtg gattggggaa atcagtcata gtggaaacaa caactacaac     180

```
ccgtccctca agagtcgagt caccatgtca aaagacacgt ccaagaacca gttctccctg    240
aagctgagct ctgtgaccgc cgcggacacg gctgtctatt attgtgcgag gatacagtta    300
tggttaagag ggaacgacta ctacggtatg gacgtctggg gccaaggat cacggtcacc     360 gtctcctca                                                            369
```

<210> SEQ ID NO 98
<211> LENGTH: 123
<212> TYPE: PRT
<213> ORGANISM: Artificial Sequence
<220> FEATURE:
<223> OTHER INFORMATION: Synthetic

<400> SEQUENCE: 98

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Thr Pro Gly Lys Gly Leu Glu Trp Ile
         35                  40                  45

Gly Glu Ile Ser His Ser Gly Asn Asn Tyr Asn Pro Ser Leu Lys
     50                  55                  60

Ser Arg Val Thr Met Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ile Gln Leu Trp Leu Arg Gly Asn Asp Tyr Tyr Gly Met Asp Val
            100                 105                 110

Trp Gly Gln Gly Ile Thr Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggtgggtcct tcagtggtta ctac                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Gly Ser Phe Ser Gly Tyr Tyr
 1               5
```

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101

```
atcagtcata gtggaaacaa c                                               21
```

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Ser His Ser Gly Asn Asn
 1               5

<210> SEQ ID NO 103
<211> LENGTH: 51
<212> TYPE: DNA
<213> ORGANISM: Artificial Sequence
<220> FEATURE:
<223> OTHER INFORMATION: Synthetic

<400> SEQUENCE: 103
gcgaggatac agttatggtt aagagggaac gactactacg gtatggacgt c            51

<210> SEQ ID NO 104
<211> LENGTH: 17
<212> TYPE: PRT
<213> ORGANISM: Artificial Sequence
<220> FEATURE:
<223> OTHER INFORMATION: Synthetic

<400> SEQUENCE: 104

Ala Arg Ile Gln Leu Trp Leu Arg Gly Asn Asp Tyr Tyr Gly Met Asp
 1               5                  10                  15

Val

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc    60
atcacttgcc gggcaagtca gggcattaga aatgatttag gtggtatca gcagaaacca   120
gggaaagccc ctaagcgcct gatctatgct gcatccagtt tgcaaggtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa a                                              321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Gly Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggcatta gaaatgat                                                       18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Gly Ile Arg Asn Asp
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                                  9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacagcata atagttaccc gtggacg                                             27

<210> SEQ ID NO 112

```
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln His Asn Ser Tyr Pro Trp Thr
 1               5

<210> SEQ ID NO 113
<211> LENGTH: 360
<212> TYPE: DNA
<213> ORGANISM: Artificial Sequence
<220> FEATURE:
<223> OTHER INFORMATION: Synthetic

<400> SEQUENCE: 113
caggtgcagc tggtggagtc tgggggaggc gtggtccagc ctggagggtc cctgagactc      60
tcctgtgcag cctctggatt caccttcagt acctatggca tggattgggt ccgccaggct     120
ccaggcaagg ggctggagtg ggtggcagtg atatcatatg atggacgtaa taaaaactat     180
gtagactccg tgaagggccg attcaccatc tccagagaca attccaagaa cacgctgtat     240
ctgcaaatga acagcctgag agctgaggac tcggctgtgt atttctgtgc gaaagagggg     300
ggactgggga cctggtactt cgatctctgg ggccgtggca ccctggtcac tgtctcttca     360

<210> SEQ ID NO 114
<211> LENGTH: 120
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                20                  25                  30

Gly Met Asp Trp Val Arg Gln Ala Pro Gly Lys Gly Leu Glu Trp Val
            35                  40                  45

Ala Val Ile Ser Tyr Asp Gly Arg Asn Lys Asn Tyr Val Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Ser Ala Val Tyr Phe Cys
                85                  90                  95

Ala Lys Glu Gly Gly Leu Gly Thr Trp Tyr Phe Asp Leu Trp Gly Arg
            100                 105                 110

Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct tcagtaccta tggc                                             24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Thr Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atatcatatg atggacgtaa taaa                                           24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Tyr Asp Gly Arg Asn Lys
1               5

<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119
gcgaaagagg ggggactggg gacctggtac ttcgatctc                           39

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Ala Lys Glu Gly Gly Leu Gly Thr Trp Tyr Phe Asp Leu
1               5                   10

<210> SEQ ID NO 121
<211> LENGTH: 339
<212> TYPE: DNA
<213> ORGANISM: Artificial Sequence
<220> FEATURE:
<223> OTHER INFORMATION: Synthetic

<400> SEQUENCE: 121
gacatcgtga tgacccagtc tccagactcc ctggctatgt ctctgggcga gagggccacc    60
atcaactgca gtccagcca gagtgtttta tacaactcca acaataagaa ctacttagtt    120
tggtaccagc agaaatttgg acagcctcct aaactgctca tttactgggc atctacccgg    180

```
gaatccgggg tccctgaccg gttcagtggc agcgggtctg ggacagattt cactctcacc    240
atcagcagcc tgcaggctga agatgtggca gtttattact gtcaacaata tcatagtact    300
ccgtacacct ttggccaggg gaccaagctg gagatcaaa                           339
```

<210> SEQ ID NO 122
<211> LENGTH: 113
<212> TYPE: PRT
<213> ORGANISM: Artificial Sequence
<220> FEATURE:
<223> OTHER INFORMATION: Synthetic

<400> SEQUENCE: 122

```
Asp Ile Val Met Thr Gln Ser Pro Asp Ser Leu Ala Met Ser Leu Gly
 1               5                  10                  15

Glu Arg Ala Thr Ile Asn Cys Lys Ser Ser Gln Ser Val Leu Tyr Asn
            20                  25                  30

Ser Asn Asn Lys Asn Tyr Leu Val Trp Tyr Gln Gln Lys Phe Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr His Ser Thr Pro Tyr Thr Phe Gly Gln Gly Thr Lys Leu Glu Ile
            100                 105                 110

Lys
```

<210> SEQ ID NO 123
<211> LENGTH: 36
<212> TYPE: DNA
<213> ORGANISM: Artificial Sequence
<220> FEATURE:
<223> OTHER INFORMATION: Synthetic

<400> SEQUENCE: 123

```
cagagtgttt tatacaactc caacaataag aactac                               36
```

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

```
Gln Ser Val Leu Tyr Asn Ser Asn Asn Lys Asn Tyr
 1               5                  10
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125

```
tgggcatct                                                             9
```

<210> SEQ ID NO 126
<211> LENGTH: 3

```
<212> TYPE: PRT
<213> ORGANISM: Artificial Sequence
<220> FEATURE:
<223> OTHER INFORMATION: Synthetic

<400> SEQUENCE: 126

Trp Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacaatatc atagtactcc gtacacc                                          27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr His Ser Thr Pro Tyr Thr
 1               5

<210> SEQ ID NO 129
<211> LENGTH: 345
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggc ttggtccagc ctggggggtc cctgagactc        60
tcctgtgcag cctctggatt cacctttagt agctattgga tgagctgggt ccgccaggct       120
ccagggaagg ggctggagtg ggtggccaac ataaagcaag atggaagtga aaaatactat       180
gtggactctg tgaagggccg attcaccatc tccagagaca acgccaagaa ctcactgaat       240
cttcaaatga acagcctgag agccgaggac acggctttat attactgtgc gagaggtatt       300
acgattttct ctggggcca gggaaccctg gtcaccgtct cctca                       345

<210> SEQ ID NO 130
<211> LENGTH: 115
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60
```

```
Lys Gly Arg Phe Thr Ile Ser Arg Asp Asn Ala Lys Asn Ser Leu Asn
 65                  70                  75                  80

Leu Gln Met Asn Ser Leu Arg Ala Glu Asp Thr Ala Leu Tyr Tyr Cys
                 85                  90                  95

Ala Arg Gly Ile Thr Ile Phe Phe Trp Gly Gln Gly Thr Leu Val Thr
            100                 105                 110

Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ttagtagcta ttgg                                           24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Ser Tyr Trp
  1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
ataaagcaag atggaagtga gaaa                                           24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Lys Gln Asp Gly Ser Glu Lys
  1               5

<210> SEQ ID NO 135
<211> LENGTH: 24
<212> TYPE: DNA
<213> ORGANISM: Artificial Sequence
<220> FEATURE:
<223> OTHER INFORMATION: Synthetic

<400> SEQUENCE: 135
gcgagaggta ttacgatttt cttc                                           24

<210> SEQ ID NO 136
<211> LENGTH: 8
<212> TYPE: PRT
<213> ORGANISM: Artificial Sequence
```

<220> FEATURE:
<223> OTHER INFORMATION: Synthetic

<400> SEQUENCE: 136

Ala Arg Gly Ile Thr Ile Phe Phe
1               5

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaaaag agttacagta ccccgtacac ttttggccag     300
gggaccaagc tggagatcaa a                                              321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ser Tyr Ser Thr Pro Tyr
                85                  90                  95

Thr Phe Gly Gln Gly Thr Lys Leu Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagagcatta gcagctat                                                   18

<210> SEQ ID NO 140
<211> LENGTH: 6
<212> TYPE: PRT
<213> ORGANISM: Artificial Sequence
<220> FEATURE:

<223> OTHER INFORMATION: Synthetic

<400> SEQUENCE: 140

Gln Ser Ile Ser Ser Tyr
 1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc                                                                 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caaaagagtt acagtacccc gtacact                                            27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Lys Ser Tyr Ser Thr Pro Tyr Thr
 1               5

<210> SEQ ID NO 145
<211> LENGTH: 351
<212> TYPE: DNA
<213> ORGANISM: Artificial Sequence
<220> FEATURE:
<223> OTHER INFORMATION: Synthetic

<400> SEQUENCE: 145
caggtgcagc tggtggagtc tgggggaggc ttggtcaagc ctggagggtc cctgagactc        60
tcctgtgcag cctctggatt caccttcagt gactactata tgagttggat ccgccaggct       120
ccagggaagg ggctggagtg ggtttcatat attagtacta gtggtagtac catatactac       180
ccagactctg tgaagggccg attcaccatc tccagggaca acgccaagaa ctcactgaat       240
ctgcaaatga acagcctgag agccgaggac acggccgtat attattgcct actccactac       300
tactacggta tggacgtctg gggccaaggg accacggtca ccgtctcctc a                351

<210> SEQ ID NO 146
<211> LENGTH: 117
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Thr Ser Gly Ser Thr Ile Tyr Pro Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Leu Leu His Tyr Tyr Tyr Gly Met Asp Val Trp Gly Gln Gly Thr Thr
            100                 105                 110

Val Thr Val Ser Ser
        115

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtgacta ctat                                         24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Asp Tyr Tyr
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtacta gtggtagtac cata                                         24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Thr Ser Gly Ser Thr Ile
 1               5

<210> SEQ ID NO 151
<211> LENGTH: 30
<212> TYPE: DNA
<213> ORGANISM: Artificial Sequence
<220> FEATURE:
<223> OTHER INFORMATION: Synthetic

<400> SEQUENCE: 151
ctactccact actactacgg tatggacgtc                                    30

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Leu Leu His Tyr Tyr Tyr Gly Met Asp Val
 1               5                  10

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gaaattgtgt tgacacagtc tccagccacc ctgtctttgt ctccagggga aagagccccc    60
ctctcctgca gggccagtca gagtgttagc agctacttag cctggtacca gcagaaacct   120
ggccaacctc ccaggctcct catctatgat gcatccaaca gggccactgg catcccagcc   180
agattcagtg gcagtgggtc tgggacagac ttcactctca ccatcagcag cctcgagcct   240
gaagattttg cagtttatta ctgtcagcag cgtagcaact ggccgtggac gttcggccaa   300
gggaccaagg tggaaatcaa a                                             321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Glu Ile Val Leu Thr Gln Ser Pro Ala Thr Leu Ser Leu Ser Pro Gly
 1               5                  10                  15

Glu Arg Ala Pro Leu Ser Cys Arg Ala Ser Gln Ser Val Ser Ser Tyr
            20                  25                  30

Leu Ala Trp Tyr Gln Gln Lys Pro Gly Gln Pro Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagagtgtta gcagctac                                              18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Ser Val Ser Ser Tyr
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gatgcatcc                                                         9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Asp Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
cagcagcgta gcaactggcc gtggacg                                    27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Arg Ser Asn Trp Pro Trp Thr
 1               5

<210> SEQ ID NO 161
<211> LENGTH: 357
<212> TYPE: DNA
<213> ORGANISM: Artificial Sequence
<220> FEATURE:
<223> OTHER INFORMATION: Synthetic

<400> SEQUENCE: 161

```
gaagtgcagc tggtggagtc tgggggaggc ttggtacagc ctggcaggtc cctgagactc      60
tcctgtgcag cctctggatt cacctttgat gaatatgcca tgcactgggt ccggcaagtt     120
ccagggaagg gcctggagtg ggtctcaggc attagtcgga atagtggtac cataggctat     180
gtggactctg tgctgggccg attcaccatc tccagagaca acgccaagaa ctccctgtat     240
ctgcaaatga acagtctgag acctgaggac acggccttgt attactgtgc aaaagataag     300
gggtggctac tcggtatgga cgtctggggc caagggacca cggtcaccgt ctcctca       357
```

<210> SEQ ID NO 162
<211> LENGTH: 119
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Ala Met His Trp Val Arg Gln Val Pro Gly Lys Gly Leu Glu Trp Val
        35                  40                  45

Ser Gly Ile Ser Arg Asn Ser Gly Thr Ile Gly Tyr Val Asp Ser Val
    50                  55                  60

Leu Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Asp Lys Gly Trp Leu Leu Gly Met Asp Val Trp Gly Gln Gly
            100                 105                 110

Thr Thr Val Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
ggattcacct ttgatgaata tgcc                                              24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Asp Glu Tyr Ala

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attagtcgga atagtggtac cata                                         24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Arg Asn Ser Gly Thr Ile
1               5

<210> SEQ ID NO 167
<211> LENGTH: 36
<212> TYPE: DNA
<213> ORGANISM: Artificial Sequence
<220> FEATURE:
<223> OTHER INFORMATION: Synthetic

<400> SEQUENCE: 167
gcaaaagata aggggtggct actcggtatg gacgtc                            36

<210> SEQ ID NO 168
<211> LENGTH: 12
<212> TYPE: PRT
<213> ORGANISM: Artificial Sequence
<220> FEATURE:
<223> OTHER INFORMATION: Synthetic

<400> SEQUENCE: 168

Ala Lys Asp Lys Gly Trp Leu Leu Gly Met Asp Val
1               5                   10

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtaggaga cagagtcacc    60
atcacttgcc gggcaagtca ggccattaga aatgatttag ctggtatca gcagaaacca   120 gggaaagccc ctaagcgcct gatctatgct gcatccagtc tgcaaagtgg ggtcccatca   180
aggttcagcg gcagtggatc tgggacagaa ttcgctctca caatcagcag cctgcagcct   240
gaagattttg caacttatta ctgtctacag tacaatagtt atctgtacac ttttggccag   300
gggaccaagc tggagatcaa a                                             321

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ala Leu Thr Ile Ser Ser Leu Gln Pro
65                  70                  75                  80

Glu Asp Phe Ala Thr Tyr Tyr Cys Leu Gln Tyr Asn Ser Tyr Leu Tyr
                85                  90                  95

Thr Phe Gly Gln Gly Thr Lys Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
caggccatta gaaatgat                                                 18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Ala Ile Arg Asn Asp
1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcatcc                                                            9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1

<210> SEQ ID NO 175
<211> LENGTH: 27

<212> TYPE: DNA
<213> ORGANISM: Artificial Sequence
<220> FEATURE:
<223> OTHER INFORMATION: Synthetic

<400> SEQUENCE: 175
ctacagtaca atagttatct gtacact     27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Leu Gln Tyr Asn Ser Tyr Leu Tyr Thr
 1               5

<210> SEQ ID NO 177
<211> LENGTH: 369
<212> TYPE: DNA
<213> ORGANISM: Artificial Sequence
<220> FEATURE:
<223> OTHER INFORMATION: Synthetic

<400> SEQUENCE: 177
caggtgcagc tgcaggagtc gggcccagga ctggtgaagc cttcacagac cctgtccctc     60
acctgcactg tctctggtgg ctccatcagc agtgatggtt actactggag ctggatccgc    120
cagcacccag ggaagggcct ggagtggatt ggttacatct attacagtgg gaacacctac    180
tacaacccgt ccctcaagag tcgagttacc atatcagttg acacgtctaa gaaccacttc    240
tccctgaaac tgagctctgt gactgccgcg gacacggccg tgtattactg tacgagagat    300
ccccgcggta taactggaac ccactacttt gactactggg gccagggaac cctggtcacc    360
gtctcctca                                                            369

<210> SEQ ID NO 178
<211> LENGTH: 123
<212> TYPE: PRT
<213> ORGANISM: Artificial Sequence
<220> FEATURE:
<223> OTHER INFORMATION: Synthetic

<400> SEQUENCE: 178

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Asp
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn His Phe
65                  70                  75                  80

Ser Leu Lys Leu Ser Ser Val Thr Ala Ala Asp Thr Ala Val Tyr Tyr
                85                  90                  95

Cys Thr Arg Asp Pro Arg Gly Ile Thr Gly Thr His Tyr Phe Asp Tyr
            100                 105                 110

Trp Gly Gln Gly Thr Leu Val Thr Val Ser Ser
        115                 120

<210> SEQ ID NO 179
<211> LENGTH: 30
<212> TYPE: DNA
<213> ORGANISM: Artificial Sequence
<220> FEATURE:
<223> OTHER INFORMATION: Synthetic

<400> SEQUENCE: 179
ggtggctcca tcagcagtga tggttactac            30

<210> SEQ ID NO 180
<211> LENGTH: 10
<212> TYPE: PRT
<213> ORGANISM: Artificial Sequence
<220> FEATURE:
<223> OTHER INFORMATION: Synthetic

<400> SEQUENCE: 180

Gly Gly Ser Ile Ser Ser Asp Gly Tyr Tyr
 1               5                  10

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
atctattaca gtgggaacac c            21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Ile Tyr Tyr Ser Gly Asn Thr
 1               5

<210> SEQ ID NO 183
<211> LENGTH: 45
<212> TYPE: DNA
<213> ORGANISM: Artificial Sequence
<220> FEATURE:
<223> OTHER INFORMATION: Synthetic

<400> SEQUENCE: 183
acgagagatc cccgcggtat aactggaacc cactactttg actac            45

<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

Thr Arg Asp Pro Arg Gly Ile Thr Gly Thr His Tyr Phe Asp Tyr
 1               5                  10                  15

<210> SEQ ID NO 185
<211> LENGTH: 324

<212> TYPE: DNA
<213> ORGANISM: Artificial Sequence
<220> FEATURE:
<223> OTHER INFORMATION: Synthetic

<400> SEQUENCE: 185

```
gaaattgtgt tgacgcagtc tccaggcacc ctgtctttgt ctccagggga aagagccacc      60
ctctcctgca ggaccagtca gagtgttagc agcagctacc tagcctggta ccagcagaaa     120
cctggccagg ctcccaggct cctcatctat ggtgcatcca gcagggccac tggcatccca     180
gacaggttca gtggcagtgg gtctggaaca gacttcactc tcaccatcag cagactggag     240
cctgaagatt ttgcagtata ttactgtcag cagtttggta cttcactatt cactttcggc     300
cctgggacca agtggatat caaa                                             324
```

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

```
Glu Ile Val Leu Thr Gln Ser Pro Gly Thr Leu Ser Leu Ser Pro Gly
 1               5                  10                  15

Glu Arg Ala Thr Leu Ser Cys Arg Thr Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Thr Ser Leu
                85                  90                  95

Phe Thr Phe Gly Pro Gly Thr Lys Val Asp Ile Lys
            100                 105
```

<210> SEQ ID NO 187
<211> LENGTH: 21
<212> TYPE: DNA
<213> ORGANISM: Artificial Sequence
<220> FEATURE:
<223> OTHER INFORMATION: Synthetic

<400> SEQUENCE: 187

```
cagagtgtta gcagcagcta c                                               21
```

<210> SEQ ID NO 188
<211> LENGTH: 7
<212> TYPE: PRT
<213> ORGANISM: Artificial Sequence
<220> FEATURE:
<223> OTHER INFORMATION: Synthetic

<400> SEQUENCE: 188

```
Gln Ser Val Ser Ser Ser Tyr
 1               5
```

<210> SEQ ID NO 189
<211> LENGTH: 9
<212> TYPE: DNA

<213> ORGANISM: Artificial Sequence
<220> FEATURE:
<223> OTHER INFORMATION: Synthetic

<400> SEQUENCE: 189 ggtgcatcc                                                                                      9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Gly Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
cagcagtttg gtacttcact attcact                                                                 27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Phe Gly Thr Ser Leu Phe Thr
 1               5

<210> SEQ ID NO 193
<211> LENGTH: 360
<212> TYPE: DNA
<213> ORGANISM: Artificial Sequence
<220> FEATURE:
<223> OTHER INFORMATION: Synthetic

<400> SEQUENCE: 193
caggtgcagc tggtggagtc tgggggaggc gtggtccagc ctggggaggtc cctgagactc         60 tcctgcgcag cctctggatt caccttcagt agatttggca tggactgggt ccgccaggct        120
ccaggcaagg ggctggagtg ggtggcagtt atatcatatg atggaaaaaa taaactttat        180
gcagactccg tgaagggccg attcaccatc tccagagaca attccaagaa cacgctgtat        240
atgcaaatga acagcctgcg agctgaggac acggctgtat attactgtgc gaaagaggga        300
gataactgga acttcgtggg ggactcctgg ggccagggaa ccctggtcac cgtctcctca        360

<210> SEQ ID NO 194
<211> LENGTH: 120
<212> TYPE: PRT
<213> ORGANISM: Artificial Sequence
<220> FEATURE:
<223> OTHER INFORMATION: Synthetic

<400> SEQUENCE: 194

Gln Val Gln Leu Val Glu Ser Gly Gly Gly Val Val Gln Pro Gly Arg

```
            1               5                  10                 15
Ser Leu Arg Leu Ser Cys Ala Ala Ser Gly Phe Thr Phe Ser Arg Phe
                20                  25                 30

Gly Met Asp Trp Val Arg Gln Ala Pro Gly Lys Gly Leu Glu Trp Val
            35                  40                 45

Ala Val Ile Ser Tyr Asp Gly Lys Asn Lys Leu Tyr Ala Asp Ser Val
        50                  55                 60

Lys Gly Arg Phe Thr Ile Ser Arg Asp Asn Ser Lys Asn Thr Leu Tyr
65                  70                  75                 80

Met Gln Met Asn Ser Leu Arg Ala Glu Asp Thr Ala Val Tyr Tyr Cys
                85                  90                 95

Ala Lys Glu Gly Asp Asn Trp Asn Phe Val Gly Asp Ser Trp Gly Gln
            100                 105                110

Gly Thr Leu Val Thr Val Ser Ser
        115                 120
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct tcagtagatt tggc                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Ser Arg Phe Gly
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
atatcatatg atggaaaaaa taaa                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Tyr Asp Gly Lys Asn Lys
1               5

<210> SEQ ID NO 199
<211> LENGTH: 39
<212> TYPE: DNA
<213> ORGANISM: Artificial Sequence
<220> FEATURE:

<223> OTHER INFORMATION: Synthetic

<400> SEQUENCE: 199
gcgaaagagg gagataactg gaacttcgtg ggggactcc        39

<210> SEQ ID NO 200
<211> LENGTH: 13
<212> TYPE: PRT
<213> ORGANISM: Artificial Sequence
<220> FEATURE:
<223> OTHER INFORMATION: Synthetic

<400> SEQUENCE: 200

Ala Lys Glu Gly Asp Asn Trp Asn Phe Val Gly Asp Ser
1               5                   10

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcttcc gtgtctgcat ctgtgggaga cagagtcacc        60
atcacttgtc gggcgagtca ggatattagt gccaggttag cctggtatca gcagaaacca       120
gggaaagccc ctaaactcct gatctatgct gcatccagtt tgcaaagtgg ggtcccatca       180
aggttcagcg gcagtggatc tgggacagat tcactctca ccatcagtag cctggagcct        240
gaagattttg caacttacta ttgtcaacag gctgacagtt tcccgtacac tttgggccag       300
gggaccaagc tggagatcaa a                                                 321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ala Arg
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ala Asp Ser Phe Pro Tyr
                85                  90                  95

Thr Leu Gly Gln Gly Thr Lys Leu Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
caggatatta gtgccagg                                                          18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Asp Ile Ser Ala Arg
 1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcatcc                                                                     9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacaggctg acagtttccc gtacact                                                27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Ala Asp Ser Phe Pro Tyr Thr
 1               5

<210> SEQ ID NO 209
<211> LENGTH: 360
<212> TYPE: DNA
<213> ORGANISM: Artificial Sequence
<220> FEATURE:
<223> OTHER INFORMATION: Synthetic

<400> SEQUENCE: 209
caggtgcagc tggtggagtc tgggggaggc gtggtccagc ctggggaggtc cctgagactc          60

| | | | | |
|---|---|---|---|---|
| tcctgcgcag | cctctggatt | caccttcagt | agatttggca | tggactgggt ccgccaggct | 120 |
| ccaggcaagg | ggctggagtg | ggtggcagtt | atttcatatg | atggaaaaaa taaactttat | 180 |
| gcagactccg | tgaagggccg | attcaccatc | tccagagaca | attccaagaa cacgctgtat | 240 |
| ctgcaaatga | acagcctgag | agctgaggac | acggctgtgt | attactgtgc gaaagaggga | 300 |
| gataactgga | acttcgtggg | ggactcctgg | ggccagggaa | ccctggtcac cgtctcctca | 360 |

```
<210> SEQ ID NO 210
<211> LENGTH: 120
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Phe
             20                  25                  30

Gly Met Asp Trp Val Arg Gln Ala Pro Gly Lys Gly Leu Glu Trp Val
         35                  40                  45

Ala Val Ile Ser Tyr Asp Gly Lys Asn Lys Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Asp Asn Trp Asn Phe Val Gly Asp Ser Trp Gly Gln
            100                 105                 110

Gly Thr Leu Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct tcagtagatt tggc                                           24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Arg Phe Gly
 1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
```

```
atttcatatg atggaaaaaa taaa                                            24
```

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Tyr Asp Gly Lys Asn Lys
1               5

<210> SEQ ID NO 215
<211> LENGTH: 39
<212> TYPE: DNA
<213> ORGANISM: Artificial Sequence
<220> FEATURE:
<223> OTHER INFORMATION: Synthetic

<400> SEQUENCE: 215

```
gcgaaagagg gagataactg gaacttcgtg ggggactcc                             39
```

<210> SEQ ID NO 216
<211> LENGTH: 13
<212> TYPE: PRT
<213> ORGANISM: Artificial Sequence
<220> FEATURE:
<223> OTHER INFORMATION: Synthetic

<400> SEQUENCE: 216

Ala Lys Glu Gly Asp Asn Trp Asn Phe Val Gly Asp Ser
1               5                   10

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217

```
gacatccaga tgacccagtc tccatcttcc gtgtctgcat ctgtaggaga cagagtcacc     60
atcacttgtc gggcgagtca gggtattagt gccaggttag cctggtatca gcagaaacca    120
gggaaagccc ctaaactcct gatctatgct gcatccagtt tgcaaagtgg ggtcccatca    180
aggttcagcg gcagtggatc tgggacatat ttcactctca ccatcagtaa cctgcagcct    240
gaagattttg caacttacta ttgtcaacag gctaacagtt tcccgtacac tttaggccag    300
gggaccaagc tggagatcaa a                                              321
```

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ala Arg
            20                  25                  30

-continued

```
Leu Ala Trp Tyr Gln Gln Lys Pro Gly Lys Ala Pro Lys Leu Leu Ile
             35                  40                  45
Tyr Ala Ala Ser Ser Leu Gln Ser Gly Val Pro Ser Arg Phe Ser Gly
 50                  55                  60
Ser Gly Ser Gly Thr Tyr Phe Thr Leu Thr Ile Ser Asn Leu Gln Pro
 65                  70                  75                  80
Glu Asp Phe Ala Thr Tyr Tyr Cys Gln Gln Ala Asn Ser Phe Pro Tyr
                 85                  90                  95
Thr Leu Gly Gln Gly Thr Lys Leu Glu Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagggtatta gtgccagg                                               18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Gly Ile Ser Ala Arg
 1               5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gctgcatcc                                                          9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Ala Ala Ser
 1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacaggcta acagtttccc gtacact                                     27

<210> SEQ ID NO 224

<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Ala Asn Ser Phe Pro Tyr Thr
1               5

<210> SEQ ID NO 225
<211> LENGTH: 369
<212> TYPE: DNA
<213> ORGANISM: Artificial Sequence
<220> FEATURE:
<223> OTHER INFORMATION: Synthetic

<400> SEQUENCE: 225

```
gaagtgcagc tggtggagtc gggcccagga ctggtgaagc cttcacagac cctgtccctc      60
acctgcactg tctctggtgg ctccatcaac agtggtggtt cctattggag ttggatccgc     120
cagcacccag ggaagggcct ggagtggatt gggtacatct attccagtgg gaacacctac     180
tacaagccgt ccctcaagag tcgagttacc atatcactag acacgtctaa gaaccagttc     240
tccctgaaga tgagctctgt gactgccgcg gacacggcca tatattactg tgcgagagat     300
ccccgcggta taactggaac ccactacttt gattactggg gccagggaac cacggtcacc     360
gtctcctca                                                             369
```

<210> SEQ ID NO 226
<211> LENGTH: 123
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Ser Tyr Trp Ser Trp Ile Arg Gln His Pro Gly Lys Gly Leu Glu
        35                  40                  45

Trp Ile Gly Tyr Ile Tyr Ser Ser Gly Asn Thr Tyr Tyr Lys Pro Ser
    50                  55                  60

Leu Lys Ser Arg Val Thr Ile Ser Leu Asp Thr Ser Lys Asn Gln Phe
65                  70                  75                  80

Ser Leu Lys Met Ser Ser Val Thr Ala Ala Asp Thr Ala Ile Tyr Tyr
                85                  90                  95

Cys Ala Arg Asp Pro Arg Gly Ile Thr Gly Thr His Tyr Phe Asp Tyr
            100                 105                 110

Trp Gly Gln Gly Thr Thr Val Thr Val Ser Ser
        115                 120

<210> SEQ ID NO 227
<211> LENGTH: 30
<212> TYPE: DNA
<213> ORGANISM: Artificial Sequence
<220> FEATURE:
<223> OTHER INFORMATION: Synthetic

<400> SEQUENCE: 227

```
ggtggctcca tcaacagtgg tggttcctat                                         30
```

<210> SEQ ID NO 228
<211> LENGTH: 10
<212> TYPE: PRT
<213> ORGANISM: Artificial Sequence
<220> FEATURE:
<223> OTHER INFORMATION: Synthetic

<400> SEQUENCE: 228

```
Gly Gly Ser Ile Asn Ser Gly Gly Ser Tyr
 1               5                  10
```

<210> SEQ ID NO 229
<211> LENGTH: 21
<212> TYPE: DNA
<213> ORGANISM: Artificial Sequence
<220> FEATURE:
<223> OTHER INFORMATION: Synthetic

<400> SEQUENCE: 229

```
atctattcca gtgggaacac c                                                  21
```

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

```
Ile Tyr Ser Ser Gly Asn Thr
 1               5
```

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231

```
gcgagagatc cccgcggtat aactggaacc cactactttg attac              45
```

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

```
Ala Arg Asp Pro Arg Gly Ile Thr Gly Thr His Tyr Phe Asp Tyr
 1               5                  10                  15
```

<210> SEQ ID NO 233
<211> LENGTH: 324
<212> TYPE: DNA
<213> ORGANISM: Artificial Sequence
<220> FEATURE:
<223> OTHER INFORMATION: Synthetic

<400> SEQUENCE: 233

```
gaaattgtgt tgacacagtc tccaggcacc ctgtctttgt ctccagggga aagagccacc        60
ctctcctgca ggaccagtca gagtattagc aacaaatact tggcctggta ccaacagaaa       120
```

```
cctggccagg ctcccaggct cctcatctat ggtgcatcca ccagggccac tggcatccca    180
gacaggttca gtggcagtgg gtctgggaca gacttcactc tcaccatcag cagactggag    240
cctgaagatt ttgcagttta ttactgtcag cagtttggta cctcactatt cactttcggc    300
cctgggacca aggtggagat caaa                                           324
```

```
<210> SEQ ID NO 234
<211> LENGTH: 108
<212> TYPE: PRT
<213> ORGANISM: Artificial Sequence
<220> FEATURE:
<223> OTHER INFORMATION: Synthetic

<400> SEQUENCE: 234
```

Glu Ile Val Leu Thr Gln Ser Pro Gly Thr Leu Ser Leu Ser Pro Gly
1               5                   10                  15

Glu Arg Ala Thr Leu Ser Cys Arg Thr Ser Gln Ser Ile Ser Asn Lys
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Thr Ser Leu
                85                  90                  95

Phe Thr Phe Gly Pro Gly Thr Lys Val Glu Ile Lys
            100                 105

```
<210> SEQ ID NO 235
<211> LENGTH: 21
<212> TYPE: DNA
<213> ORGANISM: Artificial Sequence
<220> FEATURE:
<223> OTHER INFORMATION: Synthetic

<400> SEQUENCE: 235
cagagtatta gcaacaaata c                                              21

<210> SEQ ID NO 236
<211> LENGTH: 7
<212> TYPE: PRT
<213> ORGANISM: Artificial Sequence
<220> FEATURE:
<223> OTHER INFORMATION: Synthetic

<400> SEQUENCE: 236
```

Gln Ser Ile Ser Asn Lys Tyr
1               5

```
<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 ggtgcatcc                                                             9

<210> SEQ ID NO 238
<211> LENGTH: 3
```

```
<212> TYPE: PRT
<213> ORGANISM: Artificial Sequence
<220> FEATURE:
<223> OTHER INFORMATION: Synthetic

<400> SEQUENCE: 238

Gly Ala Ser
 1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
cagcagtttg gtacctcact attcact                                         27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Phe Gly Thr Ser Leu Phe Thr
 1               5

<210> SEQ ID NO 241
<211> LENGTH: 360
<212> TYPE: DNA
<213> ORGANISM: Artificial Sequence
<220> FEATURE:
<223> OTHER INFORMATION: Synthetic

<400> SEQUENCE: 241
caggtgcagc tggtgcagtc tgggactgag gtgaagaagc ctggggccgc agtgagggtc      60
tcctgcaagg cttctggata caccttcacc gactaccata tgcactgggt acgacaggcc     120
cctggacaag gcttgagtg gatgggatgg atcaaccta acagtggtgg cacaaactct       180
gcacagaagt ttcagggcag ggtcaccatg accaggggaca cgtccatcag cacagcctac    240
atggagctga acgggctgag atctgacgac acggccgtct attactgtgc gagaaaggcc    300
gggtatacca gtagctggtt cgactactgg ggccagggaa ccacggtcac cgtctcctca    360

<210> SEQ ID NO 242
<211> LENGTH: 120
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Gln Ser Gly Thr Glu Val Lys Lys Pro Gly Ala
 1               5                  10                  15

Ala Val Arg Val Ser Cys Lys Ala Ser Gly Tyr Thr Phe Thr Asp Tyr
             20                  25                  30

His Met His Trp Val Arg Gln Ala Pro Gly Gln Gly Leu Glu Trp Met
         35                  40                  45

Gly Trp Ile Asn Pro Asn Ser Gly Gly Thr Asn Ser Ala Gln Lys Phe
     50                  55                  60
```

Gln Gly Arg Val Thr Met Thr Arg Asp Thr Ser Ile Ser Thr Ala Tyr
65                  70                  75                  80

Met Glu Leu Asn Gly Leu Arg Ser Asp Thr Ala Val Tyr Tyr Cys
                85                  90                  95

Ala Arg Lys Ala Gly Tyr Thr Ser Ser Trp Phe Asp Tyr Trp Gly Gln
            100                 105                 110

Gly Thr Thr Val Thr Val Ser Ser
            115             120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggatacacct tcaccgacta ccat                                          24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Tyr Thr Phe Thr Asp Tyr His
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atcaacccta acagtggtgg caca                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Asn Pro Asn Ser Gly Gly Thr
1               5

<210> SEQ ID NO 247
<211> LENGTH: 39
<212> TYPE: DNA
<213> ORGANISM: Artificial Sequence
<220> FEATURE:
<223> OTHER INFORMATION: Synthetic

<400> SEQUENCE: 247
gcgagaaagg ccgggtatac cagtagctgg ttcgactac                          39

<210> SEQ ID NO 248
<211> LENGTH: 13
<212> TYPE: PRT
<213> ORGANISM: Artificial Sequence
<220> FEATURE:
<223> OTHER INFORMATION: Synthetic

<400> SEQUENCE: 248

Ala Arg Lys Ala Gly Tyr Thr Ser Ser Trp Phe Asp Tyr
1               5                   10

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249

```
gacatcgtga tgacccagtc tccagactcc ctggctgtgt ctctgggcga gagggccacc    60
atcaactgca agtccagcca gagtgtttta tacagcttca acaataagaa ctacttaact   120
tggtaccagc agaaaccagg acagcctcct aagctgctca tttactgggc atctactcgg   180
gaatccgggg tccctgaccg attcagtggc agcgggtctg ggacagattt cactctcacc   240
atcagcagcc tgcaggctga agatgtggca gtttattact gtcagcaata ttatagtctg   300
atcactttcg gccaagggac acgactggag attaaa                             336
```

<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Phe Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Leu Ile Thr Phe Gly Gln Gly Thr Arg Leu Glu Ile Lys
            100                 105                 110

<210> SEQ ID NO 251
<211> LENGTH: 36
<212> TYPE: DNA
<213> ORGANISM: Artificial Sequence
<220> FEATURE:
<223> OTHER INFORMATION: Synthetic

<400> SEQUENCE: 251

```
cagagtgttt tatacagctt caacaataag aactac                              36
```

<210> SEQ ID NO 252
<211> LENGTH: 12
<212> TYPE: PRT
<213> ORGANISM: Artificial Sequence
<220> FEATURE:

```
<223> OTHER INFORMATION: Synthetic

<400> SEQUENCE: 252

Gln Ser Val Leu Tyr Ser Phe Asn Asn Lys Asn Tyr
 1               5                  10

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 tgggcatct                                                                  9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Trp Ala Ser
 1

<210> SEQ ID NO 255
<211> LENGTH: 24
<212> TYPE: DNA
<213> ORGANISM: Artificial Sequence
<220> FEATURE:
<223> OTHER INFORMATION: Synthetic

<400> SEQUENCE: 255
cagcaatatt atagtctgat cact                                                24

<210> SEQ ID NO 256
<211> LENGTH: 8
<212> TYPE: PRT
<213> ORGANISM: Artificial Sequence
<220> FEATURE:
<223> OTHER INFORMATION: Synthetic

<400> SEQUENCE: 256

Gln Gln Tyr Tyr Ser Leu Ile Thr
 1               5

<210> SEQ ID NO 257
<211> LENGTH: 369
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc gggcccagga ctggtgaagc tgcacagac cctgtctctc          60 acctgtactg tctctggtgg ctccatcaac agtggtggta attactggag ttggatccgc        120
cagcacccag ggaagggcct ggagtggatt gggtacatct attacagtgg gaacacctac        180
tacaacccgt ccctcaagag tcgagttacc atatcagtag acatgtctaa gaaccagttc        240
tccctgaaac tgaggtctgt gactgcggcg gacacggccg tgtatttctg tgcgagagat        300
ccccgcggta taactggaac ccaccacttt gactgctggg gccagggaac cctggtcact        360
``` gtctcctca                                                             369

<210> SEQ ID NO 258
<211> LENGTH: 123
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Glu Ser Gly Pro Gly Leu Val Lys Pro Ala Gln
 1               5                  10                  15

Thr Leu Ser Leu Thr Cys Thr Val Ser Gly Gly Ser Ile Asn Ser Gly
            20                  25                  30

Gly Asn Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Val Asp Met Ser Lys Asn Gln Phe
65                  70                  75                  80

Ser Leu Lys Leu Arg Ser Val Thr Ala Ala Asp Thr Ala Val Tyr Phe
                85                  90                  95

Cys Ala Arg Asp Pro Arg Gly Ile Thr Gly Thr His His Phe Asp Cys
            100                 105                 110

Trp Gly Gln Gly Thr Leu Val Thr Val Ser Ser
        115                 120

<210> SEQ ID NO 259
<211> LENGTH: 30
<212> TYPE: DNA
<213> ORGANISM: Artificial Sequence
<220> FEATURE:
<223> OTHER INFORMATION: Synthetic

<400> SEQUENCE: 259
ggtggctcca tcaacagtgg tggtaattac                                       30

<210> SEQ ID NO 260
<211> LENGTH: 10
<212> TYPE: PRT
<213> ORGANISM: Artificial Sequence
<220> FEATURE:
<223> OTHER INFORMATION: Synthetic

<400> SEQUENCE: 260

Gly Gly Ser Ile Asn Ser Gly Gly Asn Tyr
 1               5                  10

<210> SEQ ID NO 261
<211> LENGTH: 21
<212> TYPE: DNA
<213> ORGANISM: Artificial Sequence
<220> FEATURE:
<223> OTHER INFORMATION: Synthetic

<400> SEQUENCE: 261
atctattaca gtgggaacac c                                                21

<210> SEQ ID NO 262
<211> LENGTH: 7
<212> TYPE: PRT
<213> ORGANISM: Artificial Sequence
<220> FEATURE:

```
<223> OTHER INFORMATION: Synthetic

<400> SEQUENCE: 262

Ile Tyr Tyr Ser Gly Asn Thr
1               5

<210> SEQ ID NO 263
<211> LENGTH: 45
<212> TYPE: DNA
<213> ORGANISM: Artificial Sequence
<220> FEATURE:
<223> OTHER INFORMATION: Synthetic

<400> SEQUENCE: 263
gcgagagatc cccgcggtat aactggaacc caccactttg actgc            45

<210> SEQ ID NO 264
<211> LENGTH: 15
<212> TYPE: PRT
<213> ORGANISM: Artificial Sequence
<220> FEATURE:
<223> OTHER INFORMATION: Synthetic

<400> SEQUENCE: 264

Ala Arg Asp Pro Arg Gly Ile Thr Gly Thr His His Phe Asp Cys
1               5                   10                  15

<210> SEQ ID NO 265
<211> LENGTH: 324
<212> TYPE: DNA
<213> ORGANISM: Artificial Sequence
<220> FEATURE:
<223> OTHER INFORMATION: Synthetic

<400> SEQUENCE: 265
gaaattgtgt tgacgcagtc tccaggcacc ctgtctttgt ctccagggga aagagccacc    60
ctctcctgca ggacaagtca gagtgttagc agcaggtact tagcctggta ccagcaaaaa   120
cctggccagg ctcccaggct cctcatctat gatgcatcca gcagggccac tggcatccca   180
gacaggttca gtggcagtgg gtctgggaca gacttcactc tcaccatcag cagactggag   240
cctgaagatt ttgcagtgta ttactgtcag cagtttggtc cctcactatt cactttcggc   300
cctgggacca agtggatat caaa                                            324

<210> SEQ ID NO 266
<211> LENGTH: 108
<212> TYPE: PRT
<213> ORGANISM: Artificial Sequence
<220> FEATURE:
<223> OTHER INFORMATION: Synthetic

<400> SEQUENCE: 266

Glu Ile Val Leu Thr Gln Ser Pro Gly Thr Leu Ser Leu Ser Pro Gly
1               5                   10                  15

Glu Arg Ala Thr Leu Ser Cys Arg Thr Ser Gln Ser Val Ser Ser Arg
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Phe Gly Pro Ser Leu
            85                  90                  95

Phe Thr Phe Gly Pro Gly Thr Lys Val Asp Ile Lys
            100                 105

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
cagagtgtta gcagcaggta c                                          21

<210> SEQ ID NO 268
<211> LENGTH: 7
<212> TYPE: PRT
<213> ORGANISM: Artificial Sequence
<220> FEATURE:
<223> OTHER INFORMATION: Synthetic

<400> SEQUENCE: 268

Gln Ser Val Ser Ser Arg Tyr
 1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 gatgcatcc                                                         9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Asp Ala Ser
 1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
cagcagtttg gtccctcact attcact                                    27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Phe Gly Pro Ser Leu Phe Thr

<210> SEQ ID NO 273
<211> LENGTH: 360
<212> TYPE: DNA
<213> ORGANISM: Artificial Sequence
<220> FEATURE:
<223> OTHER INFORMATION: Synthetic

<400> SEQUENCE: 273

```
caggtgcagc tggtgcagtc tggggctgag gtgaagaagc ctggggcctc agtgaaggtc      60
tcctgcaagg cttctggata caccttcacc gactactata tgcactgggt gcgacaggcc     120
cctgggcaag gcttgagtg gataggatgg atcaacccta acagtggtgg ctcaaacttt     180
gcacagaagt ttcagggcag ggtcaccatg accaggaca cgtccatcag cacagcctac     240
atggagctga gcaggctgag atctgacgac acggccgtgt attactgtgc gagaaaggcc     300
gggtatacca gcagctggtt cgactactgg ggccagggaa ccctggtcac tgtctcctca     360
```

<210> SEQ ID NO 274
<211> LENGTH: 120
<212> TYPE: PRT
<213> ORGANISM: Artificial Sequence
<220> FEATURE:
<223> OTHER INFORMATION: Synthetic

<400> SEQUENCE: 274

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Tyr
             20                  25                  30
Tyr Met His Trp Val Arg Gln Ala Pro Gly Gln Gly Leu Glu Trp Ile
         35                  40                  45
Gly Trp Ile Asn Pro Asn Ser Gly Gly Ser Asn Phe Ala Gln Lys Phe
     50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Lys Ala Gly Tyr Thr Ser Ser Trp Phe Asp Tyr Trp Gly Gln
            100                 105                 110
Gly Thr Leu Val Thr Val Ser Ser
        115                 120
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

```
ggatacacct tcaccgacta ctat                                              24
```

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Tyr Thr Phe Thr Asp Tyr Tyr
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
atcaacccta acagtggtgg ctca                                              24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Asn Pro Asn Ser Gly Gly Ser
1               5

<210> SEQ ID NO 279
<211> LENGTH: 39
<212> TYPE: DNA
<213> ORGANISM: Artificial Sequence
<220> FEATURE:
<223> OTHER INFORMATION: Synthetic

<400> SEQUENCE: 279
gcgagaaagg ccgggtatac cagcagctgg ttcgactac                              39

<210> SEQ ID NO 280
<211> LENGTH: 13
<212> TYPE: PRT
<213> ORGANISM: Artificial Sequence
<220> FEATURE:
<223> OTHER INFORMATION: Synthetic

<400> SEQUENCE: 280

Ala Arg Lys Ala Gly Tyr Thr Ser Ser Trp Phe Asp Tyr
1               5                   10

<210> SEQ ID NO 281
<211> LENGTH: 336
<212> TYPE: DNA
<213> ORGANISM: Artificial Sequence
<220> FEATURE:
<223> OTHER INFORMATION: Synthetic

<400> SEQUENCE: 281
gacatcgtga tgacccagtc tccagactcc ctggctgtgt ctctgggcga gagggccacc        60
atcaactgca gtccagcca gagtgtttta tacagcttca acaataagaa ctacttaagt       120
tggtaccagc agaaaccagg acagcctcct aagctgctca tttactgggc atctacccgg       180
gaatccgggg tccctgaccg attcagtggc agcgggtctg ggacagattt cactctcacc       240
atcagcagcc tgcaggctga agatgcggca gtttattact gtcagcaata ttatagtatg       300
atcaccttcg gccaagggac acgactggag attaaa                                 336

<210> SEQ ID NO 282
<211> LENGTH: 112

```
<212> TYPE: PRT
<213> ORGANISM: Artificial Sequence
<220> FEATURE:
<223> OTHER INFORMATION: Synthetic

<400> SEQUENCE: 282

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Phe Asn Asn Lys Asn Tyr Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Ala Ala Val Tyr Tyr Cys Gln Gln
                85                  90                  95

Tyr Tyr Ser Met Ile Thr Phe Gly Gln Gly Thr Arg Leu Glu Ile Lys
            100                 105                 110

<210> SEQ ID NO 283
<211> LENGTH: 36
<212> TYPE: DNA
<213> ORGANISM: Artificial Sequence
<220> FEATURE:
<223> OTHER INFORMATION: Synthetic

<400> SEQUENCE: 283
cagagtgttt tatacagctt caacaataag aactac                              36

<210> SEQ ID NO 284
<211> LENGTH: 12
<212> TYPE: PRT
<213> ORGANISM: Artificial Sequence
<220> FEATURE:
<223> OTHER INFORMATION: Synthetic

<400> SEQUENCE: 284

Gln Ser Val Leu Tyr Ser Phe Asn Asn Lys Asn Tyr
 1               5                  10

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 tgggcatct                                                            9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Trp Ala Ser
 1
```

<210> SEQ ID NO 287
<211> LENGTH: 24
<212> TYPE: DNA
<213> ORGANISM: Artificial Sequence
<220> FEATURE:
<223> OTHER INFORMATION: Synthetic

<400> SEQUENCE: 287
cagcaatatt atagtatgat cacc                                          24

<210> SEQ ID NO 288
<211> LENGTH: 8
<212> TYPE: PRT
<213> ORGANISM: Artificial Sequence
<220> FEATURE:
<223> OTHER INFORMATION: Synthetic

<400> SEQUENCE: 288

Gln Gln Tyr Tyr Ser Met Ile Thr
 1               5

<210> SEQ ID NO 289
<211> LENGTH: 378
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtacagc ctggcaggtc cctgagactc     60
tcctgtgcag cctccggatt cacctttgat gattatgcca tgcactgggt ccggcaaggt    120
ccagggaagg gcctggagtg ggtctcaggt attagttgga atggtagaac catggaccat    180
gcggactctg tgaagggccg attcaccatc tccagagaca cgccaagaa ctccctgtat     240 ctgcaaatga acagtctgag aaatgacgac acggcgtgt atttctgtgc aaaagagggt     300
ataccagtgg ctgggacgta tttccacttc tacggtatgg acgtctgggg ccaagggacc    360
acggtcaccg tctcctca                                                  378

<210> SEQ ID NO 290
<211> LENGTH: 126
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Gly Pro Gly Lys Gly Leu Glu Trp Val
            35                  40                  45

Ser Gly Ile Ser Trp Asn Gly Arg Thr Met Asp His Ala Asp Ser Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Asn Asp Asp Thr Gly Val Tyr Phe Cys
                85                  90                  95

Ala Lys Glu Gly Ile Pro Val Ala Gly Thr Tyr Phe His Phe Tyr Gly
            100                 105                 110

```
Met Asp Val Trp Gly Gln Gly Thr Thr Val Thr Val Ser Ser
        115                 120                 125
```

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttgatgatta tgcc                                              24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

```
Gly Phe Thr Phe Asp Asp Tyr Ala
1               5
```

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagttgga atggtagaac catg                                              24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

```
Ile Ser Trp Asn Gly Arg Thr Met
1               5
```

<210> SEQ ID NO 295
<211> LENGTH: 57
<212> TYPE: DNA
<213> ORGANISM: Artificial Sequence
<220> FEATURE:
<223> OTHER INFORMATION: Synthetic

<400> SEQUENCE: 295
gcaaaagagg gtataccagt ggctgggacg tatttccact tctacggtat ggacgtc         57

<210> SEQ ID NO 296
<211> LENGTH: 19
<212> TYPE: PRT
<213> ORGANISM: Artificial Sequence
<220> FEATURE:
<223> OTHER INFORMATION: Synthetic

<400> SEQUENCE: 296

```
Ala Lys Glu Gly Ile Pro Val Ala Gly Thr Tyr Phe His Phe Tyr Gly
1               5                   10                  15

Met Asp Val
```

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297

```
gaaatagtga tgacgcagtc tccagccacc ctgtctgtgt ctccagggga aagagtcacc    60
ctctcctgca gggccagtca gagtattggc aactacttag cctggtacca gcagaaacct   120
ggccaggctc ccaggctcct catctatggt acatccacca gggccactgg tatcccagcc   180
aggttcagtg gcagtgggtc tgggacagag ttcactctca ccttcagcag cctgcagtct   240
gaagattttg cagtttatta ctgtcagcag tataatcact ggccgctcac tttcggcgga   300
gggaccaagg tggagatcaa a                                             321
```

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

```
Glu Ile Val Met Thr Gln Ser Pro Ala Thr Leu Ser Val Ser Pro Gly
  1               5                  10                  15

Glu Arg Val Thr Leu Ser Cys Arg Ala Ser Gln Ser Ile Gly Asn Tyr
             20                  25                  30

Leu Ala Trp Tyr Gln Gln Lys Pro Gly Gln Ala Pro Arg Leu Leu Ile
         35                  40                  45

Tyr Gly Thr Ser Thr Arg Ala Thr Gly Ile Pro Ala Arg Phe Ser Gly
     50                  55                  60

Ser Gly Ser Gly Thr Glu Phe Thr Leu Thr Phe Ser Ser Leu Gln Ser
 65                  70                  75                  80

Glu Asp Phe Ala Val Tyr Tyr Cys Gln Gln Tyr Asn His Trp Pro Leu
                 85                  90                  95

Thr Phe Gly Gly Gly Thr Lys Val Glu Ile Lys
            100                 105
```

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299

```
cagagtattg gcaactac                                                  18
```

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

```
Gln Ser Ile Gly Asn Tyr
  1               5
```

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 ggtacatcc                                                                9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Gly Thr Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
cagcagtata atcactggcc gctcact                                           27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Tyr Asn His Trp Pro Leu Thr
 1               5

<210> SEQ ID NO 305
<211> LENGTH: 360
<212> TYPE: DNA
<213> ORGANISM: Artificial Sequence
<220> FEATURE:
<223> OTHER INFORMATION: Synthetic

<400> SEQUENCE: 305
caggttcagc tggtgcagtc tggggctgag gtgaagaagc ctggggccgc agtgaaggtc       60
tcctgcaagg cttctggata caccttcacc gactaccata tgcattgggt gcgacaggcc      120
cctggacaag gcttgagtg gatgggatgg atcaaccctaacagtggtgg cacaaactct       180 gcacagaagt ttcagggcag ggtcaccatg accagggaca cgtccatcag cacagcctac      240
atggaactga acggtctgag atctgacgac acggccgtct attactgtgc gagaaaggcc      300
gggtttacca gtagctggtt cgaccactgg ggccagggaa ccacggtcac cgtctcctca      360

<210> SEQ ID NO 306
<211> LENGTH: 120
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Gln Ser Gly Ala Glu Val Lys Lys Pro Gly Ala
1               5                   10                  15
Ala Val Lys Val Ser Cys Lys Ala Ser Gly Tyr Thr Phe Thr Asp Tyr
            20                  25                  30
His Met His Trp Val Arg Gln Ala Pro Gly Gln Gly Leu Glu Trp Met
        35                  40                  45
Gly Trp Ile Asn Pro Asn Ser Gly Gly Thr Asn Ser Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Asn Gly Leu Arg Ser Asp Asp Thr Ala Val Tyr Tyr Cys
                85                  90                  95
Ala Arg Lys Ala Gly Phe Thr Ser Ser Trp Phe Asp His Trp Gly Gln
            100                 105                 110
Gly Thr Thr Val Thr Val Ser Ser
        115                 120

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggatacacct tcaccgacta ccat                                          24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Tyr Thr Phe Thr Asp Tyr His
1               5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309 atcaaccta acagtggtgg caca                                           24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Asn Pro Asn Ser Gly Gly Thr
1               5

<210> SEQ ID NO 311

<211> LENGTH: 39
<212> TYPE: DNA
<213> ORGANISM: Artificial Sequence
<220> FEATURE:
<223> OTHER INFORMATION: Synthetic

<400> SEQUENCE: 311
gcgagaaagg ccgggtttac cagtagctgg ttcgaccac                           39

<210> SEQ ID NO 312
<211> LENGTH: 13
<212> TYPE: PRT
<213> ORGANISM: Artificial Sequence
<220> FEATURE:
<223> OTHER INFORMATION: Synthetic

<400> SEQUENCE: 312

Ala Arg Lys Ala Gly Phe Thr Ser Ser Trp Phe Asp His
 1               5                   10

<210> SEQ ID NO 313
<211> LENGTH: 336
<212> TYPE: DNA
<213> ORGANISM: Artificial Sequence
<220> FEATURE:
<223> OTHER INFORMATION: Synthetic

<400> SEQUENCE: 313
gatattgtga tgacccagtc tccagactcc ctggctgtgt ctctgggcga gagggccacc    60
atcaactgca gtccagcca gagtgtttta tacagcttca acaataagaa ctacttaact   120
tggtaccagc agaaaccagg acagcctcct aagctgctca tttactgggc atctactcgg   180
gaatccgggg tccctgaccg attcagtggc agcgggtctg ggacagattt cactctcacc   240
atcagcagcc tgcaggctga agatgtggca gtttattact gtcagcaata ttatagtctg   300
atcactttcg gccaagggac acgactggag attaaa                             336

<210> SEQ ID NO 314
<211> LENGTH: 112
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Val Leu Tyr Ser
                20                  25                  30

Phe Asn Asn Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Leu Ile Thr Phe Gly Gln Gly Thr Arg Leu Glu Ile Lys
            100                 105                 110

<210> SEQ ID NO 315
<211> LENGTH: 36

```
<212> TYPE: DNA
<213> ORGANISM: Artificial Sequence
<220> FEATURE:
<223> OTHER INFORMATION: Synthetic

<400> SEQUENCE: 315
cagagtgttt tatacagctt caacaataag aactac                           36

<210> SEQ ID NO 316
<211> LENGTH: 12
<212> TYPE: PRT
<213> ORGANISM: Artificial Sequence
<220> FEATURE:
<223> OTHER INFORMATION: Synthetic

<400> SEQUENCE: 316

Gln Ser Val Leu Tyr Ser Phe Asn Asn Lys Asn Tyr
 1               5                  10

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 tgggcatct                                                          9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Trp Ala Ser
 1

<210> SEQ ID NO 319
<211> LENGTH: 24
<212> TYPE: DNA
<213> ORGANISM: Artificial Sequence
<220> FEATURE:
<223> OTHER INFORMATION: Synthetic

<400> SEQUENCE: 319
cagcaatatt atagtctgat cact                                        24

<210> SEQ ID NO 320
<211> LENGTH: 8
<212> TYPE: PRT
<213> ORGANISM: Artificial Sequence
<220> FEATURE:
<223> OTHER INFORMATION: Synthetic

<400> SEQUENCE: 320

Gln Gln Tyr Tyr Ser Leu Ile Thr
 1               5

<210> SEQ ID NO 321
<211> LENGTH: 360
<212> TYPE: DNA
<213> ORGANISM: Artificial Sequence
<220> FEATURE:
<223> OTHER INFORMATION: Synthetic
```

<400> SEQUENCE: 321

```
caggtgcagc tggtacagtc tggggctgag gtgaagaagc ctggggcctc agtgaaggtc      60
tcctgtaagg cttctggata caccttcacc gactactttc ttcactgggt gcgacaggcc     120
cctggacaag gccttgagtg gtgggatgg atcaaccta acagtggtgg cacaaacttt       180
gcacagaagt tcagggcag ggtcaccatg accagggaca cgtccatcag cacagcctac      240
atggacctga gcagactgag atctgacgac acggccgttt attactgtgc gagaaaggcc     300
ggatatacca gcagctggtt cgactactgg ggccagggaa ccctggtcac cgtctcctca     360
```

<210> SEQ ID NO 322
<211> LENGTH: 120
<212> TYPE: PRT
<213> ORGANISM: Artificial Sequence
<220> FEATURE:
<223> OTHER INFORMATION: Synthetic

<400> SEQUENCE: 322

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Phe Leu His Trp Val Arg Gln Ala Pro Gly Gln Gly Leu Glu Trp Val
        35                  40                  45

Gly Trp Ile Asn Pro Asn Ser Gly Gly Thr Asn Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Tyr Tyr Cys
                85                  90                  95

Ala Arg Lys Ala Gly Tyr Thr Ser Ser Trp Phe Asp Tyr Trp Gly Gln
            100                 105                 110

Gly Thr Leu Val Thr Val Ser Ser
        115                 120
```

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323

```
ggatacacct tcaccgacta cttt                                             24
```

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

```
Gly Tyr Thr Phe Thr Asp Tyr Phe
1               5
```

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
atcaacccta acagtggtgg caca                                          24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Asn Pro Asn Ser Gly Gly Thr
 1               5

<210> SEQ ID NO 327
<211> LENGTH: 39
<212> TYPE: DNA
<213> ORGANISM: Artificial Sequence
<220> FEATURE:
<223> OTHER INFORMATION: Synthetic

<400> SEQUENCE: 327
gcgagaaagg ccggatatac cagcagctgg ttcgactac                          39

<210> SEQ ID NO 328
<211> LENGTH: 13
<212> TYPE: PRT
<213> ORGANISM: Artificial Sequence
<220> FEATURE:
<223> OTHER INFORMATION: Synthetic

<400> SEQUENCE: 328

Ala Arg Lys Ala Gly Tyr Thr Ser Ser Trp Phe Asp Tyr
 1               5                  10

<210> SEQ ID NO 329
<211> LENGTH: 336
<212> TYPE: DNA
<213> ORGANISM: Artificial Sequence
<220> FEATURE:
<223> OTHER INFORMATION: Synthetic

<400> SEQUENCE: 329
gacatcgtga tgacccagtc tccagactcc ctggctgtgt ctctgggcga gagggccacc    60
ataaactgca agtccagcca gagtatttta tacagcttca acaataagaa ctacttagct   120
tggtaccagc agaaaatagg acagcctcct atgctgctca tttactgggc atctacccgg   180
gaatccgggg tccctgaccg attcagtggc agcgggtctg ggacagattt cactctcacc   240
ataagcagac tgcaggctga agatgtggca gtttattact gtcagcaata ttatagttcg   300
atcaccttcg gccaagggac acgactggag attaaa                             336

<210> SEQ ID NO 330
<211> LENGTH: 112
<212> TYPE: PRT
<213> ORGANISM: Artificial Sequence
<220> FEATURE:
<223> OTHER INFORMATION: Synthetic

<400> SEQUENCE: 330

Asp Ile Val Met Thr Gln Ser Pro Asp Ser Leu Ala Val Ser Leu Gly
 1               5                  10                  15

```
Glu Arg Ala Thr Ile Asn Cys Lys Ser Ser Gln Ser Ile Leu Tyr Ser
         20                  25                  30

Phe Asn Asn Lys Asn Tyr Leu Ala Trp Tyr Gln Gln Lys Ile Gly Gln
             35                  40                  45

Pro Pro Met Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Arg Leu Gln Ala Glu Asp Val Ala Val Tyr Tyr Cys Gln Gln
                 85                  90                  95

Tyr Tyr Ser Ser Ile Thr Phe Gly Gln Gly Thr Arg Leu Glu Ile Lys
            100                 105                 110
```

<210> SEQ ID NO 331
<211> LENGTH: 36
<212> TYPE: DNA
<213> ORGANISM: Artificial Sequence
<220> FEATURE:
<223> OTHER INFORMATION: Synthetic

<400> SEQUENCE: 331
cagagtattt tatacagctt caacaataag aactac     36

<210> SEQ ID NO 332
<211> LENGTH: 12
<212> TYPE: PRT
<213> ORGANISM: Artificial Sequence
<220> FEATURE:
<223> OTHER INFORMATION: Synthetic

<400> SEQUENCE: 332

```
Gln Ser Ile Leu Tyr Ser Phe Asn Asn Lys Asn Tyr
 1               5                  10
```

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 tgggcatct     9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

```
Trp Ala Ser
 1
```

<210> SEQ ID NO 335
<211> LENGTH: 24
<212> TYPE: DNA
<213> ORGANISM: Artificial Sequence
<220> FEATURE:
<223> OTHER INFORMATION: Synthetic

<400> SEQUENCE: 335
cagcaatatt atagttcgat cacc 24

<210> SEQ ID NO 336
<211> LENGTH: 8
<212> TYPE: PRT
<213> ORGANISM: Artificial Sequence
<220> FEATURE:
<223> OTHER INFORMATION: Synthetic

<400> SEQUENCE: 336

Gln Gln Tyr Tyr Ser Ser Ile Thr
 1               5

<210> SEQ ID NO 337
<211> LENGTH: 360
<212> TYPE: DNA
<213> ORGANISM: Artificial Sequence
<220> FEATURE:
<223> OTHER INFORMATION: Synthetic

<400> SEQUENCE: 337
caggtgcagc tggtgcagtc tggggctgaa gtgaagaagc ctggggcctc agtgaaggtc    60
tcctgcaagg cttctggata caccttcacc ggctacttta tccactgggt gcgacaggcc   120
cctggacaag ggcttgagtg gtgggatgga atcaaccctc ccagtggtgg cacaaactat   180
gcacagaagt tcagggcag gtcaccatg accaggaca cgtccatcag cacagcctat   240
atggagatga acagtctgag atctgacgac acggccgtgt attactgtgc gagaaaggcc   300
gggtatacca gcacctggtt cgactactgg ggccagggaa ccacggtcac cgtctcctca   360

<210> SEQ ID NO 338
<211> LENGTH: 120
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Phe Ile His Trp Val Arg Gln Ala Pro Gly Gln Gly Leu Glu Trp Val
            35                  40                  45

Gly Trp Ile Asn Pro Thr Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Met Asn Ser Leu Arg Ser Asp Asp Thr Ala Val Tyr Tyr Cys
                85                  90                  95

Ala Arg Lys Ala Gly Tyr Thr Ser Thr Trp Phe Asp Tyr Trp Gly Gln
                100                 105                 110

Gly Thr Thr Val Thr Val Ser Ser
            115                 120

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggatacacct tcaccggcta cttt                                          24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Tyr Thr Phe Thr Gly Tyr Phe
 1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
atcaacccta ccagtggtgg caca                                          24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Asn Pro Thr Ser Gly Gly Thr
 1               5

<210> SEQ ID NO 343
<211> LENGTH: 39
<212> TYPE: DNA
<213> ORGANISM: Artificial Sequence
<220> FEATURE:
<223> OTHER INFORMATION: Synthetic

<400> SEQUENCE: 343
gcgagaaagg ccgggtatac cagcacctgg ttcgactac                          39

<210> SEQ ID NO 344
<211> LENGTH: 13
<212> TYPE: PRT
<213> ORGANISM: Artificial Sequence
<220> FEATURE:
<223> OTHER INFORMATION: Synthetic

<400> SEQUENCE: 344

Ala Arg Lys Ala Gly Tyr Thr Ser Thr Trp Phe Asp Tyr
 1               5                  10

<210> SEQ ID NO 345
<211> LENGTH: 336
<212> TYPE: DNA
<213> ORGANISM: Artificial Sequence
<220> FEATURE:
<223> OTHER INFORMATION: Synthetic

<400> SEQUENCE: 345
gacatcgtga tgacccagtc tccagactcc ctgactgtgt ctctgggcga gagggccacc    60

| | |
|---|---|
| atcaactgca agtccagtca gagtgtttta tacagttcca aaaataagaa ctacttagct | 120 |
| tggtaccagc agaaaccagg acagcctcct aatctgctcg tttactgggc atctacccgg | 180 |
| gaatccgggg tccctgaccg attcagtggc agcgggtctg ggacagattt cactctcacc | 240 |
| atcagcagcc tgcaggctga agatgtggca gtttattact gtcagcaata ttatagtatg | 300 |
| atcaccttcg gccaagggac acgactggag attaaa | 336 |

<210> SEQ ID NO 346
<211> LENGTH: 112
<212> TYPE: PRT
<213> ORGANISM: Artificial Sequence
<220> FEATURE:
<223> OTHER INFORMATION: Synthetic

<400> SEQUENCE: 346

Asp Ile Val Met Thr Gln Ser Pro Asp Ser Leu Thr Val Ser Leu Gly
1               5                   10                  15

Glu Arg Ala Thr Ile Asn Cys Lys Ser Ser Gln Ser Val Leu Tyr Ser
            20                  25                  30

Ser Lys Asn Lys Asn Tyr Leu Ala Trp Tyr Gln Gln Lys Pro Gly Gln
        35                  40                  45

Pro Pro Asn Leu Leu Val Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Met Ile Thr Phe Gly Gln Gly Thr Arg Leu Glu Ile Lys
            100                 105                 110

<210> SEQ ID NO 347
<211> LENGTH: 36
<212> TYPE: DNA
<213> ORGANISM: Artificial Sequence
<220> FEATURE:
<223> OTHER INFORMATION: Synthetic

<400> SEQUENCE: 347
cagagtgttt tatacagttc aaaaataag aactac                              36

<210> SEQ ID NO 348
<211> LENGTH: 12
<212> TYPE: PRT
<213> ORGANISM: Artificial Sequence
<220> FEATURE:
<223> OTHER INFORMATION: Synthetic

<400> SEQUENCE: 348

Gln Ser Val Leu Tyr Ser Ser Lys Asn Lys Asn Tyr
1               5                   10

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 tgggcatct                                                            9

```
<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Trp Ala Ser
 1

<210> SEQ ID NO 351
<211> LENGTH: 24
<212> TYPE: DNA
<213> ORGANISM: Artificial Sequence
<220> FEATURE:
<223> OTHER INFORMATION: Synthetic

<400> SEQUENCE: 351
cagcaatatt atagtatgat cacc                                            24

<210> SEQ ID NO 352
<211> LENGTH: 8
<212> TYPE: PRT
<213> ORGANISM: Artificial Sequence
<220> FEATURE:
<223> OTHER INFORMATION: Synthetic

<400> SEQUENCE: 352

Gln Gln Tyr Tyr Ser Met Ile Thr
 1               5

<210> SEQ ID NO 353
<211> LENGTH: 360
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggtacagc ctgggggtc cctgagactc       60 tcctgtgcag cctctggatt cacctttacc aactatgcca tgacctgggt ccgccaggct      120
ccagggaagg ggctggagtg ggtctcaact attagtggta ctggtgttga tatcacatac      180
tacgcagact ccgtgaaggg ccggttcacc atctccagag acaattccaa gaacacgctg      240
tatctgcaaa tgaacagcct gagagccgag gacacggccg tatattactg tgcgaaagga      300
ggactacggt ggttcccctt tgactactgg ggccagggaa ccacggtcac cgtctcctca      360

<210> SEQ ID NO 354
<211> LENGTH: 120
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
             20                  25                  30

Ala Met Thr Trp Val Arg Gln Ala Pro Gly Lys Gly Leu Glu Trp Val
         35                  40                  45

Ser Thr Ile Ser Gly Thr Gly Val Asp Ile Thr Tyr Tyr Ala Asp Ser
```

```
                50                  55                  60
Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Gly Gly Leu Arg Trp Phe Pro Phe Asp Tyr Trp Gly Gln
            100                 105                 110

Gly Thr Thr Val Thr Val Ser Ser
        115                 120
```

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcacct ttaccaacta tgcc        24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

```
Gly Phe Thr Phe Thr Asn Tyr Ala
 1               5
```

<210> SEQ ID NO 357
<211> LENGTH: 27
<212> TYPE: DNA
<213> ORGANISM: Artificial Sequence
<220> FEATURE:
<223> OTHER INFORMATION: Synthetic

<400> SEQUENCE: 357
attagtggta ctggtgttga tatcaca        27

<210> SEQ ID NO 358
<211> LENGTH: 9
<212> TYPE: PRT
<213> ORGANISM: Artificial Sequence
<220> FEATURE:
<223> OTHER INFORMATION: Synthetic

<400> SEQUENCE: 358

```
Ile Ser Gly Thr Gly Val Asp Ile Thr
 1               5
```

<210> SEQ ID NO 359
<211> LENGTH: 36
<212> TYPE: DNA
<213> ORGANISM: Artificial Sequence
<220> FEATURE:
<223> OTHER INFORMATION: Synthetic

<400> SEQUENCE: 359
gcgaaaggag gactacggtg gttcccttt gactac        36

<210> SEQ ID NO 360
<211> LENGTH: 12

```
<212> TYPE: PRT
<213> ORGANISM: Artificial Sequence
<220> FEATURE:
<223> OTHER INFORMATION: Synthetic

<400> SEQUENCE: 360

Ala Lys Gly Gly Leu Arg Trp Phe Pro Phe Asp Tyr
 1               5                  10

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt tttctcggac gttcggccaa   300
gggaccaagg tggaaatcaa a                                             321

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Phe Ser Arg
                 85                  90                  95

Thr Phe Gly Gln Gly Thr Lys Val Glu Ile Lys
            100                 105

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagagtatta gtagctgg                                                  18

<210> SEQ ID NO 364
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 364

Gln Ser Ile Ser Ser Trp
 1               5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 aaggcgtct                                                              9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Lys Ala Ser
 1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
caacagtata atagttttc tcggacg                                          27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Gln Tyr Asn Ser Phe Ser Arg Thr
 1               5

<210> SEQ ID NO 369
<211> LENGTH: 357
<212> TYPE: DNA
<213> ORGANISM: Artificial Sequence
<220> FEATURE:
<223> OTHER INFORMATION: Synthetic

<400> SEQUENCE: 369
gaggtgcagc tggtggagtc tgggggaggc ttggtacagc ctgggggtc cctgagactc      60 tcctgtgcag cctcaggaat caccttagc agctttgtca tgaactgggt ccgccaggct    120
ccagggaagg gctggagtg gtctcagtt attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaggagga    300
```

```
ctacggtggt tcccctttga ctactggggc cagggaaccc tggtcactgt ctcctca        357
```

<210> SEQ ID NO 370
<211> LENGTH: 119
<212> TYPE: PRT
<213> ORGANISM: Artificial Sequence
<220> FEATURE:
<223> OTHER INFORMATION: Synthetic

<400> SEQUENCE: 370

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Thr Phe Ser Ser Phe
            20                  25                  30

Val Met Asn Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Leu Arg Trp Phe Pro Phe Asp Tyr Trp Gly Gln Gly
            100                 105                 110

Thr Leu Val Thr Val Ser Ser
        115
```

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371

```
ggaatcacct ttagcagctt tgtc                                              24
```

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

```
Gly Ile Thr Phe Ser Ser Phe Val
 1               5
```

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373

```
attagtggta gtggtggtag caca                                              24
```

<210> SEQ ID NO 374
<211> LENGTH: 8
<212> TYPE: PRT
<213> ORGANISM: Artificial Sequence
<220> FEATURE:

<223> OTHER INFORMATION: Synthetic

<400> SEQUENCE: 374

Ile Ser Gly Ser Gly Gly Ser Thr
1               5

<210> SEQ ID NO 375
<211> LENGTH: 36
<212> TYPE: DNA
<213> ORGANISM: Artificial Sequence
<220> FEATURE:
<223> OTHER INFORMATION: Synthetic

<400> SEQUENCE: 375
gcgaaaggag gactacggtg gttcccttt gactac                                    36

<210> SEQ ID NO 376
<211> LENGTH: 12
<212> TYPE: PRT
<213> ORGANISM: Artificial Sequence
<220> FEATURE:
<223> OTHER INFORMATION: Synthetic

<400> SEQUENCE: 376

Ala Lys Gly Gly Leu Arg Trp Phe Pro Phe Asp Tyr
1               5                   10

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gacatccaga tgacccagtc tccttccacc ctgtctgcat ctgtaggaga cagagtcacc        60
atcacttgcc gggccagtca gagtattagt agttggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagtt attctcggac gttcggccaa       300
gggaccaagg tggaaatcaa a                                                 321

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379
cagagtatta gtagttgg                                                   18

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

Gln Ser Ile Ser Ser Trp
 1               5

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381 aaggcgtct                                                              9

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Lys Ala Ser
 1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
caacagtata atagttattc tcggacg                                         27

<210> SEQ ID NO 384
<211> LENGTH: 9
<212> TYPE: PRT
<213> ORGANISM: Artificial Sequence
<220> FEATURE:
<223> OTHER INFORMATION: Synthetic
```

<400> SEQUENCE: 384

Gln Gln Tyr Asn Ser Tyr Ser Arg Thr
1               5

<210> SEQ ID NO 385
<211> LENGTH: 362
<212> TYPE: PRT
<213> ORGANISM: Artificial Sequence
<220> FEATURE:
<223> OTHER INFORMATION: Synthetic

<400> SEQUENCE: 385

Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
        35                  40                  45

Val Gly Tyr Val Asp Asp Thr Leu Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln Asp Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 386
<211> LENGTH: 362
<212> TYPE: PRT
<213> ORGANISM: Artificial Sequence
<220> FEATURE:
<223> OTHER INFORMATION: Synthetic

<400> SEQUENCE: 386

Met Arg Val Thr Ala Pro Arg Thr Leu Leu Leu Leu Trp Gly Ala
 1               5                  10                  15

Val Ala Leu Thr Glu Thr Trp Ala Gly Ser His Ser Met Arg Tyr Phe
                20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
            100                 105                 110

Glu Ala Gly Ser His Thr Leu Gln Asn Met Tyr Gly Cys Asp Val Gly
        115                 120                 125

Pro Asp Gly Arg Leu Leu Arg Gly Tyr His Gln His Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

```
Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 387
<211> LENGTH: 437
<212> TYPE: PRT
<213> ORGANISM: Artificial Sequence
<220> FEATURE:
<223> OTHER INFORMATION: Synthetic

<400> SEQUENCE: 387

Ser Arg Tyr Trp Ala Ile Arg Thr Arg Gly Gly Gly Ser Gly Gly
  1               5                  10                  15

Gly Gly Ser Ile Gln Arg Thr Pro Lys Ile Gln Val Tyr Ser Arg His
                20                  25                  30

Pro Ala Glu Asn Gly Lys Ser Asn Phe Leu Asn Cys Tyr Val Ser Gly
            35                  40                  45

Phe His Pro Ser Asp Ile Glu Val Asp Leu Leu Lys Asn Gly Glu Arg
        50                  55                  60

Ile Glu Lys Val Glu His Ser Asp Leu Ser Phe Ser Lys Asp Trp Ser
 65                  70                  75                  80

Phe Tyr Leu Leu Tyr Tyr Thr Glu Phe Thr Pro Thr Glu Lys Asp Glu
                 85                  90                  95

Tyr Ala Cys Arg Val Asn His Val Thr Leu Ser Gln Pro Lys Ile Val
            100                 105                 110

Lys Trp Asp Arg Asp Met Gly Gly Gly Ser Gly Gly Gly Gly Ser
        115                 120                 125

Gly Gly Gly Gly Ser Gly Ser His Ser Met Arg Tyr Phe His Thr Ser
    130                 135                 140

Val Ser Arg Pro Gly Arg Gly Glu Pro Arg Phe Ile Thr Val Gly Tyr
145                 150                 155                 160

Val Asp Asp Thr Leu Phe Val Arg Phe Asp Ser Asp Ala Ala Ser Pro
                165                 170                 175

Arg Glu Glu Pro Arg Ala Pro Trp Ile Glu Gln Glu Gly Pro Glu Tyr
            180                 185                 190

Trp Asp Arg Glu Thr Gln Ile Cys Lys Ala Lys Ala Gln Thr Asp Arg
        195                 200                 205

Glu Asp Leu Arg Thr Leu Leu Arg Tyr Tyr Asn Gln Ser Glu Ala Gly
    210                 215                 220

Ser His Thr Leu Gln Asn Met Tyr Gly Cys Asp Val Gly Pro Asp Gly
225                 230                 235                 240

Arg Leu Leu Arg Gly Tyr His Gln Asp Ala Tyr Asp Gly Lys Asp Tyr
                245                 250                 255

Ile Ala Leu Asn Glu Asp Leu Ser Ser Trp Thr Ala Ala Asp Thr Ala
            260                 265                 270

Ala Gln Ile Thr Gln Arg Lys Trp Glu Ala Ala Arg Val Ala Glu Gln
        275                 280                 285

Leu Arg Ala Tyr Leu Glu Gly Glu Cys Val Glu Trp Leu Arg Arg Tyr
    290                 295                 300

Leu Glu Asn Gly Lys Glu Thr Leu Gln Arg Ala Asp Pro Pro Lys Thr
305                 310                 315                 320

His Val Thr His His Pro Ile Ser Asp His Glu Ala Thr Leu Arg Cys
                325                 330                 335
```

```
Trp Ala Leu Gly Phe Tyr Pro Ala Glu Ile Thr Leu Thr Trp Gln Arg
            340                 345                 350

Asp Gly Glu Asp Gln Thr Gln Asp Thr Glu Leu Val Glu Thr Arg Pro
        355                 360                 365

Ala Gly Asp Arg Thr Phe Gln Lys Trp Ala Ala Val Val Val Pro Ser
    370                 375                 380

Gly Glu Glu Gln Arg Tyr Thr Cys His Val Gln His Glu Gly Leu Pro
385                 390                 395                 400

Lys Pro Leu Thr Leu Arg Trp Glu Pro Glu Gln Lys Leu Ile Ser Glu
                405                 410                 415

Glu Asp Leu Gly Gly Glu Gln Lys Leu Ile Ser Glu Glu Asp Leu His
                420                 425                 430

His His His His His
        435

<210> SEQ ID NO 388
<211> LENGTH: 119
<212> TYPE: PRT
<213> ORGANISM: Homo sapiens

<400> SEQUENCE: 388

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 389
<211> LENGTH: 9
<212> TYPE: PRT
<213> ORGANISM: Artificial Sequence
<220> FEATURE:
<223> OTHER INFORMATION: Synthetic

<400> SEQUENCE: 389

Ser Arg Tyr Trp Ala Ile Arg Thr Arg
1               5

<210> SEQ ID NO 390
<211> LENGTH: 276
<212> TYPE: PRT
<213> ORGANISM: Artificial Sequence
<220> FEATURE:
<223> OTHER INFORMATION: Synthetic
```

<400> SEQUENCE: 390

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Phe Ser Gly Gly Ser Asn Tyr Lys Leu Thr Phe Gly Lys Gly
        115                 120                 125

Thr Leu Leu Thr Val Asn Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 391
<211> LENGTH: 310
<212> TYPE: PRT
<213> ORGANISM: Artificial Sequence
<220> FEATURE:
<223> OTHER INFORMATION: Synthetic

<400> SEQUENCE: 391

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Gln Glu Val Leu Asp Thr Gln Tyr Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 392
<211> LENGTH: 214
<212> TYPE: PRT
<213> ORGANISM: Artificial Sequence
<220> FEATURE:
<223> OTHER INFORMATION: Synthetic

<400> SEQUENCE: 392

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
        50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

```
Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr Leu Tyr Cys Asn His Arg Asn Arg Arg Arg
                180                 185                 190

Val Cys Lys Cys Pro Arg Pro Val Val Lys Ser Gly Asp Lys Pro Ser
        195                 200                 205

Leu Ser Ala Arg Tyr Val
    210

<210> SEQ ID NO 393
<211> LENGTH: 189
<212> TYPE: PRT
<213> ORGANISM: Artificial Sequence
<220> FEATURE:
<223> OTHER INFORMATION: Synthetic

<400> SEQUENCE: 393

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
                20                  25                  30

Trp Leu Arg Gln Arg Gln Ala Pro Ser Ser Asp Ser His His Glu Phe
            35                  40                  45

Leu Ala Leu Trp Asp Ser Ala Lys Gly Thr Ile His Gly Glu Glu Val
        50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
                100                 105                 110

Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
        130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Phe Tyr Lys
            180                 185
```